(12) United States Patent
Gross et al.

(10) Patent No.: US 7,847,245 B2
(45) Date of Patent: Dec. 7, 2010

(54) MULTIPLEXING MATRIX-ANALYTE STEREO ELECTRONIC INTERACTIONS FOR HIGH THROUGHPUT SHOTGUN METABOLOMICS

(75) Inventors: Richard W. Gross, Chesterfield, MO (US); Gang Sun, Madison, WI (US); Xianlin Han, Clayton, MO (US)

(73) Assignee: Platomics, Inc., Chesterfield, MO (US)

( * ) Notice: Subject to any disclaimer, the term of this patent is extended or adjusted under 35 U.S.C. 154(b) by 298 days.

(21) Appl. No.: 12/174,493

(22) Filed: Jul. 16, 2008

(65) Prior Publication Data

US 2009/0065687 A1    Mar. 12, 2009

Related U.S. Application Data

(60) Provisional application No. 60/961,068, filed on Jul. 18, 2007.

(51) Int. Cl.
*B01D 59/44* (2006.01)
*H01J 49/40* (2006.01)
*H01J 49/04* (2006.01)

(52) U.S. Cl. .................. 250/288; 250/281; 250/282
(58) Field of Classification Search ............. 250/281, 250/282, 286–288, 492.1
See application file for complete search history.

(56) References Cited

U.S. PATENT DOCUMENTS

| | | | |
|---|---|---|---|
| 5,808,300 A | 9/1998 | Caprioli | |
| 6,982,414 B2 | 1/2006 | Bateman et al. | |
| 7,112,784 B2 | 9/2006 | Bateman et al. | |
| 7,241,989 B2 | 7/2007 | Miller et al. | |
| 7,291,835 B2 | 11/2007 | Overney | |
| 7,306,952 B2 * | 12/2007 | Gross et al. | 436/173 |
| 7,411,183 B2 | 8/2008 | Overney et al. | |
| 7,498,568 B2 | 3/2009 | Overney et al. | |
| 7,510,880 B2 * | 3/2009 | Gross et al. | 436/71 |
| 2005/0026148 A1 * | 2/2005 | Rexhausen et al. | 435/6 |

\* cited by examiner

*Primary Examiner*—Bernard E Souw
(74) *Attorney, Agent, or Firm*—Armstrong Teasdale LLP

(57) ABSTRACT

A shotgun metabolomics approach using MALDI-tandem mass spectrometry was developed for the rapid analysis of cellular metabolites. Through the use of neutral organic solvents to inactivate endogenous enzyme activities (i.e., methanol/chloroform/$H_2O$ extraction), multiplexed extraction conditions and combinatorial alterations in matrix stereoelectronic composition and analyte interactions, multiple suites of metabolites were directly ionized and quantitated directly from biologic extracts without the need for prior chromatographic separation. Through combinatorial alterations in 9-aminoacridine charge, aromaticity and stacking, a set of multiplexed conditions was developed that allowed identification of many hundreds of peaks corresponding to metabolites from mouse heart extracts. Identification of metabolite peaks was based on mass accuracy and isomeric species were assigned based on diagnostic fragment ions present during tandem mass spectrometry for many of the identified metabolite peaks.

20 Claims, 36 Drawing Sheets

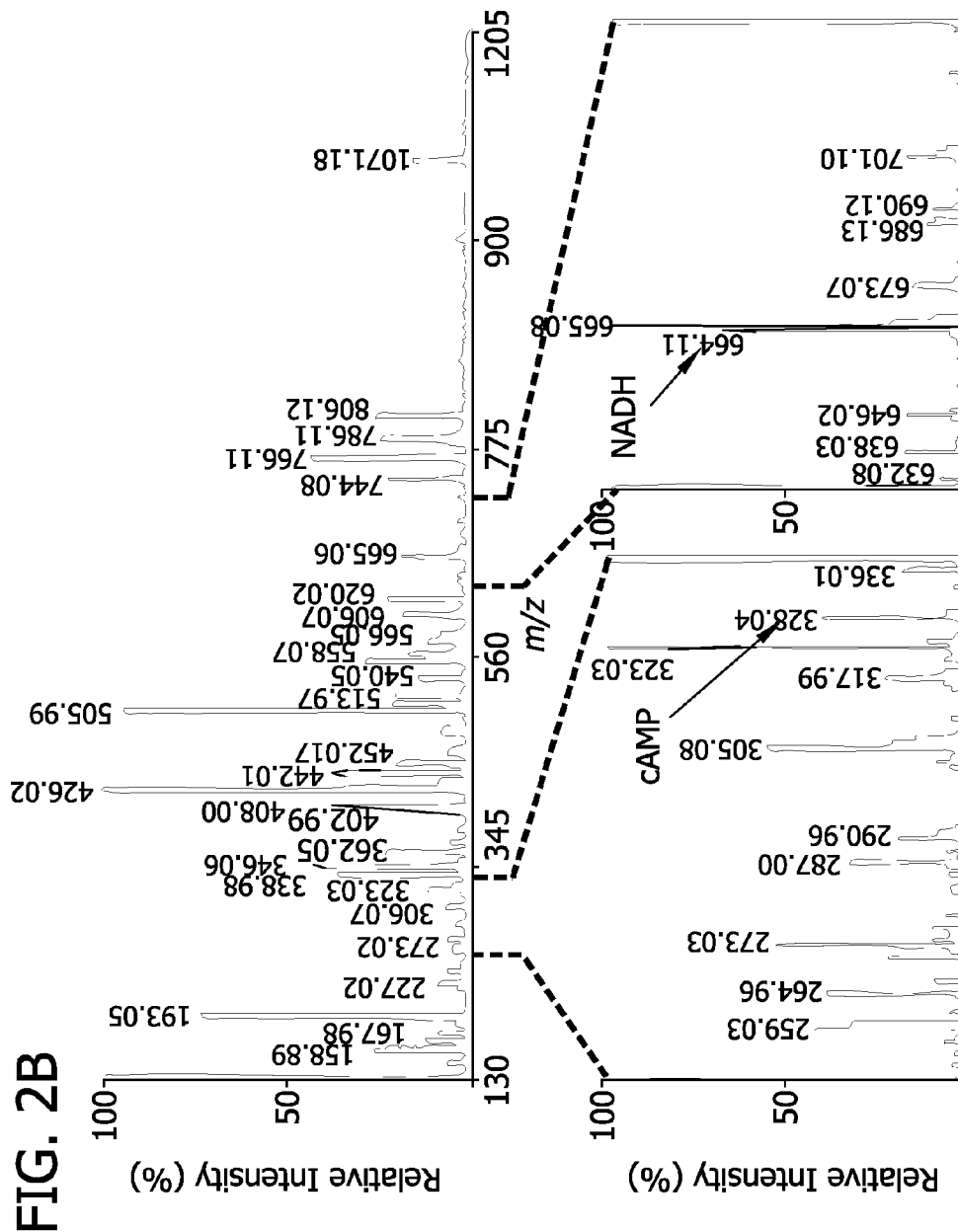

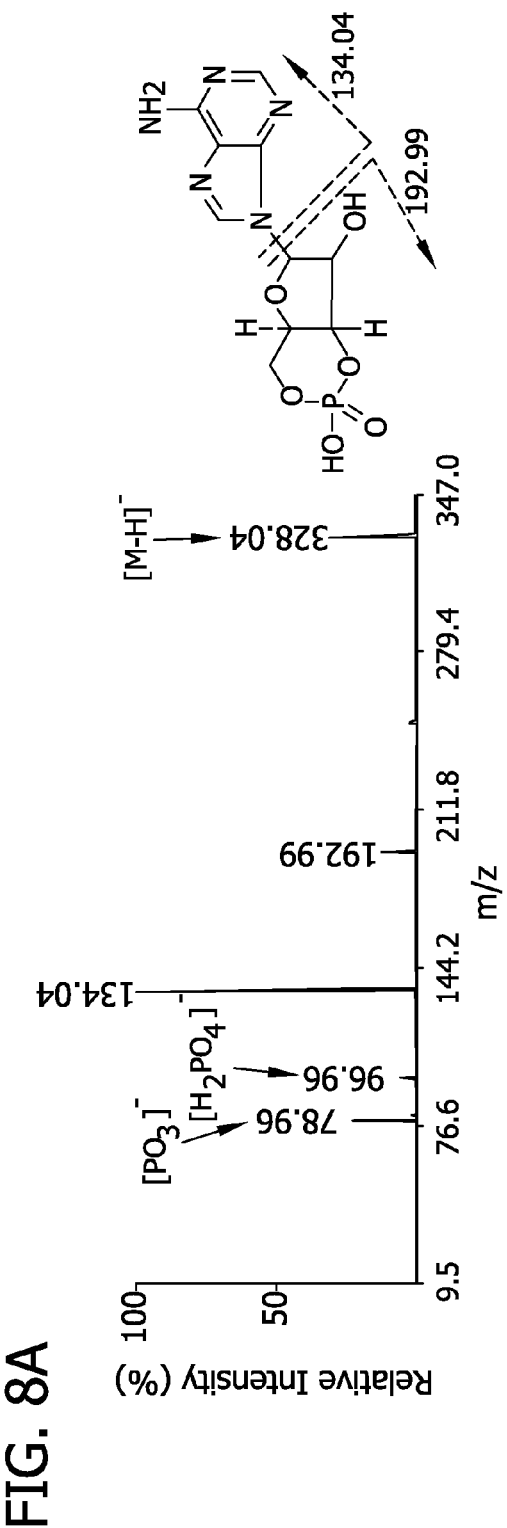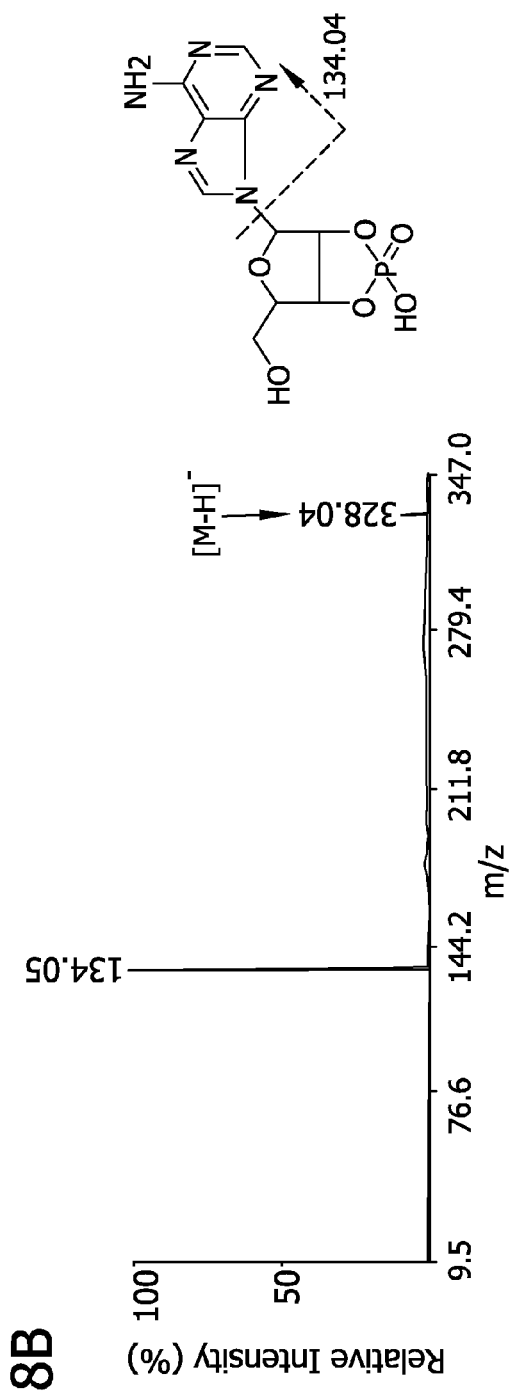
FIG. 8A
FIG. 8B

MULTIPLEXING MATRIX-ANALYTE STEREO ELECTRONIC INTERACTIONS FOR HIGH THROUGHPUT SHOTGUN METABOLOMICS This work was supported by the National Institutes of Health Grant P01 HL-57278.

CROSS-REFERENCE TO RELATED APPLICATION

This patent application is a non-provisional patent application of U.S. Provisional Patent Application No. 60/961,068, filed on Jul. 18, 2007, the entirety of which is hereby incorporated by reference.

BACKGROUND OF THE INVENTION

This invention relates generally to analysis of cellular metabolites that contain, or can be induced to contain one or more charges. More particularly, this invention relates to a shotgun metabolomics approach that exploits multiple combinatorial sets of engineered stereoelectronic interactions between matrix and analyte to enable high throughput metabolomics directly from extracts of biologic material without the need for prior chromatography. Through sequential matrix assisted laser desorption/ionization (MALDI) sets of chemically related metabolites can be selectively ionized, identified by tandem mass spectrometry and quantified. The novel properties of engineered analyte/matrix interactions containing resonance-stabilized delocalized charge allow the high throughput identification and quantitation of many hundreds of metabolites directly from extracts of biologic materials without prior chromatography. This approach has general utility for the determination of the chemical composition of complex mixtures of metabolites from biologic tissues, biologic fluids (e.g., blood, urine, cerebrospinal fluid) as well as metabolic flux measurements and pharmacokinetics through ratiometric comparisons with stable isotope standards.

Metabolomics is an emerging field that provides critical insight into the physiologic status of cells by identifying and quantifying multiple cellular metabolites. As a complement to genomics, proteomics, and transcriptomics, metabolomics has been successful in discriminating a wide variety of different metabolic phenotypes where more conventional assessments have failed. Through assessment of alterations in the profiles of metabolites, new insights into disease processes have already been made.

Among the various technologies that have traditionally been employed to identify and quantify cellular metabolites, mass spectrometry (MS) has evolved to be a very powerful tool for metabolite analysis. The high sensitivity and resolution of MS, in conjunction with its ability to elucidate the structure of unknown compounds present in complex biological samples, have provided a strong impetus to use MS in the analysis of metabolites present in low abundance (i.e., approximately less than about 0.1% of total content) and extremely low abundance (i.e. approximately less than about 0.01% of total content). However, the use of mass spectrometry in metabolomics has been severely limited by the difficulty in developing conditions for the ionization of large numbers of metabolites containing greatly differing chemical functionalities. In part, this previously intractable problem was due to the absence of an approach which provided rapid access to suitable combinations of ionization conditions that could be effectively multiplexed into a set of combinatorial conditions that facilitate selective ionization of the diverse sets of chemical functionalities present in metabolomes of biologic materials (e.g., tissues and fluids). Moreover, identification of mass alone does not establish the chemical structure of a metabolite due to the large number of isomeric metabolites present in nature. The use of tandem mass spectrometry, or other approaches, is necessary to identify the structure components and the isomeric composition of the analytes of interest.

Gas chromatograph mass spectrometry (GC-MS) has been widely used in the analyses of volatile metabolites or metabolites that can be volatized after chemical derivatization. Electrospray ionization mass spectrometry (ESI-MS) and atmospheric pressure chemical ionization mass spectrometry (APCI-MS) can be coupled to liquid chromatography (LC) or capillary electrophoresis (CE), allowing high-throughput analyses of nonvolatile metabolites from biological materials. These techniques have been recently reviewed and represent valuable tools for metabolomics research. The use of chromatography or electrophoresis, however, extends analysis time and introduces additional procedural complexity. Quantitative analysis of the chemically diverse molecular species present in the metabolome often requires multiple different chromatographic approaches to resolve or enrich salient metabolites. Current efforts in metabolomics are thus aimed at maximizing the amount of information obtained, while minimizing time and methodological difficulty necessary for sample analysis.

Matrix assisted laser desorption ionization mass spectrometry (MALDI-MS), and in addition, MALDI-tandem mass spectrometry, has now matured and are widely used in proteomics analysis, nucleotide sequencing, and polymer analysis, has the potential to contribute significantly to metabolomics. MALDI-MS permits the discrimination of isomeric molecular species that would not be possible using spectra of molecular ions alone. MALDI-MS has a higher tolerance to salts than ESI-MS and APCI-MS and has the unique ability to generate singly charged ions of less than about 1000 dalton (Da) which can avoid the overlapping of ion peaks produced by multiply charged ions routinely occurring at low m/z values in ESI-MS and APCI-MS.

However, due to the diverse array of functionalities in cellular metabolomes, progress in identifying matrices that provide broad coverage has been rate limiting. In particular, traditionally the use of MALDI-MS has been restricted to the analysis of high molecular weight metabolites because conventional matrix clusters (e.g., cyanohydroxycinnamic acid) create excessive noise in the low-mass range of the spectrum and interfere with the detection of low molecular weight cellular metabolites. Until recently, this has precluded the routine use of MALDI-MS in metabolomics. Accordingly, although, MALDI-MS offers the potential advantage of rapid throughput which, when combined with stable isotope standards for metabolites of interest that can theoretically generate large amounts of quantitative information with unprecedented speed and accuracy, previous work has failed to obtain suitable methods for the effective ionization/desorption of the multiplicity of chemical entities in biologic samples using MALDI ionization/desorption methods. Moreover, in many cases, the use of mass determination alone does not allow the identification of the relative contributions of the chemical structures that are present in an ion peak due to the large number of isomeric metabolites in biologic samples.

Matrices have now been identified, however, that produce minimal spectral noise in the low molecular weight region of interest. Examples include the silicon nanoparticle, mesotetrakis (pentafluorophenyl)porphyrin, 9-aminoacridine, porous silicon, cyanohydroxycinnamic acid, dihydroxybenzoic acid, trihydroxyacetophenone and ionic liquid matrices, all of which have been examined and their utility in specific applications confirmed. Recently, MALDI-MS, employing 9-aminoacridine (9-AA) matrix, was used to "identify" 29 metabolites by mass alone from extracts of the islets of Langerhans. However, this low number of metabolites does not represent sufficient coverage of the cellular metabolome and even the "identified" metabolites contain unknown contributions from different isomeric species. Previously, it was recognized that 9-aminoacridine may be used as a matrix since it produced only small amounts of ion clusters after laser excitation. However, this diminutive coverage, lack of reproducibility between preparations, and the errors made by not knowing isomeric content precluded its effective use in metabolomics investigations. Enabling advances that greatly expand coverage of the metabolome and provide definitive identification of isomeric molecular species through tandem mass spectrometric approaches were necessary for further progress. Thus, prior work neither recognized the vastly expanded information content that could be generated by multiplexing engineered analyte-matrix pairs nor the necessity of tandem mass spectrometry for identification of the structural assignments of isobaric peaks (i.e., peaks having identical nominal masses but not necessarily structural isomers) as well as peaks resulting from chemical isomers (i.e., isomers with exactly the same elemental composition and mass).

We theorized that the facile ability of 9-AA to undergo combinatorial changes in its stereoelectronic states, intermolecular interactions and $\pi$ stacking will promote a rich repertoire of analyte-matrix interactions to allow extended coverage into the metabolome. Without being bound by theory, we envisaged that combinatorial multiplexing of stereoelectronic interactions may be induced by alteration in charge state modulating the HOMO-LUMO (highest occupied molecular orbital-lowest unoccupied molecular orbital) interactions in the well-suited aromatic matrix 9-AA which contains a primary amine that undergoes pH-induced changes in charge state. The delocalization of electron density and charge in the 9-AA matrix facilitates the development of novel analyte/matrix interactions that can be exploited for ionization and desorption of analytes. In one aspect, these novel interactions can be envisaged to result from analyte interactions with the formal structures of three discretely charged 9-AA matrices containing delocalized electrons as shown schematically in FIG. 1.

BRIEF DESCRIPTION OF THE INVENTION

In one aspect, a method for rapid analysis of charged metabolites or metabolites that contain, or may be induced to contain, a charge through the generation of suites of analyte-matrix interactions that enable the performance of high throughput metabolomics without the use of chromatography is provided. As used herein, the "metabolite" refers to any metabolite known in the art, including, but not limited to, cellular signaling metabolites (e.g., cAMP, cGMP, IP3, eicosanoids, and combination thereof); lipid signaling metabolites (e.g., prostaglandins); metabolites involved in energy production; metabolites of intermediary metabolism; oxidized metabolites; lipid metabolites; and metabolites produced by biologic enzyme reactions as well as non-enzymatically produced chemical moieties present in biologic cells and fluids. As used herein "charge" or "charged" refers to both negatively and positively charged metabolites or metabolites that can be induced to have charge separation. The method includes inactivating endogenous enzyme activities using neutral organic solvents in conjunction with a matrix having minimal background noise (i.e., preferably at least 20-50 fold greater S/N for the lowest signals of interest, but at least 5-fold greater in the mass range of interest).

The method includes: (1) multiplexed conditions that lead to combinatorial alterations in the analyte/matrix stereoelectronic configurations that facilitate either selective energy transfer, proton transfer or ion desorption through altered matrix $\pi$ stacking, hydrogen bonding and novel analyte-matrix interactions that promote efficient ionization/desorption from the engineered analyte-matrix pairs; (2) enablement of tandem mass spectrometry of ion peaks with identical mass, or peaks close in mass (i.e., within 1-10 Thompsons), by using selective analyte-matrix pairing to edit individual peaks and identify the chemical structures corresponding to the m/z ratio of the closely neighboring ions of interest that can be spectrometrically isolated through multiplexing matrix conditions and or fragmentation energies; and (3) multiplexed combinatorial extraction and analyte/matrix conditions in conjunction with (1) to spectrometrically isolate, identify and directly quantitate complex samples through comparisons with stable isotopes of the metabolite of interest or other internal standards with similar ionization properties to the metabolites of interest. As used herein, "multiplex," "multiplexed," and "multiplexing" refer to the combinatorial analysis of matrix-analyte interactions to provide a global "fingerprint" of metabolites that can be quantitated by ratiometric comparisons with stable-isotope standards or other standards added to the extract for purposes of comparison. For example, conditions that can be multiplexed include the matrix pH, the analyte pH, solvents that the matrix and analyte are dissolved in, the matrix charge state, stereoelectronic interactions within the matrix, the use of delocalized electron distributions in aromatic matrices, alterations of laser power, changes in laser wavelength, adjuvants and the addition of guests in the matrix that modify its physical properties to facilitate selective ionization/desorption of specific classes of analytes.

In another aspect, a multiplexed MALDI-tandem mass spectrometric method for analysis of charged metabolites or metabolites that can be induced to contain a charge in mammalian tissues or biologic fluids (also referred to jointly as biologic material) is provided. The method includes extracting metabolites from a mammalian tissue through multiplexed extraction procedures providing a water-soluble component and a chloroform soluble component. Other combinations of multiplexed extraction conditions including, without limitation, chloroform, methanol, isopropanol, butanol, ethyl acetate, hexane have also been executed. A sample of the extracted metabolites in appropriate combinations of solvents is reconstituted and mixed with a set of multiplexed matrices (e.g., pH adjusted charge states of the matrix, altered electron density and electron delocalization in the matrix, matrix adjuvants) and optimized solvents. Multiplexing these combinatorial alterations produce supramolecular assemblies with novel analyte/matrix pairs that promote ionization and desorption from the matrix. Thus, through combinatorial variations of matrix stereoelectronic conformations, matrix-matrix interactions and analyte-matrix interactions metabolite classes can be effectively induced to undergo selective ionization thereby eliminating the need for prior chromatographic separation and enabling MALDI-based shotgun metabolomics. The information content from multiplexing analyte-matrix interactions can also be augmented through the use of adjuvants, such as glycerol or through inducing differential host-guest interactions by the introduction of alterations in pH, optimized mixtures of solvents, selected oxytropic ions, addition of adjuvants and alterations in ionic strength which have been demonstrated. The resultant mixture is analyzed using tandem mass spectrometry. Metabolites are identified utilizing an iterative procedure including identifying the chemical structure of the ion from either external data bases or internal accumulated data bases and confirming assignments of medium abundance (approximately 0.1-3 mol %) and high abundance (approximately at least about 3 mol %) ion peaks by MALDI-tandem mass spectrometry analyses. The spectra are recalibrated using the identified metabolites as internal standards of known mass for peak assignment and added isotopic labeled compounds as internal standards for quantitation. Structures for low abundance and extremely low abundance peaks are provisionally assigned and the identities are confirmed using MALDI-tandem mass spectrometry analysis. The pH and solvents in the matrix are varied to facilitate combinatorial stereoelectronic states possessing a repertoire of stereoelectronic interactions that lead to the formation of productive complexes facilitating energy transfer and ionization/desorption of the analyte of interest.

BRIEF DESCRIPTION OF THE DRAWINGS

In FIG. 20 panels C, and D tandem mass spectral comparisons of the fragmentation of sodiated 18:1-18:1-16:1/18:2-18:1-16:0 TAG molecular species present in mouse adipose tissue extracts were acquired by: C) MALDI-TOF/TOF MS; or D) ESI-MS in the positive ion mode. The MALDI-TOF/TOF tandem mass spectrum was recorded on a 4800 MALDI-TOF/TOF Analyzer in the positive ion mode using optimized conditions with 9-aminoacridine as matrix. Spectra were obtained with CID on, metastable suppressor on and timed ion selector enabled. The voltages of source 1, collision cell and collision cell offset were 8.0 kV, 7.0 kV and −0.035 kV, respectively. The collision gas was air at medium pressure. The tandem MS spectrum was obtained by averaging 2000 consecutive laser shots (50 shots per subspectra with 40 total subspectra). In panel D, the ESI tandem mass spectrum of the identical extract was recorded on a TSQ Quantum Ultra Plus triple-quadrupole mass spectrometer in the positive ion mode. After selection for the sodiated TAG ion in the first quadrupole, collision activation was performed in the second quadrupole with collision energy of 35 V and the resultant product ions were analyzed in the third quadrupole as described in the Experimental Section.

DETAILED DESCRIPTION OF THE INVENTION

Through exploiting multiplexed groups of new analyte-matrix stereoelectronic interactions and their ability to facilitate proton transfer/desorption in energized systems after laser irradiation, the chemical identification and quantitation (through stable isotope internal standards or ratiometric comparisons) of hundreds of metabolites from biological materials may be rapidly achieved. As used herein "biological materials" can refer to any material for a living organism, including, for example, tissues, fluids, and excretions. Furthermore, using the described methods allows for identification and quantitation without the need for chromatography, which can be a slow and inefficient process for the multiple types of metabolites with different chemical functionalities found in biologic tissues and fluids.

Figure 1A:
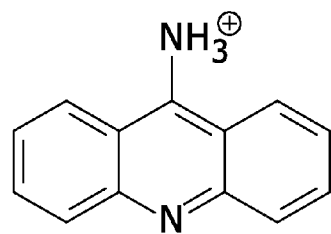
FIG. 1. Discrete 9-Aminoacridine Charge States Promote Alterations in HUMO-LUMO energy levels and promote oriented matrix stacking. The electron donating properties of the amino group in 9-aminoacridine can be manipulated by alterations in pH resulting in changes in the electronic character and stereochemical relationships of the matrix and matrix-analyte interactions that facilitate combinatorial suites of interactions that can effectively transfer energy to facilitate ionization/desorption. 9-aminoacridine is particularly well-suited to facilitate these interactions through exploiting the different nitrogen charge states that modulate electron donation/withdrawal of this group and the densities of delocalized electrons through the conjugated ring system.
Figure 1B:
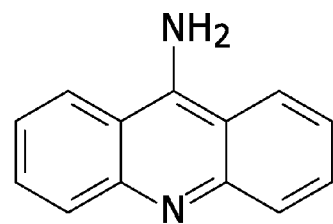
Figure 1C:
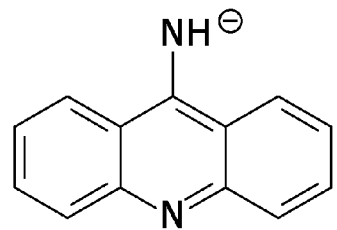

The present invention provides a method for exploiting changes in the stereoelectronic nature of differentially charged resonance forms of 9-aminoacridine (shown in FIG. 1), their differential stacking due to their π cloud interactions and the use of multiplexed combinatorial matrix-analyte interactions to provide high throughput coverage for the identification and quantitative analysis of the metabolome. By exploiting combinatorial multiplexing of stereoelectronic orbital energy levels to modulate energy and proton transfer, suites of cellular metabolites that often contain at least some similar ionizable chemical functionalities can be selectively ionized/desorbed and can be rapidly identified and quantified with unparalled speed (laser), accuracy (internal standards and high energy fragmentation to discriminate isomers) and coverage (many hundreds of metabolites to date).

The salutary properties of the 9-aminoacridine to undergo pH induced combinatorial changes in their electronic HOMO-LUMO interactions in different charge states through π stacking and multiple different matrix analyte interactions were exploited to dramatically increase coverage of the metabolome of murine myocardium using MALDI-tandem mass spectrometry. By using fragments of singly charged molecular ions through MALDI ionization with tandem mass spectrometry, we greatly extended the penetrance into the metabolome, identification of isomeric metabolites, and increased data precision. This technique permitted us to identify hundreds of metabolites from murine myocardium based on mass accuracy. In many cases, we were able to structurally identify and discriminate isomeric molecular species. The utility of this methodology in quantitative metabolomic analysis is demonstrated by the accurate quantification of five representative bioenergetic metabolites for which stable isotope-labeled internal standards were used. In further support of the technique's utility, we demonstrate its ability to identify multiple extremely low abundance metabolites important for cellular signaling in multiple physiologic and pathophysiologic states. Collectively, this work identifies the utility of MALDI-tandem mass spectrometry in conjunction with multiplexed ionization conditions as a tool to study the integrated analysis of the cellular metabolome in health and disease.

The present disclosure provides a shotgun metabolomics approach using MALDI-tandem mass spectrometry developed for the rapid analysis of cellular metabolites. This approach may also be well suited for the analysis of synthetic chemical compounds and petroleum extracts, as well as other chemical moieties (e.g., pharmaceuticals). Through the use of neutral organic solvents to inactivate endogenous enzyme activities in biologic materials (i.e., methanol/chloroform/$H_2O$ extraction), in conjunction with a matrix having minimal background noise (9-amnioacridine), a set of multiplexed conditions including changes in charge and pH, nature and hydrogen bonding potential of the solvent, alterations in electronic charge densities, addition of adjuvants and alterations in ionic strength were developed that allowed identification of many hundreds of peaks corresponding to metabolites from mouse heart extracts. Through separate examinations of the water layer and the chloroform layer in either the positive or negative ion mode using multiplexed analyte-matrix interactions, many hundreds of metabolites have been identified directly from a single biologic sample. Identification of metabolite peaks was based on mass accuracy and was confirmed by tandem mass spectrometry for many of the identified metabolite peaks. Through multiplexing ionization conditions, new suites of metabolites were ionized and spectrometric isolation of closely neighboring peaks for subsequent tandem mass spectrometric interrogation were achieved. Moreover, assignments of ions from isomeric metabolites and quantitation of their relative abundance was achieved in many cases through tandem mass spectrometry by identification of diagnostic fragment ions (e.g., discrimination of ATP from dGTP). The high sensitivity of this approach facilitated the detection of extremely low abundance metabolites including important signaling metabolites such as IP3, cAMP, cGMP, eicosanoids, and combinations thereof. Collectively, these results identify a multiplexed MALDI-tandem mass spectrometric approach for analysis of charged metabolites in mammalian tissues.

Experimental Section

Reagents. 9-Aminoacridine, ATP, ADP, AMP, dGTP, dGDP, dGMP, sodium pyruvate-$^{13}C_1$, succinic acid-$d_4$, and ATP-$^{13}C_{10}$,$^{15}N_5$ were purchased from Sigma-Aldrich (St Louis, Mo.). Sodium lactate-3C and acetyl-CoA-3C were purchased from Cambridge Isotope Laboratories (Andover, Mass.). All solvents used in extraction and MS analysis were purchased from Burdick & Jackson (Muskegon, Mich.).

Methanol/Chloroform/$H_2O$ Extraction (M/C/H). Metabolite extraction was performed according to the method of Le Belle et al. with some modifications. Due to the rapid change in myocardial metabolites during anesthesia with asphyxiation, adult C57BL/6 mice were sacrificed by decapitation using a protocol approved by the Washington University Animal Studies committee. The whole excised heart was freeze-clamped at the temperature of liquid nitrogen. This method of sacrificing animals as well as the rapidity of excising and freezing the hearts is crucial to maintaining metabolite levels at their in vivo concentrations. Myocardial wafers were pulverized into a fine powder using a BioPulverizer (BioSpec Products, Bartlesville, Okla.). Next, a frozen myocardial powder sample (~20 mg) was weighed prior to homogenization in 450 μL of ice-cooled 1:2 (v/v) chloroform/methanol for 2 min at −10° C. (ethanol-ice bath) followed by the addition of a mixture of stable isotope-labeled internal standards containing acetyl-CoA-$^{13}C_2$, (0.04 nmol/mg of wet weight), ATP-$^{13}C_{10}$,$^{15}N_5$ (4 nmol/mg of wet weight), AMP-$^{13}C_{10}$,$^{15}N_5$ (0.1 nmol/mg of wet weight), succinic acid-$d_4$ (1.2 nmol/mg of wet weight), lactate-$^{13}C$ (10 nmol/mg of wet weight), and pyruvate-$^{13}C$ (3 nmol/mg of wet weight). Following the addition of 150 μL of ice-cooled water and 150 μL ice-cooled chloroform to the homogenized tissue, another homogenization was performed for 2 min at −10° C. After incubation for 30 min on ice, the homogenate was centrifuged at 25000 g for 15 mm at 4° C. The upper layer was saved on ice, and the chloroform layer was dried under nitrogen and resuspended in either chloroform/methanol or acetonitrile/isopropanol as indicated. For water soluble metabolites, the residues were subjected to re-extraction twice with 300 μL of ice-cooled 1:2 (v/v) chloroform/methanol and 100 μL of ice-cooled water and 100 μL ice-cooled chloroform following the same procedure as above. The resultant three upper layers were pooled together for MALDI-tandem mass spectrometric analysis immediately or stored at −20° C. until being analyzed. For metabolites in the chloroform phase, mass spectrometric interrogation by MALDI time of flight/time of flight mass spectrometry in either the positive or negative ion modes using multiplexed stereoelectronic interactions with 9-aminoacridine as matrix was employed.

Perchloric Acid Extraction. Metabolite extraction was carried out according to the method of Williamson and Corkey with some modifications. In brief, 250 μL of ice-cooled 3.5% perchloric acid (PCA) −20% ethanol −8 mM EDTA and an internal standard mixture containing acetyl-CoA-$^{13}C_2$ (0.04 nmol/mg of wet weight), ATP-$^{13}C_{10}$,$^{15}N$, (4 nmol/mg of wet weight), succinic acid-$d_4$ (1.2 nmol/mg of wet weight), lactate-$^{13}C$ (10 nmol/mg of wet weight), and pyruvate-$^{13}C$ (3 nmol/mg of wet weight) were added to 20 mg of frozen heart tissue and the resultant mixture was then homogenized at −10° C. for 2 min. After incubation for 30 min on ice, the homogenates were centrifuged at 25000 g for 10 min at 4° C. The resultant supernatant was saved on ice. The residues were subjected to re-extraction with 3.5% PCA-8 mM EDTA following the same procedure as above. The resultant two supernatants were pooled together and adjusted to pH 4.5 with 3 M $KHCO_3$ to precipitate $KClO_4$. After centrifugation for 10 min at 4° C., the resultant supernatant was saved on ice for MALDI-tandem mass spectrometric analysis.

MALDI-Tandem Mass Spectrometric Analysis of Water Soluble Metabolites. Three 100-μL aliquots of the murine heart extract were dried under a nitrogen stream and reconstituted in 100 μL of 0.05% TFA, water, and 2% ammonium hydroxide, respectively. After mixing 10 μL of reconstituted sample with 10 μL of 9-aminoacridine that was dissolved in 0.1% TFA-acetone, acetone, or 2% ammonium hydroxide-acetone (10 mg/mL), 1 μL of the mixture was spotted on an Opti-TOF 384-well plate. MS analysis was performed on an ABI 4800 MALDI-tandem mass spectrometer. Prior to MS analysis, calibration in the reflectron mode was performed using a mixture of standard metabolites containing malate, AMP, ATP, and acetyl-CoA, and the resultant parameters were saved as the default calibration. Staple isotope labeled cAMP was prepared by using adenylate cyclase (Sigma) in conjunction with staple isotope labeled ATP. Mass spectra were typically acquired in the negative ion mode or, in some cases, in the positive ion mode, for analysis of positively charged metabolites from the extracted tissue. For quantitation of metabolites with molecular masses greater than 130 dalton (Da), the mass spectrum was recorded in the MS reflectron mode. For quantitation of metabolites with molecular masses less than 130 Da, mass spectra were obtained in the linear mode and were calibrated using mixtures of lactate and succinate. Mass spectra for metabolite analyses were obtained by averaging 1500 consecutive laser shots (50 shots per subspectra and 30 subspectra) with default calibration. $MS^2$ analysis of metabolites was accomplished by turning on collision-induced dissociation (CID) gas and metastable suppression in the negative ion mode. Air was used for CID at a medium pressure. Ion peaks with S/N of greater than 10 were considered to be potential deprotonated metabolite signals except for peak clusters that derive from the matrix or chloride adducts, which were distinguished by pairs with a mass difference of 2 Da possessing an intensity ratio of 3:1.

Data Analysis. Monoisotopic peak area was determined using software provided by the manufacturer (version 4.5 software; Applied Biosystems). When $^{13}C_1$- or $^{13}C_2$-labeled metabolites were used as the internal standards, the internal standard monoisotopic peak area was corrected by subtracting the contribution of the isotopic peak from its corresponding metabolite. The ratio of the metabolite monoisotopic peak area to its corrected internal standard peak area was calculated using Microsoft Excel. To facilitate metabolite database searching, we constructed a metabolite database based on exact mass data released at website http://dbk.ch.umist.ac.uk/ExactMasses.htm. An Excel-based program was used to search this database. METLIN (http://metlin.scripps.edu), KEGG, and the Human Metabolome Database MS search (http://www.hmdb.ca/labm/jsp/mlims/MSDbParent.jsp) were also employed to confirm and extend search results.

The identification of extracted metabolites was accomplished through an iterative procedure that involved identification of the [M-H]$^-$ ion from the data base with a mass error of less than 0.01 Da followed by confirmation of the assignments of medium- and high-abundance ion peaks by tandem MS analyses. Next, the spectra were recalibrated using the identified metabolites as internal standards of known mass for peak assignment and added isotopic labeled compounds as internal standards for quantitation. Additional assignments for extremely low abundance peaks were made and followed by confirmation by tandem MS analysis to confirm the assignments. Next, the pH of the matrix was varied from a pH of approximately 3.0 to approximately 10, changing the metabolites that ionized effectively and permitting multiplexed sample analysis. For some low abundance extremely low molecular weight metabolites, which possessed irregular peak shapes whose peak intensities or shapes could not be improved by varying pH, and for which tandem MS analyses failed, we assigned identities by lowering mass accuracy to ±0.1 Da and verifying their identity as peaks with S/N greater than 10 visually.

RESULTS AND DISCUSSION

Figure 2A:
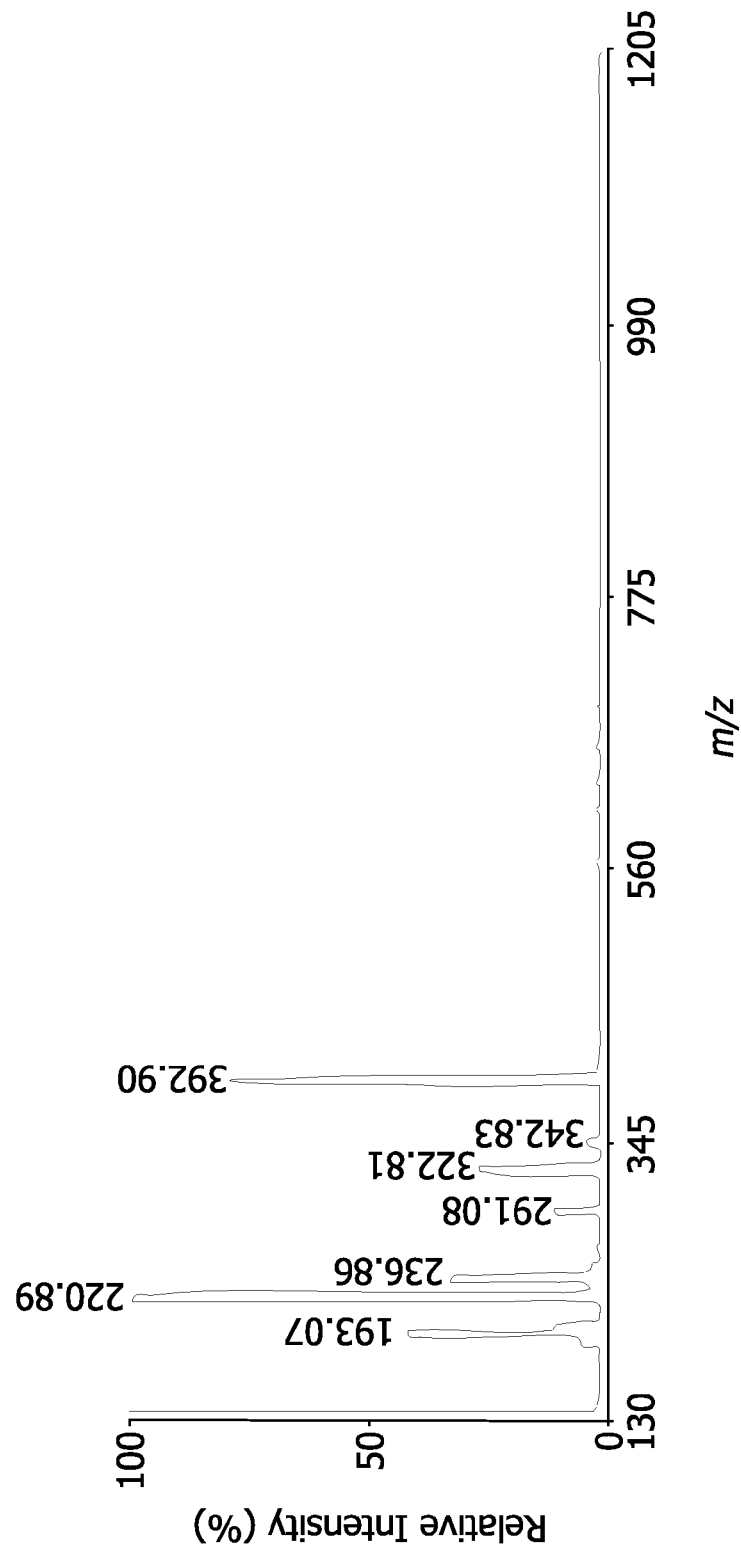
FIG. 2. Mass spectra of the water-soluble metabolites extracted from mouse heart tissue. Mass spectra were obtained by analyzing the extract of 20 mg of C57BL/6 male mouse heart tissue on 4800 MALDI-TOF/TOF Analyzer in the negative ion mode using 9-aminoacridine as matrix. (A) Metabolites were extracted using a perchloric acid extraction method as described in the Experimental Section, and the mass spectrum was recorded under neutral condition (sample pH was 7.0 and matrix solvent was acetone); and (B) metabolites were extracted using M/C/H extraction method as described in the Experimental Section, and the mass spectrum was recorded under weak acidic condition (sample pH was 3.0 and matrix solvent was acetone); (C) a magnification of the mass spectrum of metabolites extracted using the M/C/H extraction method, and the mass spectrum was recorded under weak acidic condition, showing the detection of cAMP; and (D) a magnification of mass spectrum of metabolites extracted using the M/C/H extraction method and mass spectrum was recorded under weak acidic condition, showing the detection of NADH. Individual mass spectrum of metabolites was obtained by averaging 1500 consecutive laser shots (50 shots per subspectra and 30 subspectra). The cluster around m/z 193.05 represents matrix peaks in both (A) and (B).

Detection of Metabolites. To develop a shotgun metabolomics method suitable for the rapid analysis of metabolites in mammalian tissues by MALDI-tandem mass spectrometry, the initial goal was to identify a method for tissue metabolite extraction that would be compatible with MALDI-tandem mass spectrometric analyses. In pursuit of this, two conventional extraction methods were compared. First, perchloric acid extracts of murine myocardium were mixed with a 9-aminoacridine matrix and examined by MALDI-tandem mass spectrometry under neutral conditions (i.e., pH is 7.0; matrix solvent is acetone) (FIG. 2(A)). Search of the metabolomic database did not reveal any peaks corresponding to known metabolite masses. This result indicates that the majority of peaks identified by this extraction method likely result from anion and matrix adducts and that target metabolite ionization was suppressed by the abundance of anions present in the extract. Although perchloric acid extraction is a method widely used to isolate water-soluble metabolites from tissue, and the resultant metabolites have been successfully analyzed by enzymatic fluorescence assays, NMR, LC, GC, and CE-MS (reviewed in references 12 and 36-38), in our hands, this procedure completely suppressed the formation of informative ions of cellular metabolites using MALDI ionization (FIG. 2(A)).

In sharp contrast, MALDI-mass spectra of methanol/chloroform/water (M/C/H) extracts under an acidic pH of about 3.0 (matrix solvent still being acetone) of murine myocardium demonstrated an entirely different set of peaks, which after database searching identified 285 peaks corresponding to murine myocardial metabolites. The M/C/H extraction method resulted in the relatively straightforward detection of multiple cellular metabolites (FIG. 2(B)). It exploits the ability of methanol to denature enzymes leading to their presence at the chloroform/water interface and the removal of lipids in the chloroform phase where they cannot suppress endogenous metabolite ionization. The cellular lipidome from each sample can be simultaneously analyzed by using the chloroform layer and subsequent MALDI tandem mass spectrometry using multiplexed combinations of 9-aminoacridine and adjuvants to facilitate ionization and metabolite identification by tandem mass spectrometry. Thus, a single extraction protocol permits assessment of many hundreds of metabolites directly from extracts of biologic tissues or fluids. Le Belle et al. compared perchloric acid extraction versus M/C/H extraction for NMR using brain tissue. In those studies, M/C/H extraction was far more efficient and less variable than perchloric acid extraction as assessed by NMR spectroscopy. More importantly, M/C/H extraction does not destroy acid-labile metabolites such as NADH and thus permits assessment of acid-labile metabolites. As shown in FIG. 2(D), NADH was extracted from murine myocardium by M/C/H extraction and was readily detected by MALDI-tandem mass spectrometry. Due to the clear advantages of the M/C/H extraction method for use in MALDI-tandem mass spectrometry this method was employed in all subsequent experiments. Moreover, the use of this extraction procedure allowed the simultaneous preparation of samples for hydrophobic metabolite analysis.

Both low molecular weight and low-abundance metabolites were easily detected using MALDI-tandem mass spectrometry with 9-aminoacridine as matrix in the negative ion mode. For example, the ubiquitous second messenger cAMP (m/z 328.04) was easily detected (FIG. 2(C), which shows a magnification of the mass spectrum of metabolites extracted using the M/C/H extraction method, and the mass spectrum was recorded under weak acidic condition, showing the detection of cAMP) and could be readily discriminated from other isomeric species by tandem mass spectrometry (see Metabolomic Analysis of Mouse Tissue Extract below). In control experiments using MALDI tandem mass spectrometry analysis with 9-aminoacridine, in the absence of tissue extract no substantial peaks were detected, with the exception of an ion cluster at m/z 193-195. Collectively, these results demonstrate that MALDI-TOF MS using 9-aminoacridine is a suitable method for direct and deep penetrance into the low-abundance range of negatively charged metabolites by MALDI-tandem mass spectrometry.

pH-Dependent Ionization of Metabolites in Mouse Heart Extracts. Ionization of metabolites using MALDI largely relies on the complex interactions of photons with matter and the resultant ability of the metabolite to gain or lose a proton and desorb from the matrix which in turn is a function of the metabolite's chemical structure, its stereoelectronic interactions with the matrix, and the number of productive complexes present in the matrix. Without being bound by theory, the presence of the differential charge on the highly aromatic aminoacridine structure provides an effective way to combinatorially increase the array of HOMO-LUMO interactions to energetically interact with photons during irradiation. The multiplexed set of orbitals, charge states and $\pi$ stacking interactions will facilitate energy transfer as well as facilitate proton transfer. The different charge states with electron enrichment (alkaline), electron withdrawal (positive charge) or neutral induced by the different pH conditions provides a combinatorial set of interactions that can lead to effective energy transfer and proton transfer. Moreover, the differential $\pi$ stacking in these different matrix compositions (compositions 1, 2, and 3 in FIG. 1) and/or other analyte-matrix stereoelectronic interactions facilitated by combinatorial interactions with analytes allowing deep penetrance into complex mixtures of differing functionalities. Accordingly, metabolites with different structures show remarkable variability in their ionization efficiencies as a function of different electronic states and interactions after changing pH of the aromatic heavily conjugated 9-aminoacridine matrix. To explore the possibility that altering pH might result in enhanced ionization of a new suite of metabolites, we examined MALDI-TOF MS spectra of tissue samples acquired by altering both matrix and sample pH values.

Figure 3A:
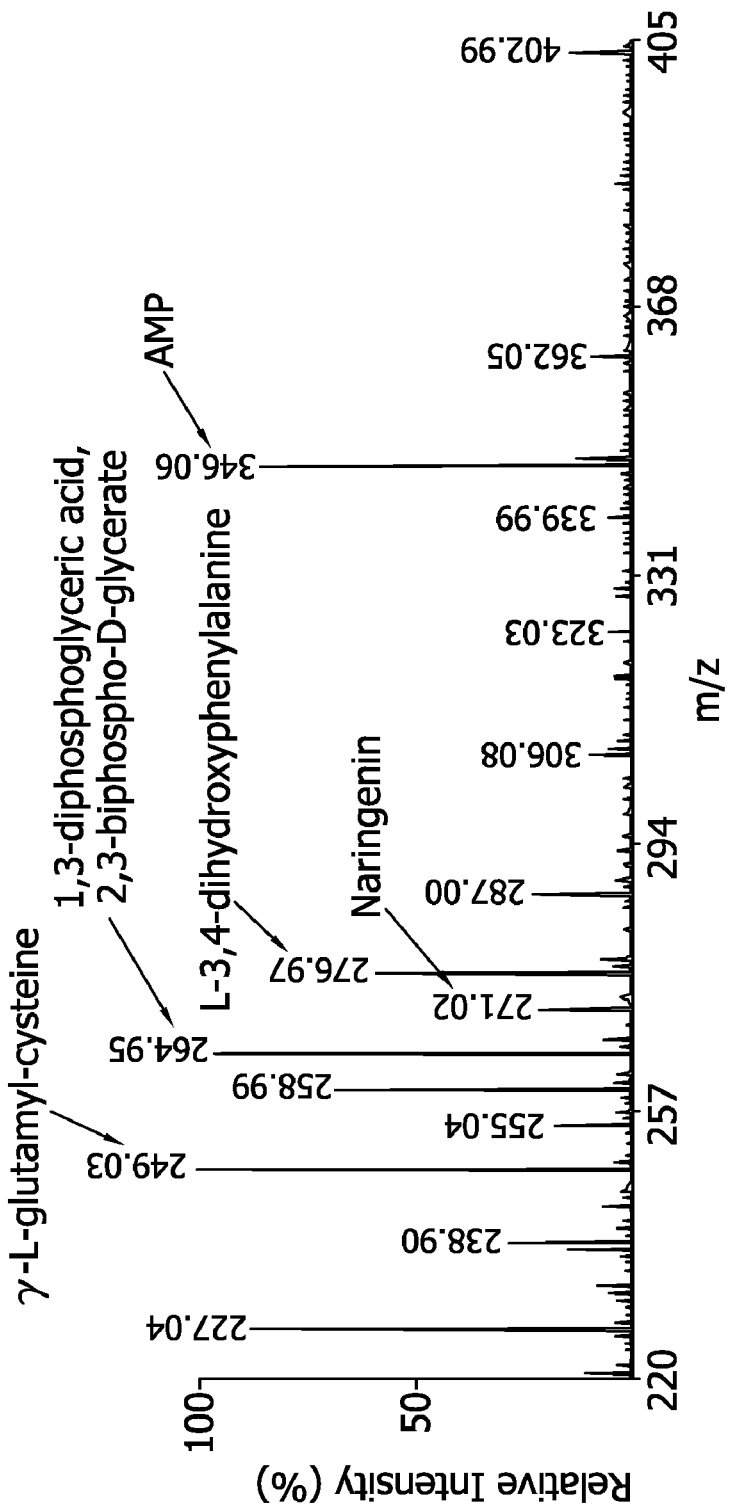
FIG. 3. Expanded mass spectra of the water-soluble metabolites extracted from mouse heart tissue. Mass spectra were acquired on a 4800 MALDI-TOF/TOF Analyzer in the negative ion mode using 9-aminoacridine as matrix under (A) acidic condition (sample pH was 3.0 and matrix solvent was 0.1% TFA-acetone), (B) neutral condition (sample pH was 7.0 and matrix solvent was acetone), and (C) basic condition (sample pH was 10.0 and matrix solvent was 2% ammonium hydroxide-acetone). Metabolites were extracted using the M/C/H extraction method. Individual mass spectrum of metabolites was obtained by averaging 1500 consecutive laser shots (50 shots per subspectra and 30 subspectra).
Figure 3B:
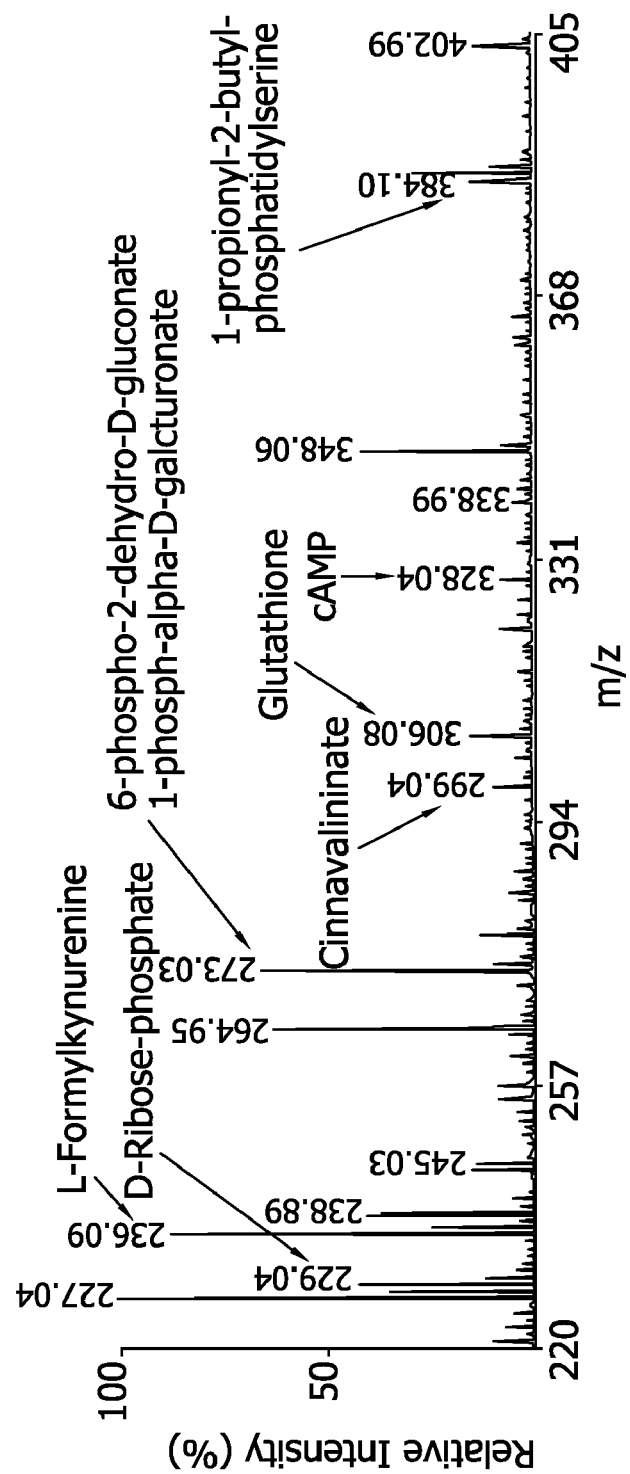
Figure 3C:
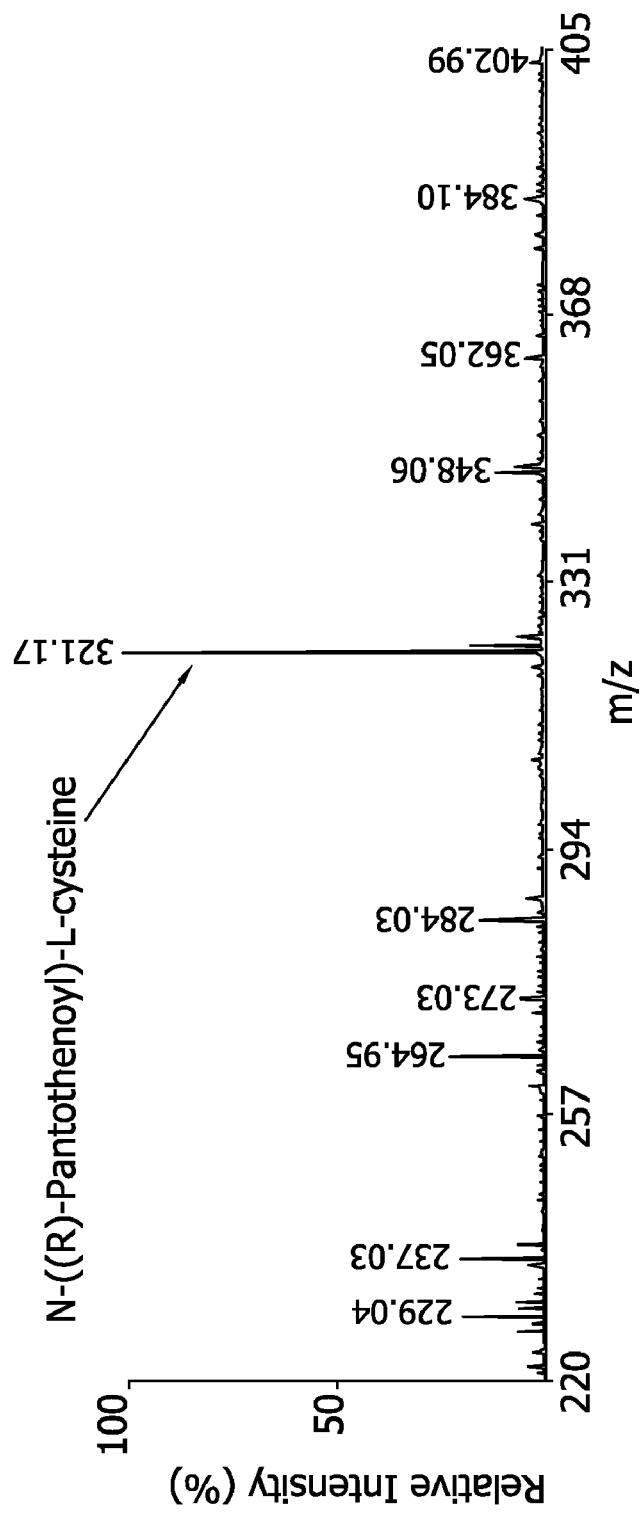

As shown in FIG. 3(A-C), three different mass profiles were obtained when sample pH was varied from 3.0 (acidic pH) (FIG. 3(A)) to 7.0 (neutral condition) (FIG. 3(B)) to 10.0 (basic pH) (FIG. 3(C)) and mass spectra were recorded using 0.1% TFA-acetone, acetone, and 2% ammonium hydroxide-acetone solution as matrix solvent, respectively. FIG. 3 demonstrates that, as predicted, some metabolites can be ionized only under certain pH conditions. For example, the metabolites at m/z 249.03 (y-L-glutamylcysteine) and 275.97 (L-3, 4-dihydroxyphenylalanine sulfate) were ionized only under acidic conditions (sample pH was 3.0 and matrix solvent was 0.1% TFA-acetone), yielding poor signal at both neutral and basic pHs (sample pH of 7.0 and matrix solvent was acetone and sample pH of 10.0 and matrix solvent was 2% ammonium hydroxide-acetone, respectively). Similarly, the metabolites at m/z 236.09 (Biopterin) and 299.04 (cinnavalininate) were ionized only under neutral conditions, and the metabolite at m/z 321.17 (N-((R)-pantothenoyl)-L-cysteine) was ionized only under basic conditions. Additionally, although some metabolites can be ionized under two or all three conditions, the efficiency of ionization varied significantly at different pHs. For example, ionization efficiency was much greater for the metabolites at m/z 346.06 (AMP), 271.02 (naringenin), and 264.95 (1,3-diphosphoglyceric acid or 2,3-biphospho-D-glycerate) under acidic conditions, and for the metabolites at m/z 384.10 (phosphatidylserine), 328.04 (3',5'-cylic adenosine phosphate (cAMP)), 306.08 (glutathione), and 229.04 (D-ribose-phosphate) under neutral conditions. In an effort to further improve signal, we observed that varying matrix pH but keeping sample pH constant can alter ionized metabolite profiles. The mass profiles were completely changed when murine myocardial extract at pH 7.0 was mixed with matrix in solutions at three different pHs: 0.1% TFA-acetone, acetone and 2% ammonium hydroxide-acetone. Extensive analyses of murine myocardial extract with pH values of 3.0 or 10.0 mixed with matrix in solutions of three different pHs also demonstrated remarkable alterations in metabolite profiles (data not shown). Since MALDI-TOF MS analysis of metabolites using 9-aminoacridine as matrix is normally performed under neutral conditions, multiplexing ionization conditions provides a novel means to enhance penetrance into the metabolome, to improve S/N of metabolites present in low abundance, to provide an enhanced and enriched signal for tandem mass spectrometric interrogation of peaks with very similar m/z values, and to identify the relative isomeric composition of ion peaks corresponding to multiple isomeric compounds.

Metabolite ionization in the negative ion mode is typically enhanced by the presence of the conjugate base of phosphate and carboxylate functional groups. Varying pH values could change the charge state of these specific groups, leading to alterations in the ionization efficiency of metabolites containing these functional groups. Examination of detected metabolites (discussed below) identified that some metabolites containing multiple phosphates were ionized ideally under acidic or neutral conditions in the negative ion mode (FIG. 4(A-B)) and that ionization efficiency as a singly charged ion decreased with increasing pH due to an increased prevalence of compounds with multiple negative charges. In contrast, for some monocarboxylate-containing metabolites, an increase in pH improved ionization in the negative ion mode due to increased deprotonation of these metabolites under our experimental conditions. However, as for some of the multiple phosphate-containing metabolites, increasing pH did substantially improve ionization at the highest pH value employed (i.e., pH 10) which can be exploited for spectrometric isolation of neighboring peaks for tandem mass spectrometry in many cases. Collectively, these examples underscore the potential for increased penetrance into the metabolome and improved metabolite discrimination through use of an appropriate set of multiplexed conditions during examination of metabolomes of interest. They also underscore the importance of using appropriate stable isotope standards for precise quantitation of metabolites through a MALDI approach due to the differential ionization sensitivities and properties of the observed metabolites.

Figure 4A:
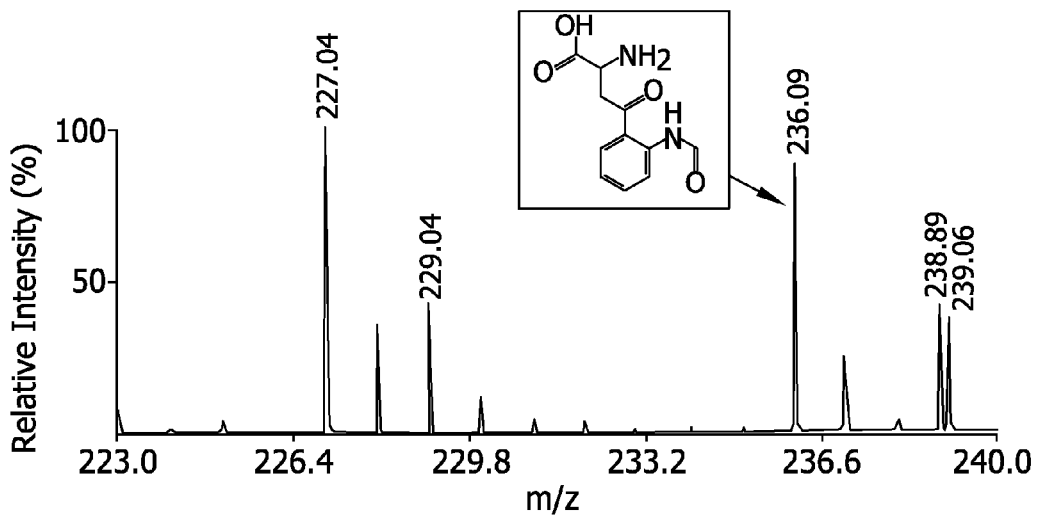
FIG. 4. Expanded mass spectra of the water-soluble metabolites extracted from mouse heart tissue. Mass spectra were acquired on a 4800 MALDI-TOF/TOF Analyzer in the negative ion mode using 9-aminoacridine as matrix under (A) neutral condition (sample pH was 7.0 and matrix solvent was acetone), (B) basic condition (sample pH was 10.0 and matrix solvent was 2% ammonium hydroxide-acetone), and (C) the sample pH was 7.0 and while the matrix pH was approximately pH 3.0 with 0.1% TFA-acetone being used as matrix solvent. Metabolites were extracted using the M/C/H extraction method. Individual mass spectrum of metabolites was obtained by averaging 1500 consecutive laser shots (50 shots per subspectra and 30 subspectra).
Figure 4B:
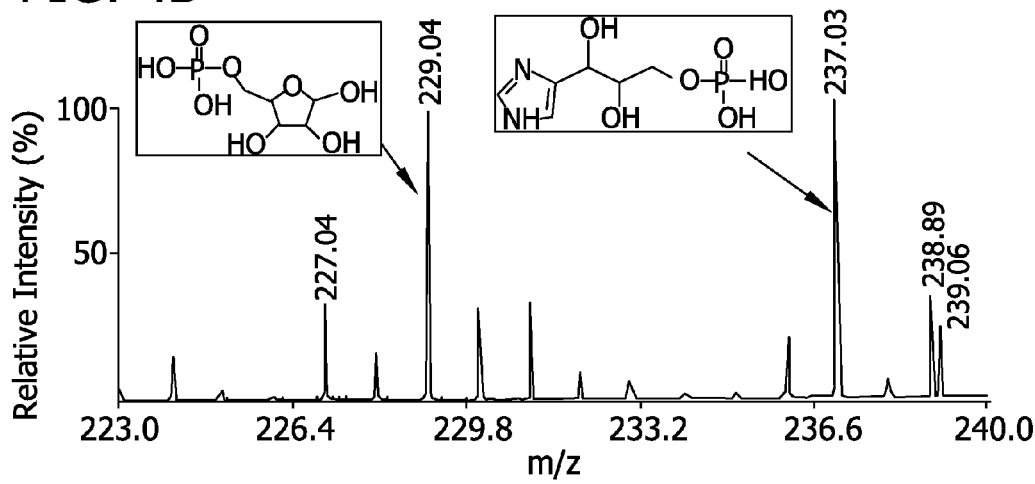
Figure 4C:
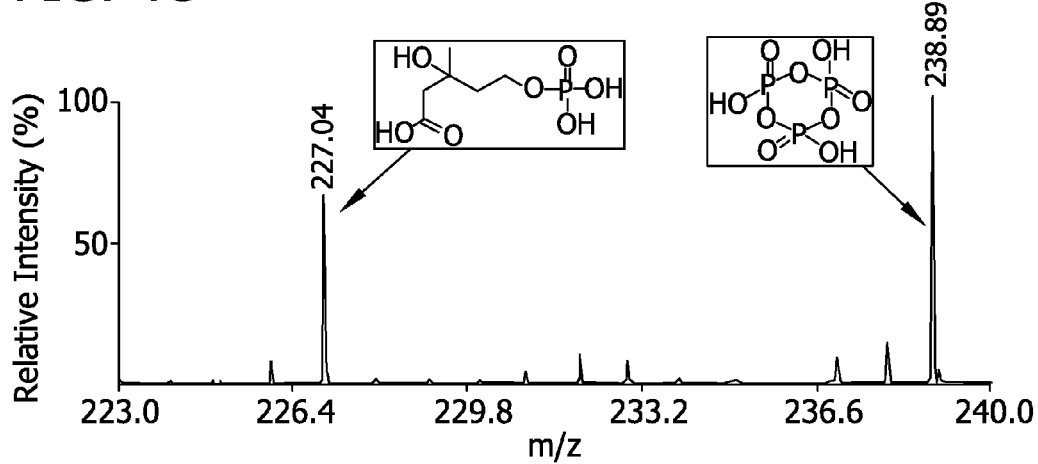

Multiple pH Conditions for Selective Tandem MS Analysis. The use of a narrow mass window is important for successful tandem MS analysis of metabolites of similar mass by MALDI-tandem mass spectrometry. Of course signal intensity is typically inversely proportional to the mass window utilized. Thus, care must be taken during tandem mass spectrometric fragmentation of low-abundance ions of similar molecular mass to ensure that fragmentation ions are assigned to the appropriate ion peak. The normal mass window setting is typically at least 3-10 Thompsons when low-abundance peaks are subjected to tandem MS analysis, to maximize information in the resultant high-energy fragmentation spectrum. Without prior chromatographic separation, however, ion peaks representing multiple low molecular weight metabolites are often crowded in the low molecular weight region, complicating interpretation of MS/MS spectra, and often rendering interpretation an intractable problem. A strategy for selective tandem MS analysis of low-abundance metabolites that did not subject the sample to uncertainties of the chromatographic procedure employed was developed. Through exploiting the differential ionization propensities of different cellular metabolites, substantial degrees of peak selection were achieved. As shown in FIG. 4(A), tandem MS analyses of metabolites at m/z 238.89 representing trimetaphosphate was not practical under neutral conditions (sample pH of 7.0 and matrix solvent was acetone) due to the presence of a neighboring peak at m/z 239.06 with similar intensity within the selectivity window. Narrowing the selectivity window reduced S/N to unusable levels. However, as shown in FIG. 4(C), adjustment of matrix pH to an acidic condition completely suppressed the ion peak at m/z 239.06 and permitted successful tandem MS structural identification of trimetaphosphate. Similarly, tandem mass analyses of metabolites at m/z 229.04 and 237.03 representing ribose-5-phosphate and D-erythro-1-(imidazol-4-yl)glycerol 3-phosphate failed at acidic and neutral conditions (FIG. 4 (A-B), but could be achieved using basic conditions by analyte/matrix selective editing.

Applying these combinatorial changes to matrix stereoelectronic relationships and analyte interactions for tandem MS analysis of medium-abundance ion peaks with intense neighboring ion peaks led to great success. For example, the ion peak at m/z 227.04 representing (R)5-phosphomevalonate had two intense neighboring ion peaks of m/z 229.04 and 228.04 under neutral conditions (FIG. 4(A)). The tandem MS analysis of this compound was significantly affected by these neighboring peaks as the limits of the ion selection window did not allow complete 1-Da discrimination during MALDI-tandem mass spectrometry. Changing the matrix conditions from acetone to 2% ammonium hydroxide-acetone completely suppressed the ion peaks at m/z 229.04 and 228.04 enabling tandem ion mass spectrometric isolation and analysis of the peak at m/z 227.04. Thus, comparing the fragment ion intensities at each of two pHs facilitated the accrual of highly accurate fragmentation patterns without contamination of neighboring peaks even below the limits of the instrument's selectivity window.

Identification of Metabolites Extracted from Mouse Heart Tissue. Part of the power of MALDI-tandem mass spectrometry for metabolomics analysis is that it can elucidate the chemical structure of multiple isomeric molecular species that occur in the metabolome. This utilization of tandem MS both increases confidence in metabolite identification and permits the identification of underlying and, perhaps, unanticipated chemical isomers. We used tandem MS analysis, in conjunction with mass accuracy (as described in the Experimental Section), to unequivocally identify 90 metabolites in murine heart extracts. A total of 187 additional metabolite peaks were identified based solely on molecular mass because tandem mass spectrometry was not successful either due to the fact that they were present in low abundance, because they were inefficiently ionized, or they could not be effectively fragmented.

Quantitation by MALDI requires comparisons with stable isotope counterparts of the compounds of interest. In some cases, an alternative is to use stable isotopes of representative moieties containing similar functionalities so that ratiometric comparisons to exogenous standards can be profiled. Fewer than 50 peaks have not been assigned, which may represent unknown metabolites, intrasource fragmentation products of known metabolites, or matrix adducts of metabolites.

Figure 5A:
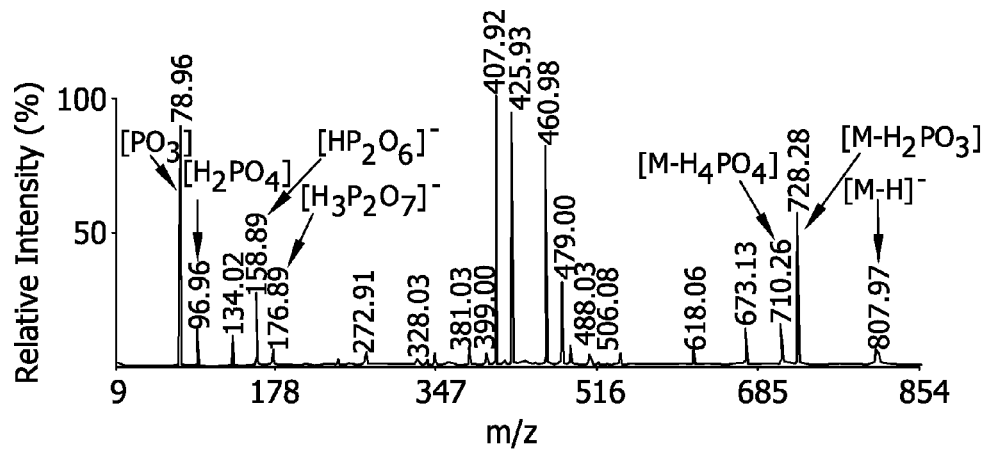
FIG. 5. Comparison of tandem MS spectra of authentic acetyl-CoA and the ion at m/z 808.12 present in mouse heart extracts. The tandem MS spectra of (A) standard acetyl-CoA and (B) metabolite from mouse heart extract with ion peak at m/z 808.12 were acquired using a 4800 MALDI-TOF/TOF Analyzer in the negative ion mode using 9-aminoacridine as matrix with CID on, metastable suppressor on, and timed ion selector enabled. The voltages of source 1, collision cell, and collision cell off set were 8.0, 7.0, and −0.035 kV, respectively. The collision gas was air at medium pressure. The tandem MS spectrum was obtained by averaging 2000 consecutive laser shots (50 shots per subspectra and 40 subspectra). The chemical structure of acetyl-CoA, panel C demonstrates the assignments of major peaks on tandem MS spectra A and B. The similarity of spectra A and B assigns the metabolite with ion peak at m/z 808.12 to be acetyl-CoA.
Figure 5B:
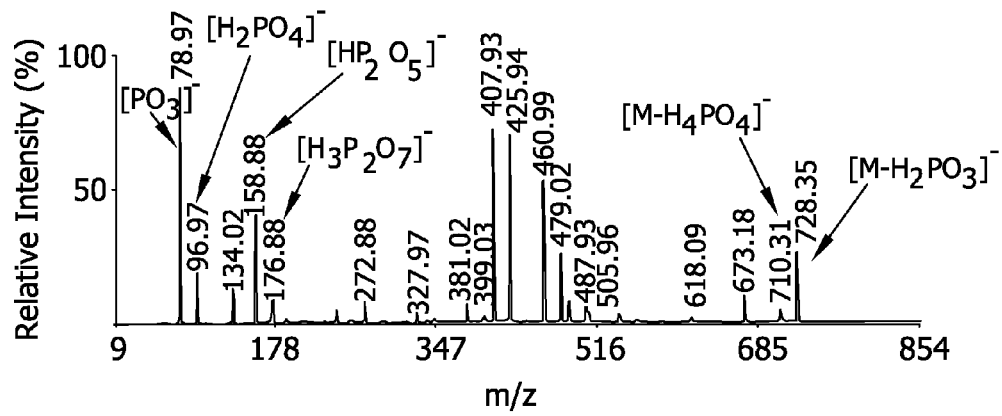
Figure 5C:
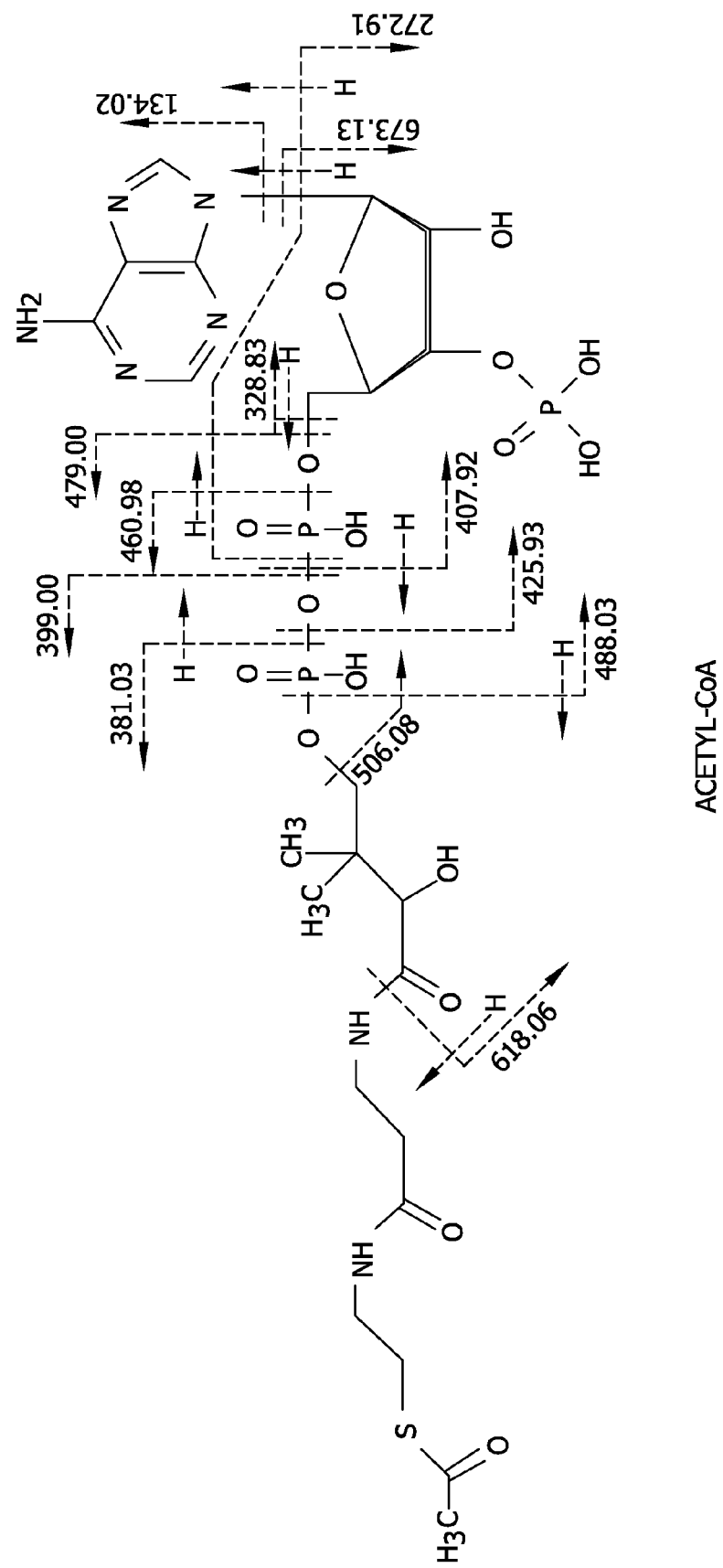

In total, 56% of detected metabolites contained phosphate groups, while carboxylate-containing metabolites accounted for 37%. These results identify the suitability of negative ion MALDI MS for identification of both the readily ionized phosphate-containing metabolites and for the carboxylate functionality. Importantly, 40 metabolites' peaks were identified as CoA and its derivatives. FIG. 5(A-B) show a comparison of the tandem MS spectrum of a typical CoA-containing metabolite, acetyl-CoA, at m/z 808.12 present in mouse heart extracts. Specifically, the tandem MS spectra of (FIG. 5(A)) standard acetyl-CoA and (FIG. 5(B)) metabolite from mouse heart extract with ion peak at m/z 808.12 were acquired using a 4800 MALDI-TOF analyzer in the negative ion mode using 9-aminoacridine as matrix with CID on, metastable suppressor on, and timed ion selector enabled. The voltages of source 1, collision cell, and collision cell off set were 8.0, 7.0, and −0.035 kV, respectively. The collision gas was air at medium pressure. The tandem MS spectrum was obtained by averaging 2000 consecutive laser shots (50 shots per subspectra and 40 subspectra). The chemical structure of acetyl-CoA at the bottom demonstrates the assignments of major peaks on tandem MS spectra A and B. The similarity of spectra A and B assigns the metabolite with ion peak at m/z 808.12 to be acetyl-CoA.

The presence of the mass accuracy and a fragmentation pattern similar to that of authentic acetyl-CoA confirms the identity of this peak as acetyl-CoA. Acetyl-CoA and its esters play important roles in regulating intermediary metabolism. For example, alterations in the free CoA concentrations have been proposed to be primary regulators of metabolic flux. Similarly, alterations in acyl-CoA levels have been implicated as pathologic mediators of dysfunctional metabolism in several disease states including diabetes and ischemia. Each of the 11 intermediates in the tricarboxylic acid (TCA) cycle was detected. The ability to analyze TCA cycle intermediates after addition of stable isotope standards without the need for prior derivatization or chromatographic separation should facilitate interrogation of the metabolome. In addition, we detected low-abundance intracellular second messengers including cAMP, cyclic guanosine phosphate (cGMP), cylic adenosine diphosphate ribose, and inositol 1,4,5-triphosphate (IP3). By detecting variations in these metabolites through comparisons with stable isotope standards, this shotgun metabolomics approach can be used to monitor the state of cellular signal transduction processes in cells or tissues of interest.

Assignment of Isomeric Ion Peaks and Quantitative Analysis of Molar Ratios of Isomers by Tandem Mass Spectrometry. Metabolite extracts from biological sources are very complex and usually contain many groups of compounds with isomeric masses. Assignment of an identity to an ion peak containing multiple isomers (isomeric ion peak) is often quite difficult, even if tandem MS analysis is performed. Such isomeric ion peaks, by definition, represent mixtures of multiple isomers and will inevitably produce tandem MS spectra that may be difficult or impossible to interpret. Additionally, the determination of the molar ratio of isomers in a complex mixture requires further interrogation such as tandem MS. In this study, we use MALDI-tandem mass spectrometry to identify diagnostic fragment ions whose ratio can be used to assign the identity and distribution of isomers in complex mixtures.

Figure 6A:
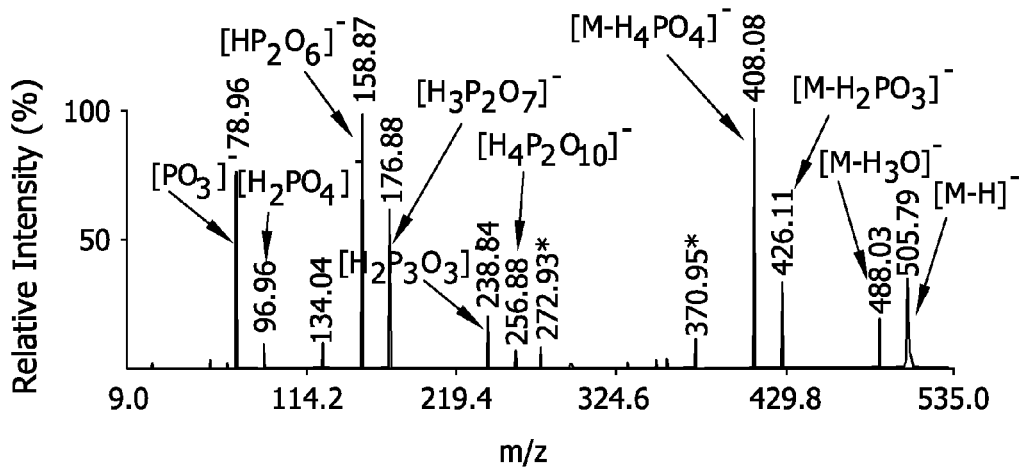
FIG. 6. Comparison of tandem MS spectra of authentic ATP, authentic dGTP, and the ion at m/z 505.99 present in mouse heart extracts. The tandem MS spectra of (A) authentic ATP, (B) authentic dGTP, and (C) mouse heart extract with an ion peak at m/z 505.99 were recorded on a 4800 MALDI-TOF/TOF Analyzer in MS-MS negative ion mode using 9-aminoacridine as matrix with CID on, metastable suppressor on, and timed ion selector enabled. The voltages of source 1, collision cell, and collision cell off set were 8.0, 7.0, and −0.035 kV, respectively. The collision gas was air at medium pressure. The tandem MS spectrum was obtained by averaging 2000 consecutive laser shots (50 shots per subspectra and 40 subspectra). The chemical structures ATP and dGTP show the assignments of their signature peaks (D). Tandem MS spectrum of metabolite with ion peak at m/z 505.98 identifies the fragment of adenosine group at m/z 134.04 as an adenosine group, not a guanosine group at m/z 150.01, assigning this metabolite to be ATP, not dGTP.
Figure 6B:
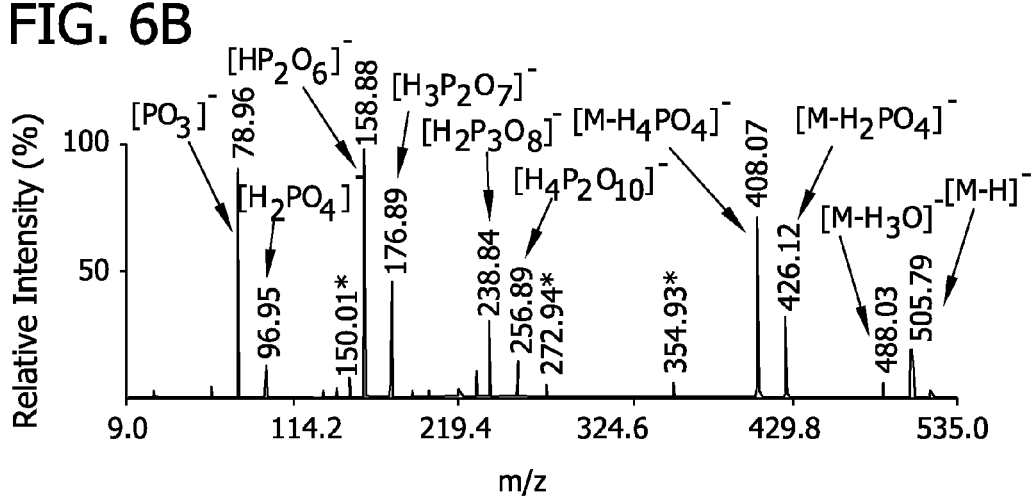
Figure 6C:
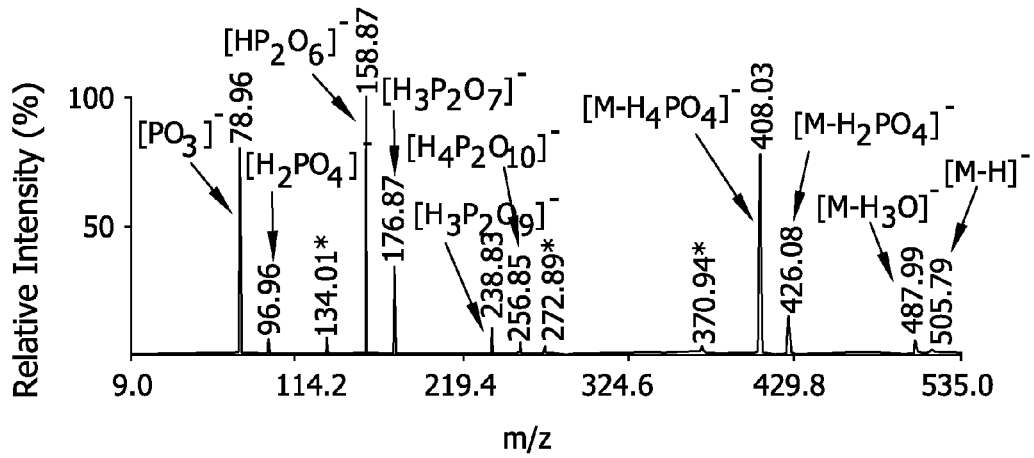
Figure 6D:
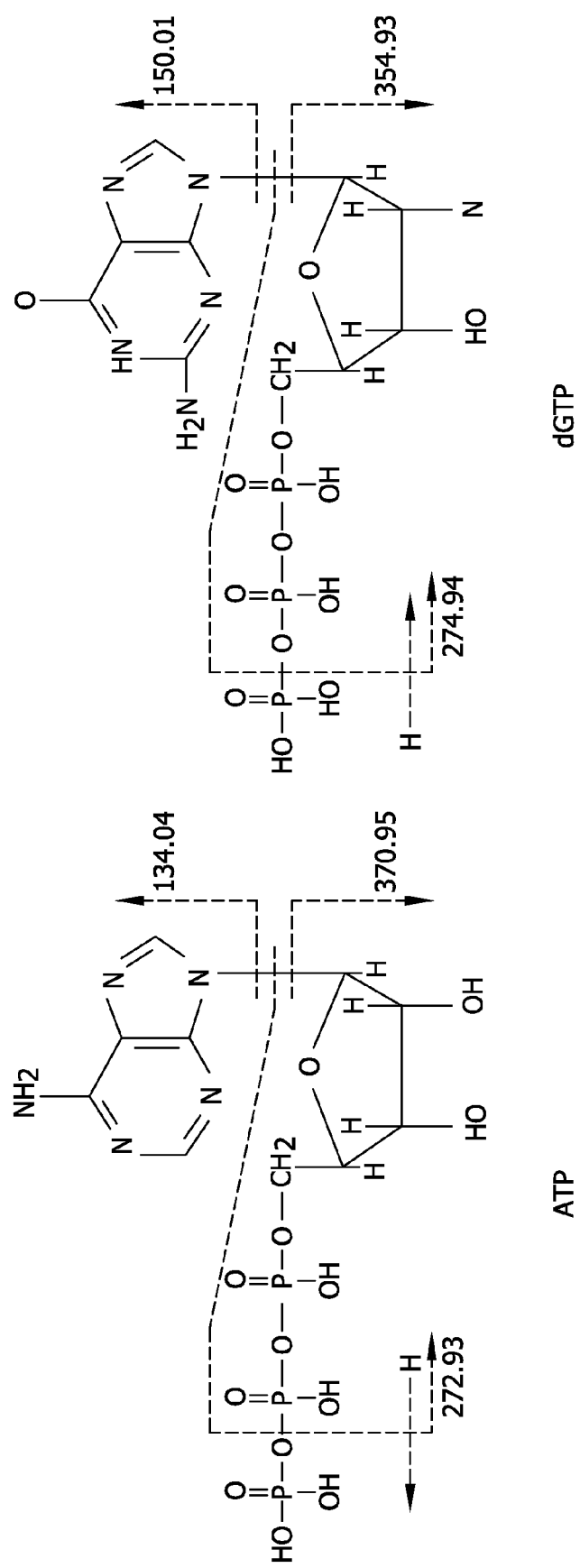
Figure 7:
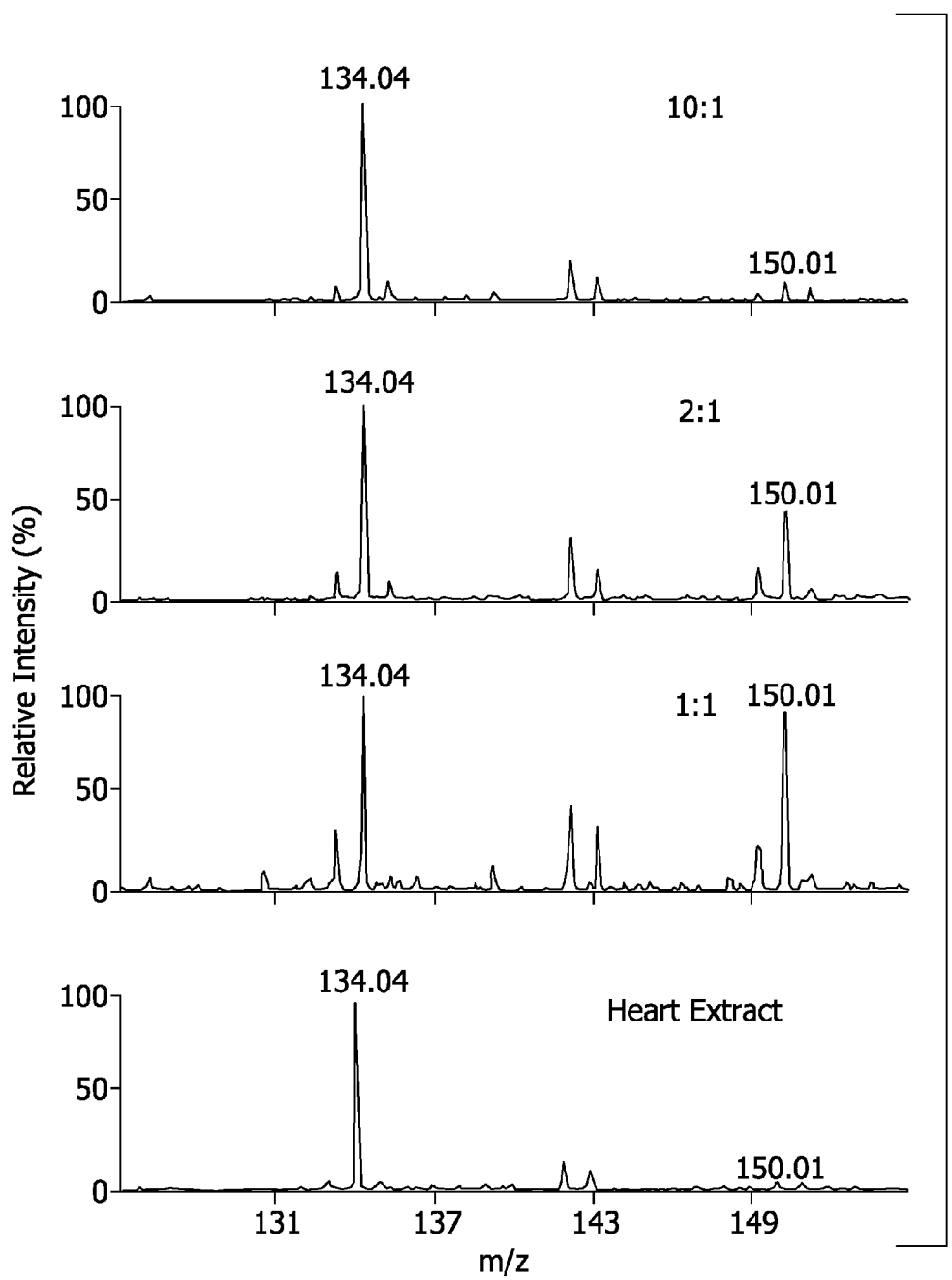
FIG. 7. Comparisons of sectional tandem MS spectra of mixtures of authentic ATP and authentic dGTP at various molar ratios and the ions at m/z 505.99 present in mouse heart extracts. Authentic ATP and authentic dGTP were mixed at molar ratios of 10:1, 2:1, and 1:1. The spectrum at the bottom shows a sectional tandem MS spectrum of a metabolite from mouse heart extract with anion peak at m/z 505.99 that was extracted from 20 mg of mouse heart tissue using the M/C/H method. All the spectra were recorded on a 4800 MALDI-TOF/TOF Analyzer in MS-MS negative ion mode using 9-aminoacridine as matrix with CID on, metastable suppressor on, and timed ion selector enabled. The voltages of source 1, collision cell, and collision cell off set are 8.0, 7.0, and −0.035 kV, respectively. The collision gas is air at medium pressure. The tandem mass spectrum was obtained by averaging 2000 consecutive laser shots (50 shots per subspectra and 40 subspectra).

Since dGTP is isomeric with ATP, it is not possible to definitively assign the ion peaks at m/z 505.99 in the mass spectrum of murine myocardium to either moiety. However, tandem MS spectra of the ion peak at m/z 505.99 and comparisons with tandem MS spectra of authentic dGTP and ATP allow definitive assignment of isomeric composition (FIG. 6(A-C)). The tandem spectra of ATP and dGTP are completely identical except for six diagnostic fragment peaks at m/z 134.01, 272.89, and 370.94 in FIG. 6(A) and at m/z 150.01, 274.94, and 354.93 in FIG. 6(B). Among these six signature peaks, fragment ion peaks at m/z 134.01 and 150.01 represent the adenine group and the guanine group that were generated from the fragmentation of the nucleotide moiety of ATP and dGTP, respectively. Tandem MS analyses of three standard mixtures, representing ratios of ATP to dGTP from 0.1:1 to 10:1, were prepared and analyzed by MALDI-tandem mass spectrometry (FIG. 7). Specifically, authentic ATP and authentic GTP were mixed at molar ratios of 10:1, 2:1, and 1:1. The spectrum at the bottom shows a sectional tandem MS spectrum of a metabolite from mouse heart extract with anion peak at m/z 505.99 that was extracted from 20 mg of mouse heart tissue using the M/C/H method. All the spectra were recorded on a 4800 MALDI-TOF/TOF analyzer in MS-MS negative ion mode using 9-aminoacridine as matrix with CID on, metastable suppressor on, and timed ion selector enabled. The voltages of source 1, collision cell, and collision cell off set are 8.0, 7.0, and −0.035 kV, respectively. The collision gas is air at medium pressure. The tandem mass spectrum was obtained by averaging 2000 consecutive laser shots (50 shots per subspectra and 40 subspectra). The results demonstrate that the isomeric ion peak area ratios of m/z 134.01-150.01 were equal to the molar ratios of ATP to dGTP within experimental error. These results substantiate the use of tandem mass spectral isomeric ratios in the assignment of the molar ratios of ATP/dGTP in a mixture. Based on this strategy, the molar ratio of ATP/dGTP in mouse heart extract was determined to be ~25 by calculating the isomeric ion peak area ratios of m/z 134.01-150.01 in the tandem mass spectra of isomeric ion peaks at m/z 505.99 (the bottom of FIG. 7). These data suggest that the contribution of dGTP to the isomeric ion peak at m/z 505.99 was less than 5%. Using this strategy, it was found that the ion peaks at m/z 426.01 and 346.01 also result largely (>95%) from ADP and AMP, respectively.

Quantitative Analyses of Mixtures of Five Compounds through Stable Isotope Analysis: Acetyl-CoA and Acetyl-CoA-$^{13}C_2$, ATP and ATP-$^{13}C_{10}$,$^{15}N_5$, Succinate and Succinate-$d_4$, Lactate and Lactate-$^{13}C$, and Pyruvate and Pyruvate-$^{13}C$. MALDI-tandem mass spectrometric analyses of five mixtures: acetyl-CoA and acetyl-CoA-$^{13}C_2$, ATP and ATP-$^{13}C_{10}$,$^{15}N_5$, succinate and succinate-$d_4$, lactate and lactate-$^{13}C$, and pyruvate and pyruvate-$^{13}C$, were performed in the negative ion mode. A plot of the ratio of the concentrations range of acetylCoA to stable isotope labeled acetyl-CoA varied over a one thousand fold concentration range from 2.35 fmol to 2.35 nmol demonstrated that a straight line with a slope of 1.00015 and a correlation coefficient of 0.9999 was obtained as typically occurs using stable isotope analogs of naturally occurring metabolites. The linear dynamic concentration ranges for the quantitation of ATP, succinate, lactate, and pyruvate were found to be 50 fmol-50 nmol, 17.4 pmol-17.4 nmol, 95 pmol-228 nmol, and 5.2 pmol-52 nmol. These results demonstrate that this methodology can be used to quantitate acetyl-CoA, ATP, succinate, lactate, and pyruvate by ratiometric comparison of their ion peak areas with their stable isotope-labeled internal standards and that accurate quantitation by MALDI-TOF MS is achievable using stable isotope-labeled standards. The detection limits for acetyl-CoA, ATP, succinate, lactate, and pyruvate, were 2 fmol, 16.7 fmol, 3.0 pmol, 30 pmol, and 3.3 pmol, respectively, in 1 μL of solution added to the matrix.

We were unable to quantitate ADP and AMP in mouse heart extracts. The laser energy necessary to generate an ADP signal suitable for quantitative analysis was much higher than that leading to intrasource ATP fragmentation. This was demonstrated by the fact that a stable isotope-labeled ADP signal was always found with the ADP signal, although only stable isotope-labeled ATP had been added to the extracts prior to MS analysis. Intrasource fragmentation of ATP was confirmed by the increase of ADP formation in concert with the increase of applied laser energy when only ATP was present in the sample spot. In addition, intrasource fragmentation of ADP to generate AMP was observed when laser power was increased to the threshold required to produce an AMP signal on MALDI-tandem mass spectrometry. This observation can be explained by the facile hydrolysis of the P—O bond hydrolysis in di- and triphosphorylated nucleotides that is exploited in cells by coupling this reaction to the catalysis of energetically unfavorable reactions.

Metabolomic Analysis of Mouse Tissue Extracts. Using stable isotope-labeled counterparts as internal standards, five energy metabolites (acetyl-CoA, ATP, succinate, lactate, pyruvate) were quantitated by analyzing heart tissue extracts from C57BL/6 wild type mice (Table 1). In wild type mouse heart tissue, ATP content was found to be 4.68±1.11 nmol/mg of wet weight, which is consistent with that previously measured in rat heart tissue by $^{31}$P NMR. Acetyl-CoA is a key energy metabolite that is produced in vivo via two main pathways: fatty acid β-oxidation and pyruvate decarboxylation. Quantitation of acetyl-CoA has been performed via an enzymatic reaction using citrate synthase and malate dehydrogenase with the sensitivity of 200 pmol/assay or through a reversed-phase high-performance liquid chromatography with the sensitivity of 12 pmol/assay. Obviously, the sensitivity of the shotgun metabolomics approach (3 fmol/assay) is more than 3 orders of magnitude higher than previous methods, permitting detection of low abundance metabolites from extremely small tissue samples (e.g., biopsies). The levels of acetyl-CoA and the other three metabolites quantitated by comparison to commercially available standards in murine myocardium are listed in Table 1.

TABLE 1

Concentrations of Six Energy Metabolites in Wild Type Mouse Heart[a]

| Metabolites | content |
|---|---|
| acetyl-CoA | 31.5 ± 0.9[b] |
| ATP | 4.68 ± 1.11[c] |
| cAMP | 66 ± 10.0[b] |
| Succinate | 1.28 ± 0.19[c] |
| Lactate | 19.6 ± 1.88[c] |
| Pyruvate | 1.74 ± 0.46[c] |
| lactate/pyruvate (mean) | 11.3 |

[a] Metabolites were extracted from 20-30 mg of C57BL/6 wild type mouse heart tissue using the methanol/chloroform/$H_2O$ extraction method. The data were quantitated on MALDI-tandem mass spectrometry using stable isotope-labeled compounds as internal standards in the negative ion mode.
[b] The results are expressed in pmol/mg of wet weight and represent means ± SD of five different animals.
[c] The results are expressed in nmol/mg of wet weight and represent means ± SD of five different animals.

Figures 8C, 8D:
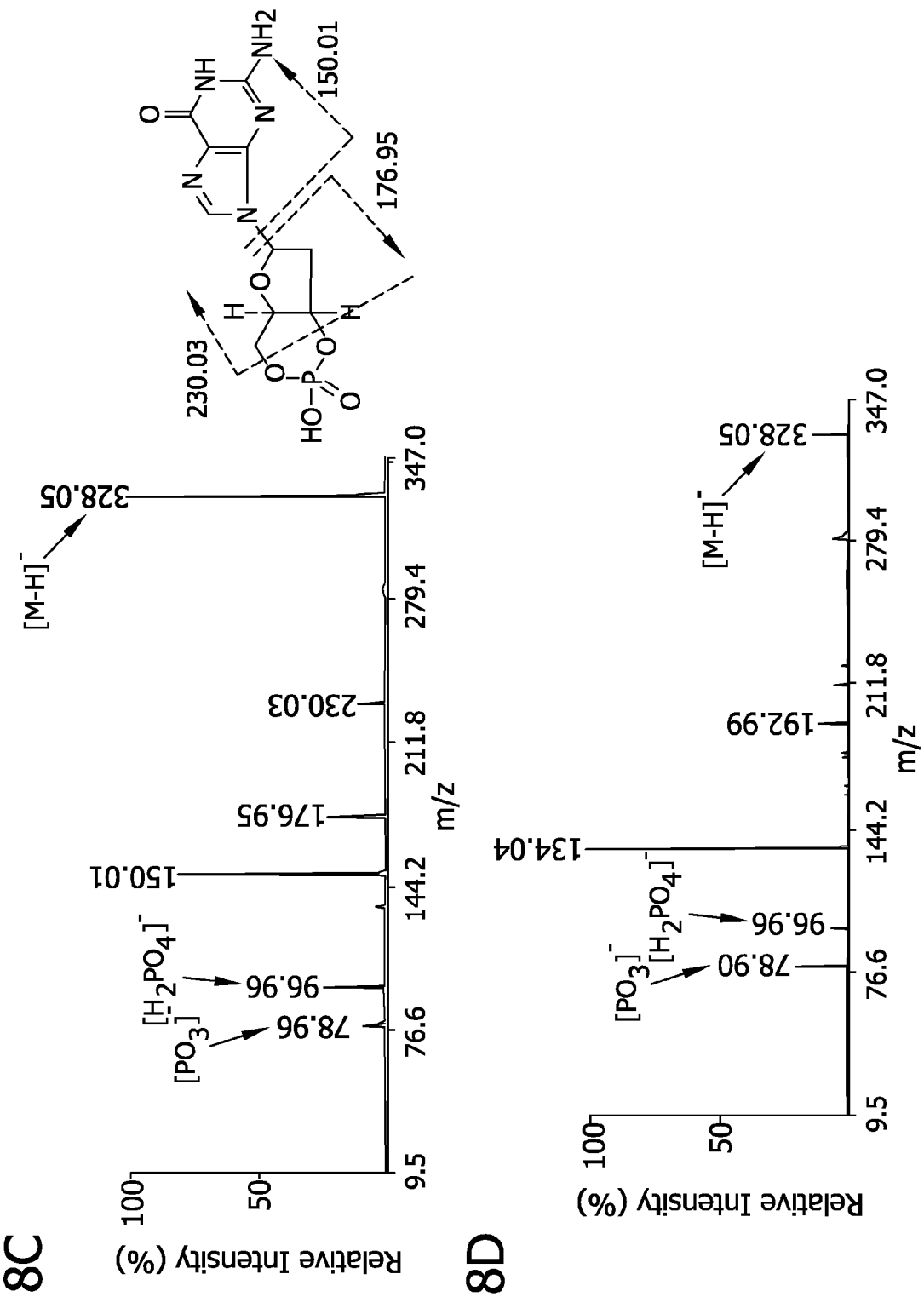
FIG. 8. Comparison of tandem MS spectra of authentic cAMP, authentic adenosine 2,3-cyclic monophosphate, authentic 2-deoxyguanosine-3,5-cyclic monophosphate (cdGMP), and a metabolite at m/z 328.05 from mouse heart extract. (A) is the tandem MS spectrum of authentic cAMP; (B) is the tandem MS spectrum of authentic adenosine 2,3-cyclicmonophosphate; (C) is the tandem MS spectrum of authentic cdGMP; and (D) is the tandem MS spectrum of mouse heart extract metabolite with ion peak at m/z 328.05. All the tandem MS spectra were recorded on a 4800 MALDI-TOF/TOF Analyzer in MS-MS negative ion mode using 9-aminoacridine as matrix with CID off, metastable suppressor on, and timed ion selector enabled. The voltages of source 1, collision cell, and collision cell off set were 8.0, 7.0, and −0.035 kV, respectively. The collision gas was air at medium pressure. The tandem MS spectrum was obtained by averaging 2000 consecutive laser shots (50 shots per subspectra and 40 subspectra). The chemical structures of cAMP, adenosine 2,3-cylic monophosphate, and cdGMP on the right side show the assignments of their signature peaks.

Identification and Quantitation of cAMP in Murine Heart Extracts. cAMP is a nearly ubiquitous second messenger used in intracellular signal transduction pathways present in low amounts. The detection and quantitation of cAMP in animal tissue is currently achieved using either a radioimmunoassay procedure or fluorescence-based immunoassay. Although the measurement of cAMP in plant cells has been performed using ESI-MS, mass spectrometric determination of cAMP using MALDI or in animal tissues has not been reported to the best of our knowledge. Using the MALDI-tandem mass spectrometric approach developed herein, cAMP was successfully detected in murine hearts (FIG. 2(C)) as the ion peak at m/z 328.04. Its chemical identity was confirmed as cAMP by fragmentation profiles identical to those obtained with authentic cAMP (FIG. 8(A)). Two isomers of cAMP shared an ion peak at m/z 328.04, adenosine 2',3'-cyclic monophosphate and 2'-deoxyguanosine-3',5'-cyclic monophosphate (cdGMP), but were excluded by comparisons of tandem MS spectra of adenosine 2',3'-cyclic monophosphate (FIG. 8(B)) and cdGMP standards (FIG. 8(C)) with the peak from the murine heart extract (FIG. 8(D)). The detection limit of cAMP on MALDI-tandem mass spectrometry was 1 pmol/1 µL of solution extract.

Figure 9:
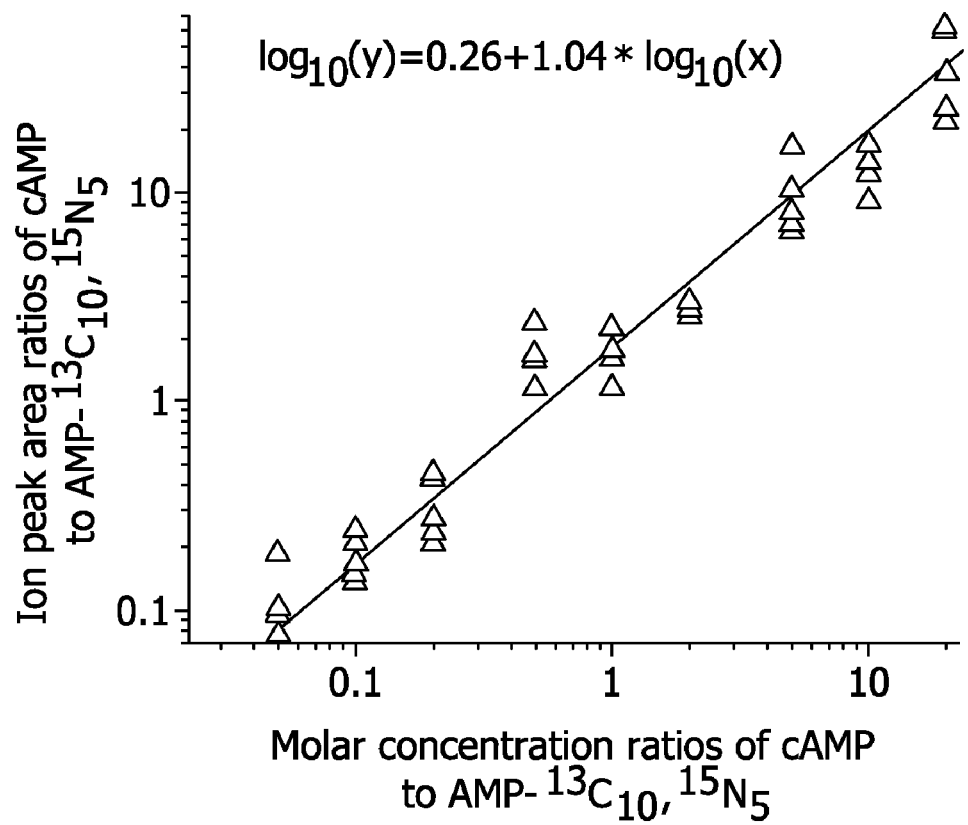
FIG. 9. Standard curve for quantitation of cAMP using AMP-$^{13}C_{10}$,$^{15}N_5$ as an internal standard that was obtained by quantitative analyses of authentic cAMP and AMP-$^{13}C_{10}$,$^{15}N_5$ mixed at different molar ratios and analyzed with the 4800MALDI-TOF/TOF Analyzer. The obtained linear correlation between logarithmic ion peak area ratios and molar ratios of cAMP standard and AMP-$^{13}C_{10}$,$^{15}N_5$ was in the molar ratio range of 0.05-20. The concentrations of cAMP varied from 1 pmol to 20 pmol.
Figure 10:
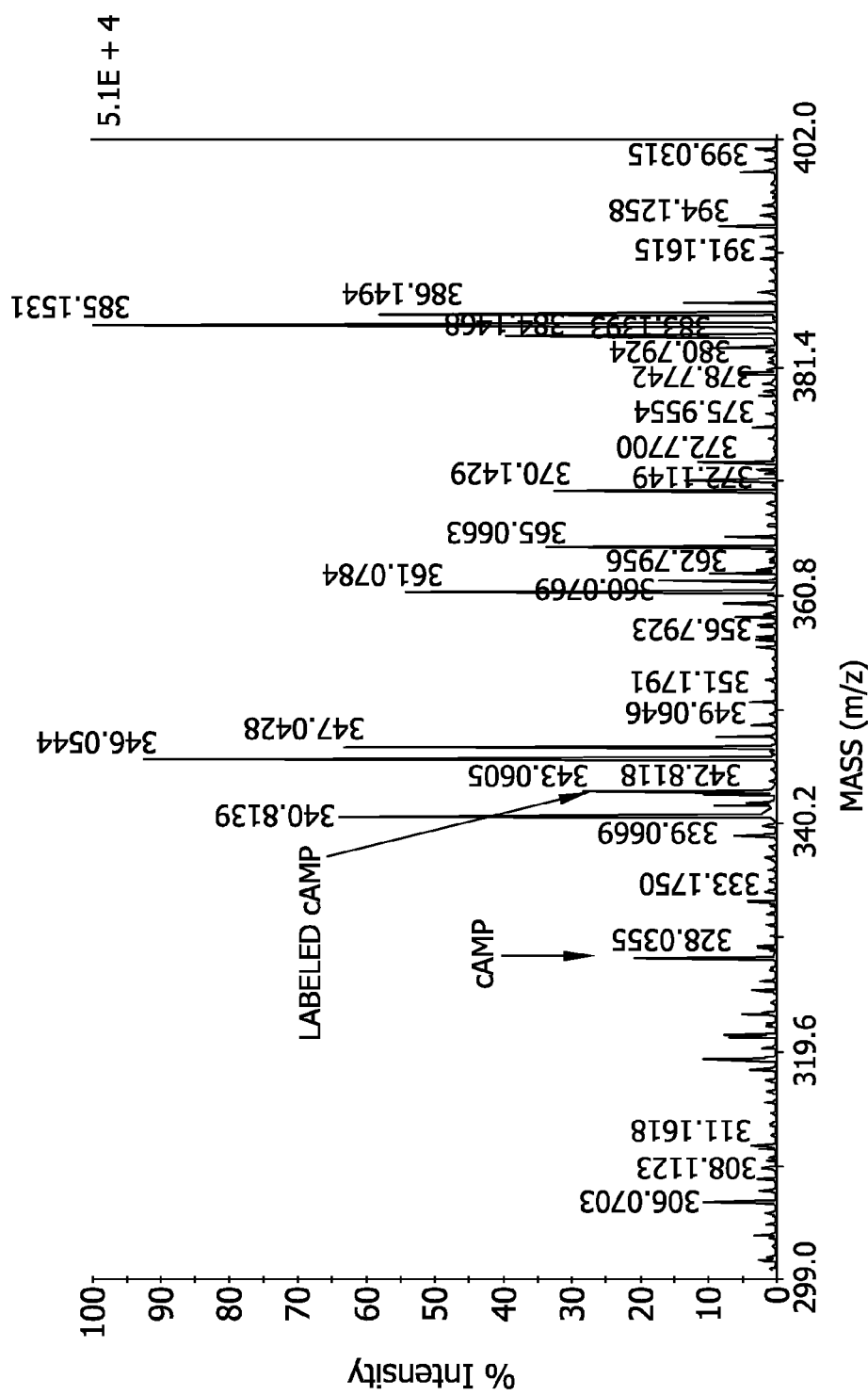
FIG. 10. Expanded mass spectrum of the metabolites extracted from mouse heart tissue with spiking synthetic stable isotope labeled cAMP. The mass spectrum was acquired on a 4800 MALDI-TOF/TOF Analyzer in the negative ion mode using 9-aminoacridine as matrix under neutral condition (sample pH was 7.0 and matrix solvent was acetone). Metabolites were extracted using the M/C/H extraction method. A 100 μL aliquot of the murine heart extract was dried under a nitrogen stream and reconstituted in 100 μL water. 2 μL of prepared labeled cAMP solution (22 pmol/μL) was added to 10 μL of reconstituted sample. After mixing 10 μL of sample with 10 μL of 9-aminoacridine that was dissolved in acetone (10 mg/mL), 1 μL of the mixture was spotted on a 384 well plate. MS analysis was performed on a 4800 MALDI-TOF/TOF Analyzer. Individual mass spectra of metabolites were obtained by averaging 1500 consecutive laser shots (50 shots per subspectra and 30 subspectra). Labeled cAMP was prepared from ATP-$^{13}C_{10}$,$^{15}N_5$ through the catalysis of adenylate cyclase. By ratiometric comparison of peak areas of cAMP to CATP-$^{13}C_{10}$,$^{15}N_5$, the concentration of cAMP in WT mouse heart was determined to be ~40 pmol/mg wet weight.
Figure 11:
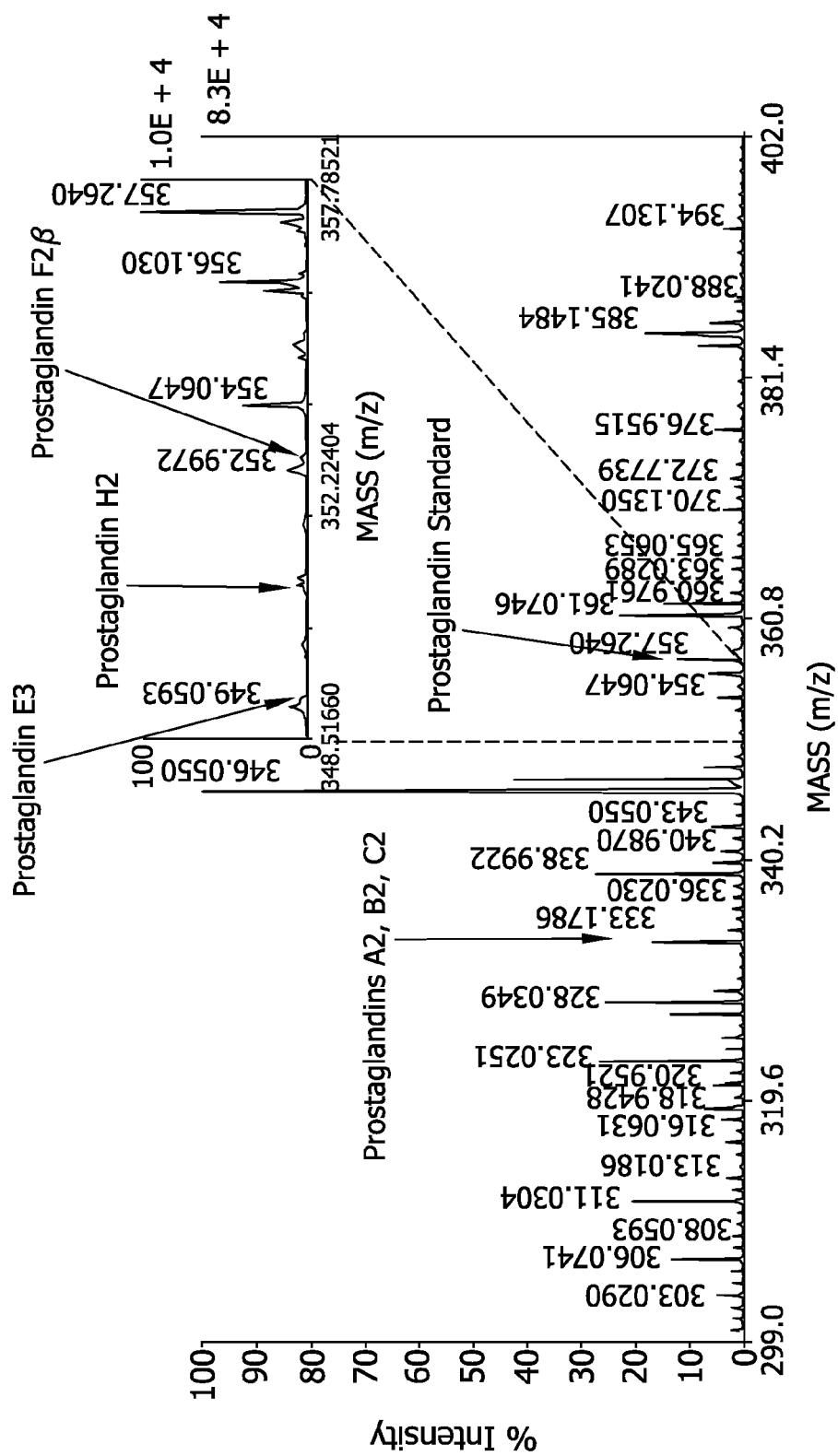
FIG. 11. Expanded mass spectrum of prostaglandins present in mouse heart tissue were quantified by comparisons with stable isotope standards of deuterated prostaglandin F2α-D$_4$. Mass spectrum was acquired on a 4800 MALDI-TOF/TOF Analyzer in the negative ion mode using 9-aminoacridine as matrix under neutral condition (sample pH was 7.0 and matrix solvent was acetone). Metabolites were extracted using the M/C/H extraction method. A 100 μL aliquot of the murine heart extract was dried under a nitrogen stream and reconstituted in 100 μL water. After mixing 10 μL of sample with 10 μL of 9-aminoacridine that was dissolved in acetone (10 mg/mL), 1 μL of the mixture was spotted on a 384 well plate. MS analysis was performed on a 4800 MALDI-TOF/TOF Analyzer. Individual mass spectrum of metabolites was obtained by averaging 1500 consecutive laser shots (50 shots per subspectra and 30 subspectra).
Figure 12:
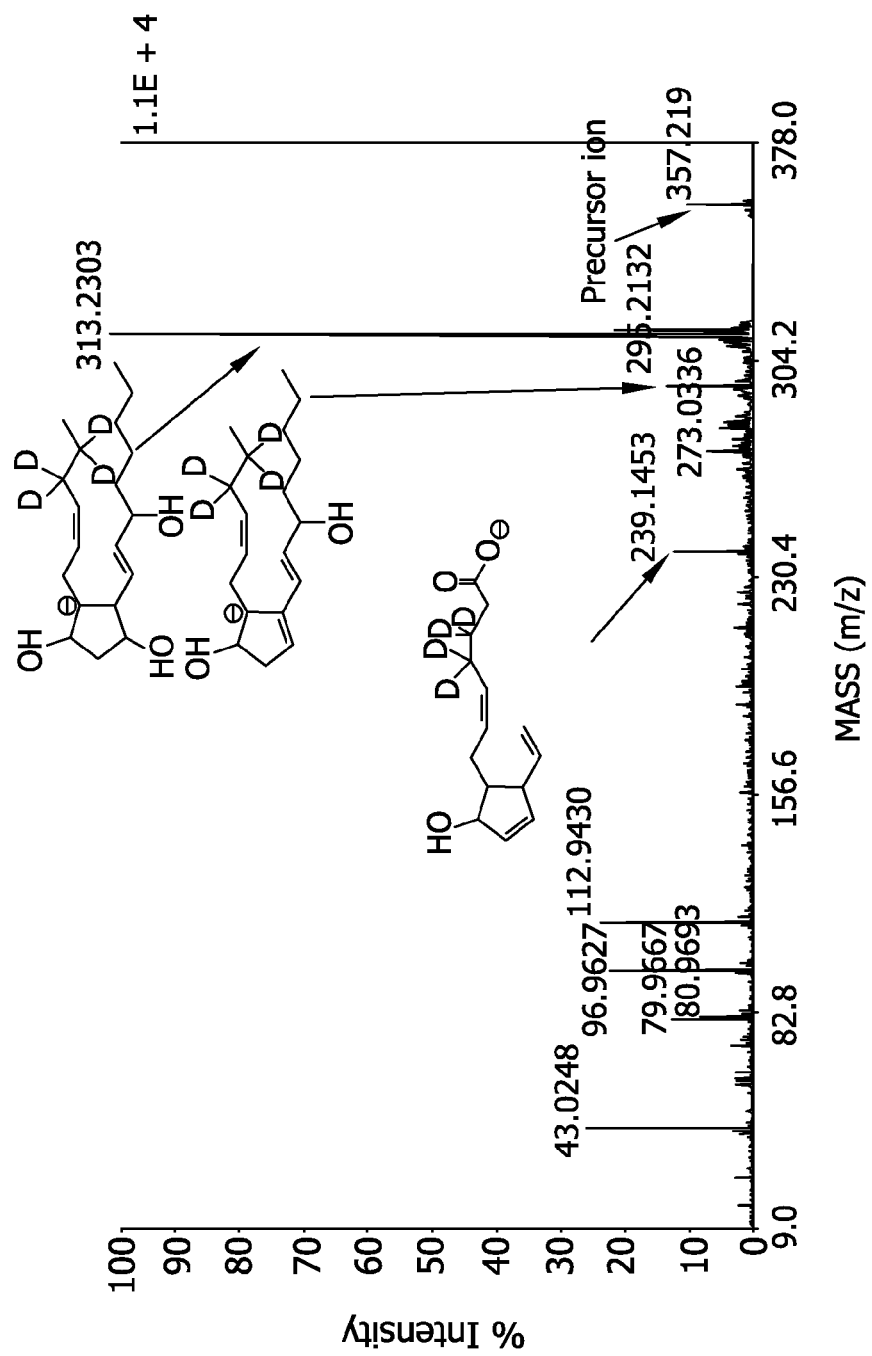
FIG. 12. Tandem MS spectrum of stable isotope labeled prostaglandin F2α-D$_4$ after high energy fragmentation. The tandem MS/MS spectrum was acquired using a 4800 MALDI-TOF/TOF Analyzer in the negative ion mode using 9-aminoacridine as matrix with high energy fragmentation. The voltages of source 1, collision cell and collision cell offset were 8.0 kV, 7.0 kV and −0.035 kV, respectively. The collision gas was air at medium pressure. The tandem MS spectrum was obtained by averaging 2000 consecutive laser shots (50 shots per subspectra and 40 subspectra).
Figure 13:
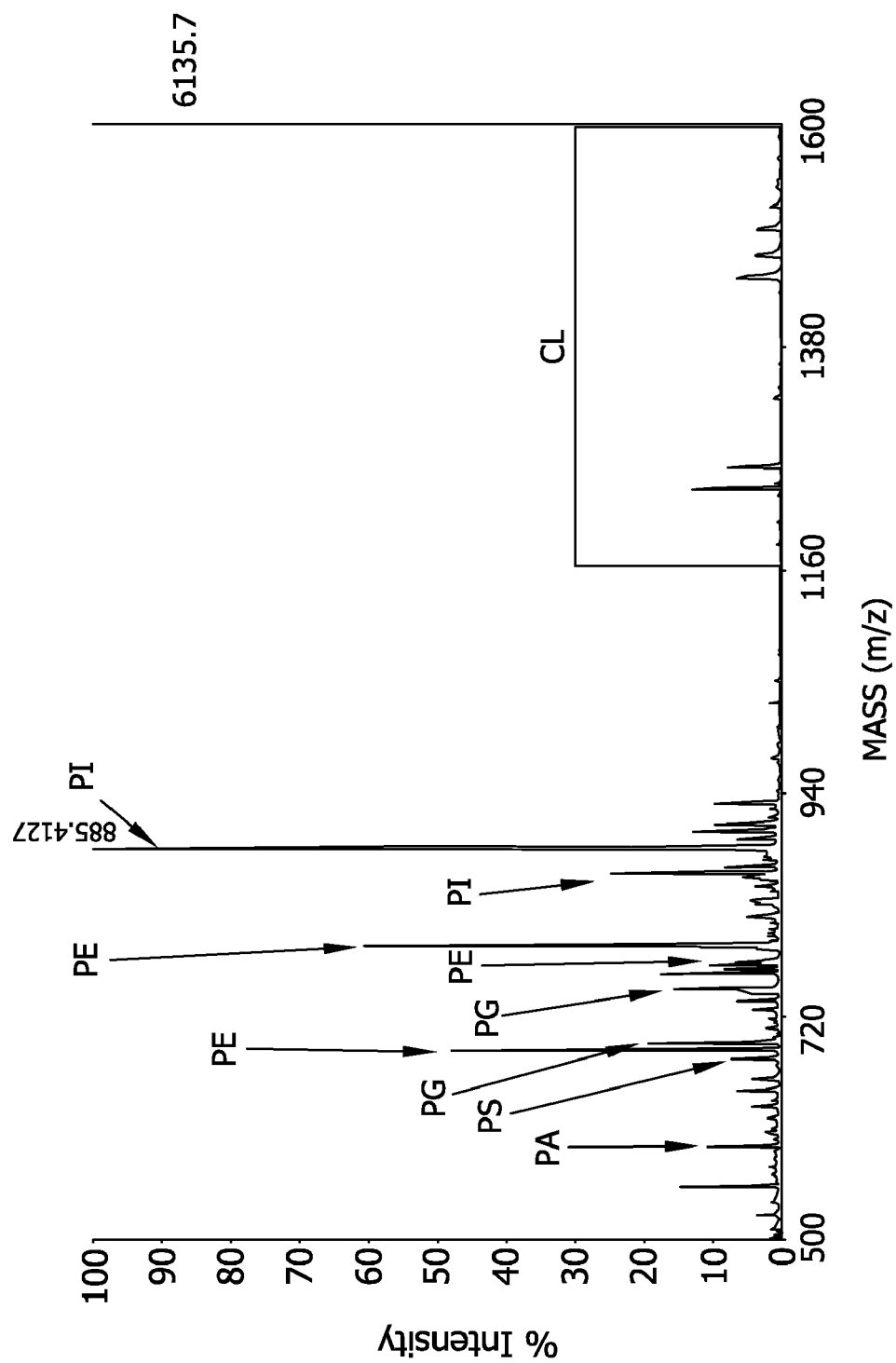
FIG. 13. Mass spectrum of a lipid extract from mouse heart tissue at neutral pH. Mice were sacrificed by asphyxiation with carbon dioxide and the hearts were quickly excised and immersed in ice-cold buffer (250 mM sucrose/25 mM imidazole, pH 8.0, at 4° C.). After extraneous tissue and epicardial fat were removed, each heart was blotted to remove excess liquid and immediately freeze-clamped at the temperature of liquid nitrogen. Myocardial wafers were pulverized into a fine powder with a stainless steel mortar and pestle. Thus, prior work neither addressed the ability of this matrix to effectively result in situ multiplexing of matrix-analyte interactions nor the utility of this matrix for tandem mass spectrometric analysis. Internal standards (including diC16:0 phosphatidylethanolamine, tetra 14:0 cardiolipin, tri C17:1 triglycerides, C17:0 lysophospholipids, diC14 phosphatidylcholine, diC16:0 phosphatidylserine, diC15:0 phosphatidylglycerol, or other non naturally occurring species have also provided satisfactory internal standards) were added to each myocardial sample. The extraction mixture was centrifuged at 2500 rpm for 10 min. The chloroform layer was carefully removed and saved. To the MeOH/H$_2$O layer of each test tube was added an additional 2 mL of chloroform, and chloroform layer was separated as above. The chloroform extracts from each identical sample were combined and dried under a nitrogen stream. The residue was then resuspended in 4 mL of chloroform/methanol (1:1) and reextracted against 1.8 mL of 20 mM LiCl aqueous solution, and the extract was dried as described above. Individual residues were resuspended in ~1 mL of chloroform and filtered with a 0.2 μm PFTE syringe filter into a 5 mL glass centrifuge tube (this step was repeated twice). The chloroform solution was subsequently dried under a nitrogen stream, and each individual residue was reconstituted with a volume of 500 μL/mg protein (which was based on the original protein content of the samples as determined from protein assays) in 1:1 chloroform/methanol. 50 μl of resultant lipid sample was dried under N$_2$ stream and reconstituted in 500 μl in methanol-water (9/1, v/v) solution. 9-aminoacridine (10 mg/ml) was dissolved in methanol-water (9/1, v/v) solution. After mixing 10 μl of reconstituted sample with 10 μl of 9-aminoacridine, 1 μL of the mixture is spotted on a 384 well plate. MS analysis was performed on a 4800 MALDI-TOF/TOF Analyzer in the negative ion mode. Mass spectra were obtained by averaging 1500 consecutive laser shots (50 shots per subspectra and 30 subspectra) with default calibration.
Figure 14:
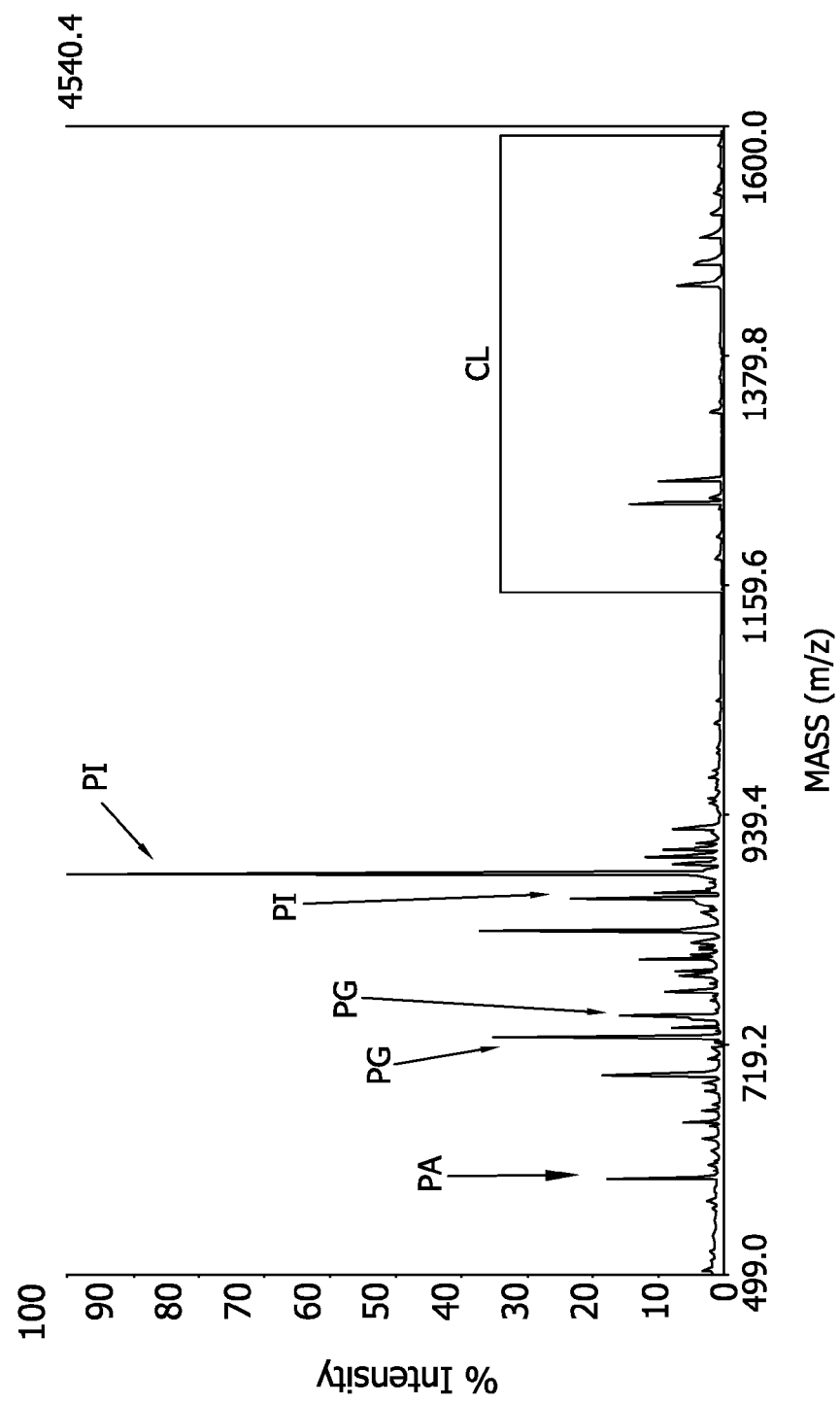
FIG. 14. Mass spectrum of a lipids extract from mouse heart tissue at basic pH. Mice were sacrificed by asphyxiation with carbon dioxide and the hearts were quickly excised and immersed in ice-cold buffer (250 mM sucrose/25 mM imidazole, pH 8.0, at 4° C.). After extraneous tissue and epicardial fat were removed, each heart was blotted to remove excess liquid and immediately freeze-clamped at the temperature of liquid nitrogen. Myocardial wafers were pulverized into a fine powder with a stainless steel mortar and pestle. Lipids were extracted from myocardium of C57BL/6 male mice by a modified Bligh and Dyer procedure. Internal standards were added to each myocardial sample. The extraction mixture was centrifuged at 2500 rpm for 10 min. The chloroform layer was carefully removed and saved. To the MeOH/H$_2$O layer of each test tube was added an additional 2 mL of chloroform, and chloroform layer was separated as above. The chloroform extracts from each identical sample were combined and dried under a nitrogen stream. Each individual residue was then resuspended in 4 mL of chloroform/methanol (1:1) and reextracted against 1.8 mL of 20 mM LiCl aqueous solution, and the extract was dried as described above. Individual residues were resuspended in ~1 mL of chloroform and filtered with a 0.2 μm PFTE syringe filter into a 5 mL glass centrifuge tube (this step was repeated twice). The chloroform solution was subsequently dried under a nitrogen stream, and each individual residue was reconstituted with a volume of 500 μL/mg protein (which was based on the original protein content of the samples as determined from protein assays) in 1:1 chloroform/methanol. 50 μl of resultant lipid sample was dried under N$_2$ stream and reconstituted in 500 μl in methanol-water (9/1, v/v) solution containing 2% ammonium hydroxide. 9-aminoacridine (10 mg/ml) was dissolved in methanol-water (9/1, v/v) solution containing 2% ammonium hydroxide. After mixing 10 μl of reconstituted sample with 10 μl of 9-aminoacridine, 1 μL of the mixture was spotted on an Opti-TOF® 384 well plate. MS analysis was performed on a 4800 MALDI-TOF/TOF Analyzer in the negative ion mode. Mass spectra were obtained by averaging 1500 consecutive laser shots (50 shots per subspectra and 30 subspectra) with default calibration.
Figure 15A:
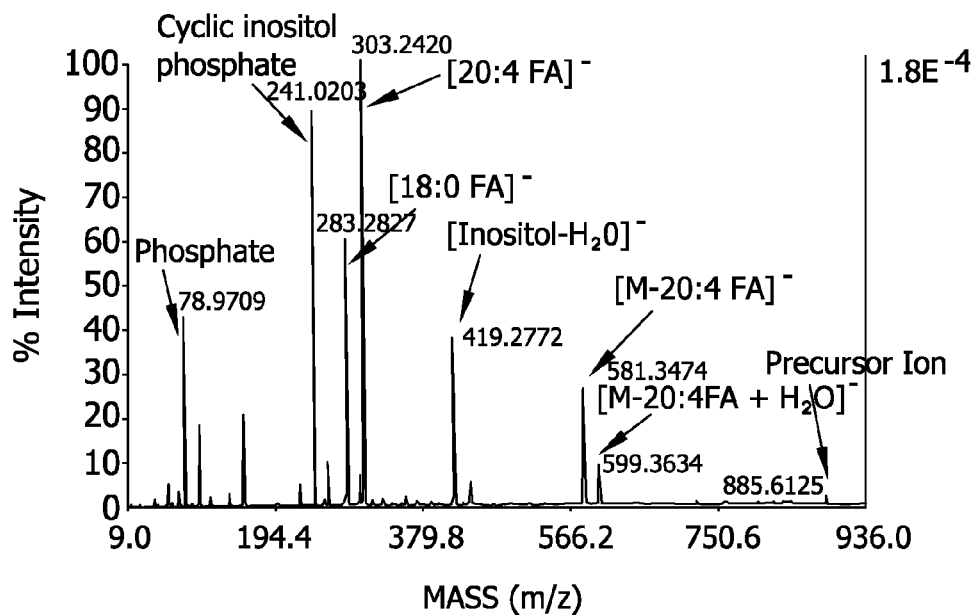
FIG. 15. Tandem mass spectra of lipid species extracted from mouse heart tissue. Mice were sacrificed by asphyxiation with carbon dioxide and the hearts were quickly excised and immersed in ice-cold buffer (250 mM sucrose/25 mM imidazole, pH 8.0, at 4° C.). After extraneous tissue and epicardial fat were removed, each heart was quickly blotted to remove excess liquid and immediately freeze-clamped at the temperature of liquid nitrogen. Myocardial wafers were pulverized into a fine powder with a stainless steel mortar and pestle. Lipids were extracted from myocardium of C57BL/6 male mice by a modified Bligh and Dyer procedure Internal standards were added to each myocardial sample. The extraction mixture was centrifuged at 2500 rpm for 10 min. The chloroform layer was carefully removed and saved. To the MeOH/H$_2$O layer of each test tube was added an additional 2 mL of chloroform, and chloroform layer was separated as above. The chloroform extracts from each identical sample were combined and dried under a nitrogen stream. Each individual residue was then resuspended in 4 mL of chloroform/methanol (1:1) and reextracted against 1.8 mL of 20 mM LiCl aqueous solution, and the extract was dried as described above. Individual residues were resuspended in ~1 mL of chloroform and filtered with a 0.2 μm PFTE syringe filter into a 5 mL glass centrifuge tube (this step was repeated twice). The chloroform solution was subsequently dried under a nitrogen stream, and each individual residue was reconstituted with a volume of 500 μL/mg protein (which was based on the original protein content of the samples as determined from protein assays) in 1:1 chloroform/methanol. 50 μl of resultant lipid sample was dried under N$_2$ stream and reconstituted in 500 μl in methanol-water (9/1, v/v) solution. 9-aminoacridine (10 mg/ml) was dissolved in methanol-water (9/1, v/v) solution. After mixing 10 μl of reconstituted sample with 10 μl of 9-aminoacridine, 1 μL of the mixture was spotted on an Opti-TOF® 384 well plate. Tandem mass spectra were recorded on a 4800 MALDI-TOF/TOF Analyzer in MS-MS negative ion mode using 9-aminoacridine as matrix with CID on, metastable suppressor on and timed ion selector enabled. The voltages of source 1, collision cell and collision cell offset were 8.0 kV, 7.0 kV and –0.035 kV, respectively. The collision gas was air at medium pressure. The tandem MS spectrum was obtained by averaging 2000 consecutive laser shots (50 shots per subspectra and 40 subspectra). A) 18:0-20:4 PtdIns; B) 18:0-18:2 PtdIns; C) 18:0-22:6 PtdEtn; D) 16:0-22:6 PtdEtn and 18:2-20:4 PtdEtn; E)16:0-18:1 PtdGro and 18:2-18:2-18:2-22:6 CL; F) 15:0-15:0 PtdGro; G)16:1-16:1 PtdEtn; H)14:0-14:0 PtdH.
Figure 15B:
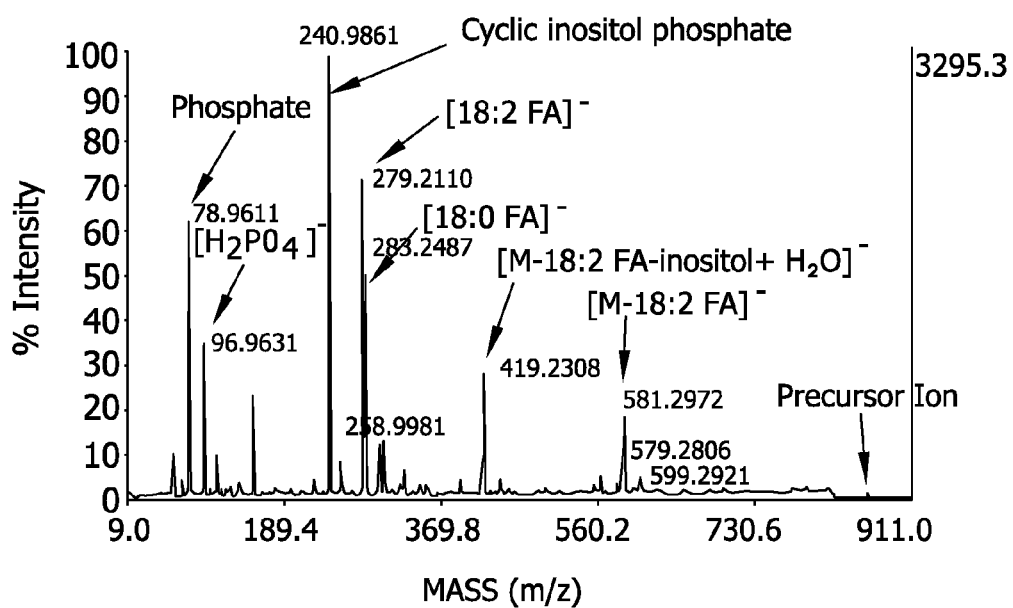
Figure 15C:
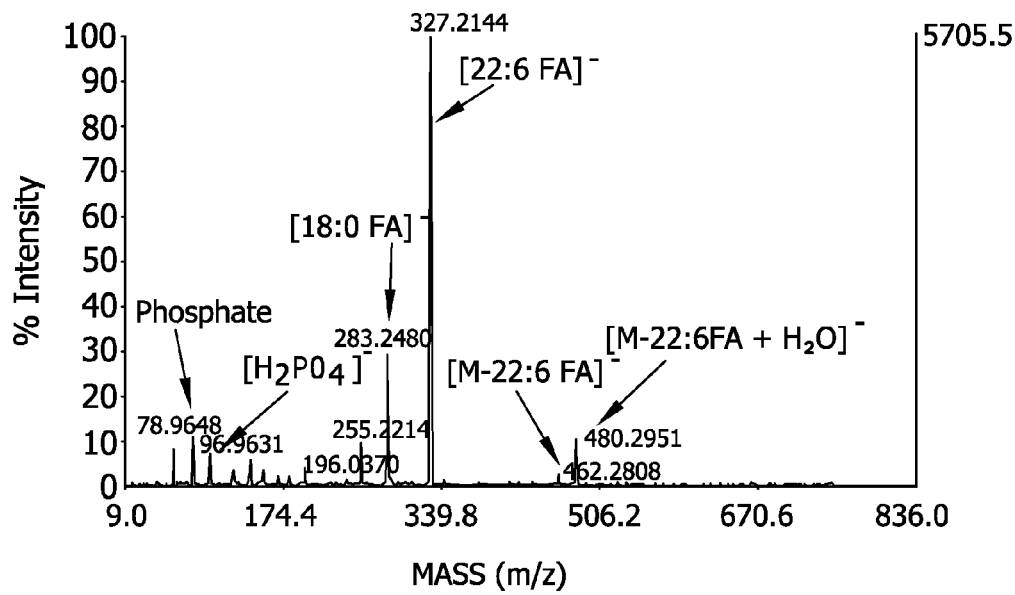
Figure 15D:
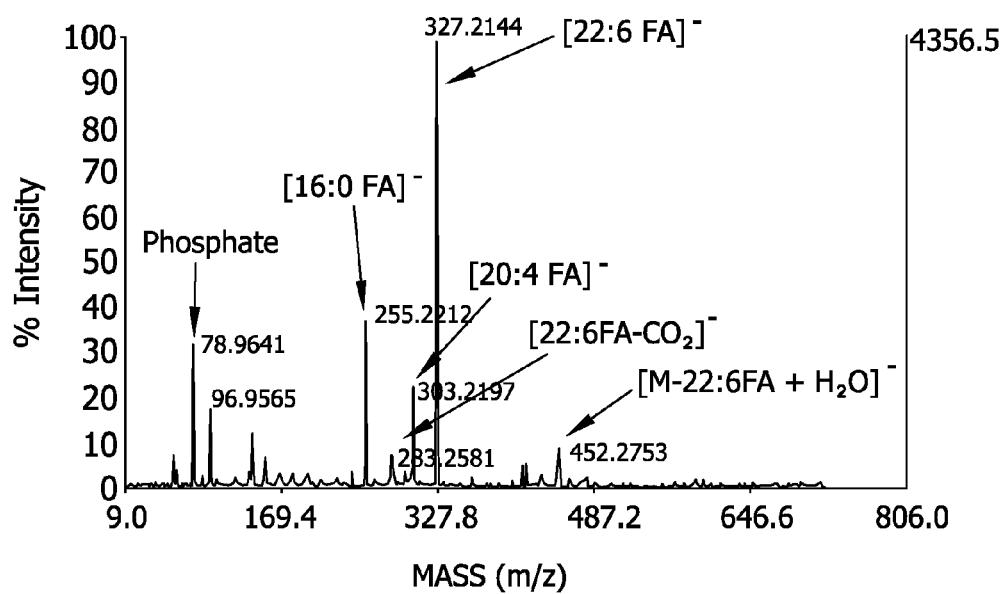
Figure 15E:
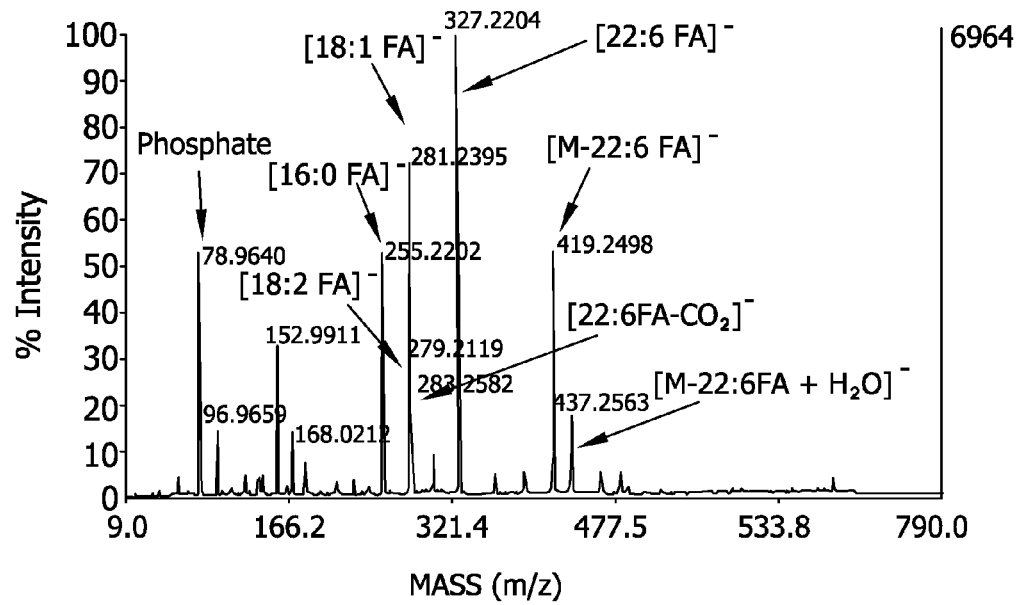
Figure 15F:
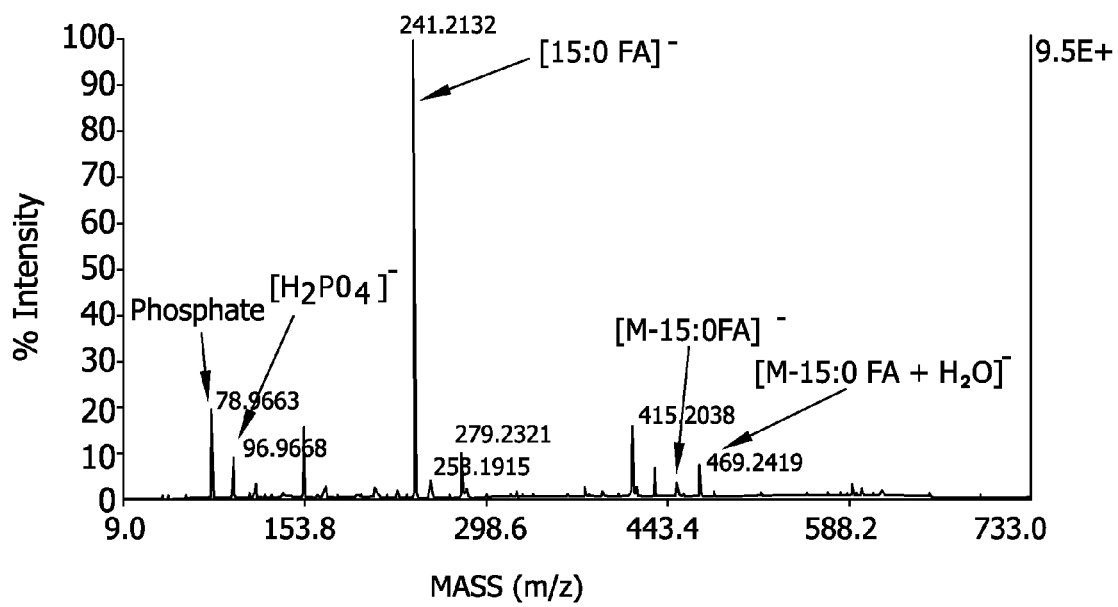
Figure 15G:
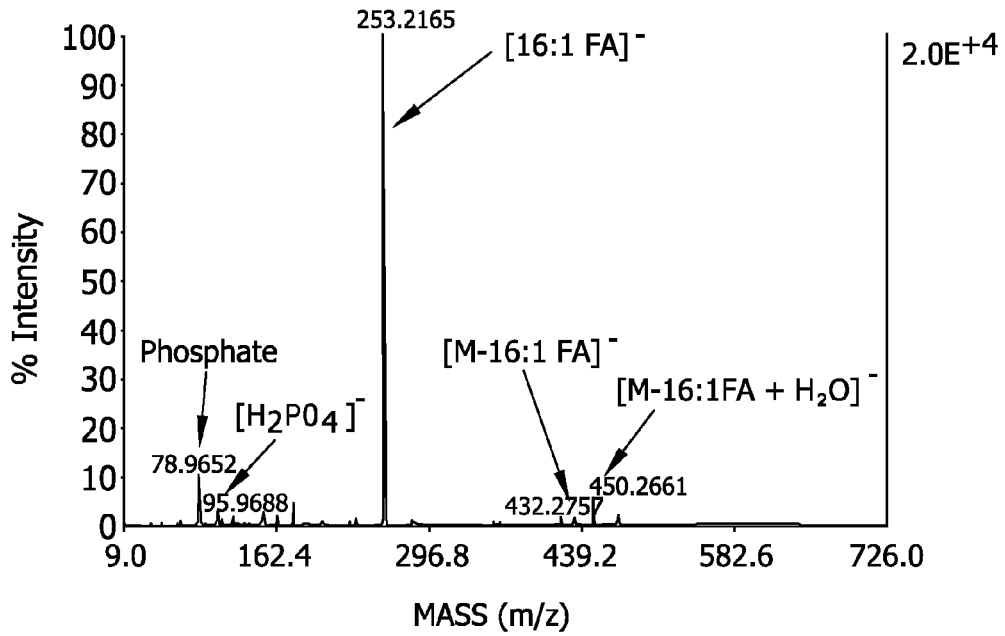
Figure 15H:
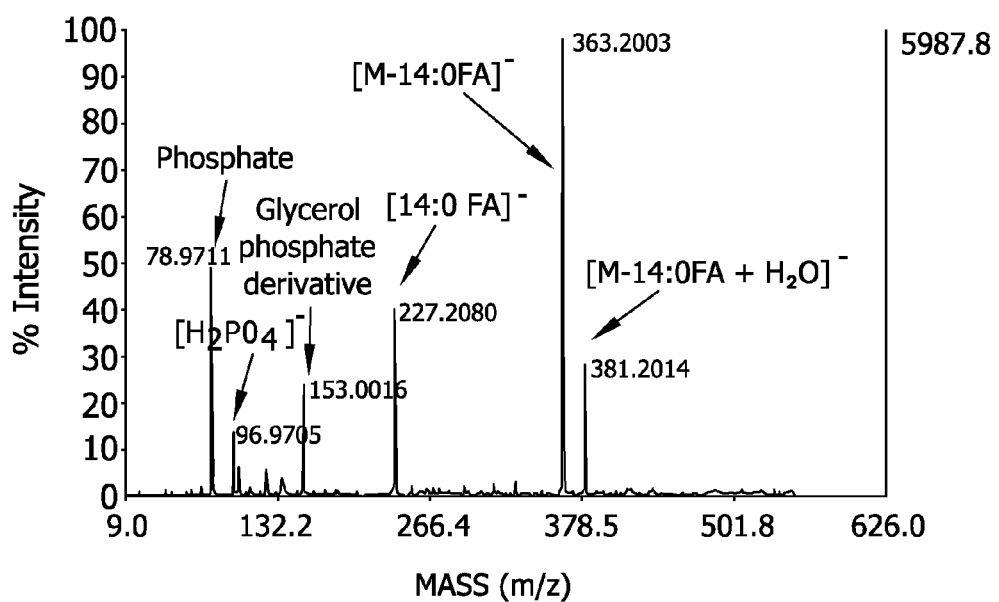
Figure 16:
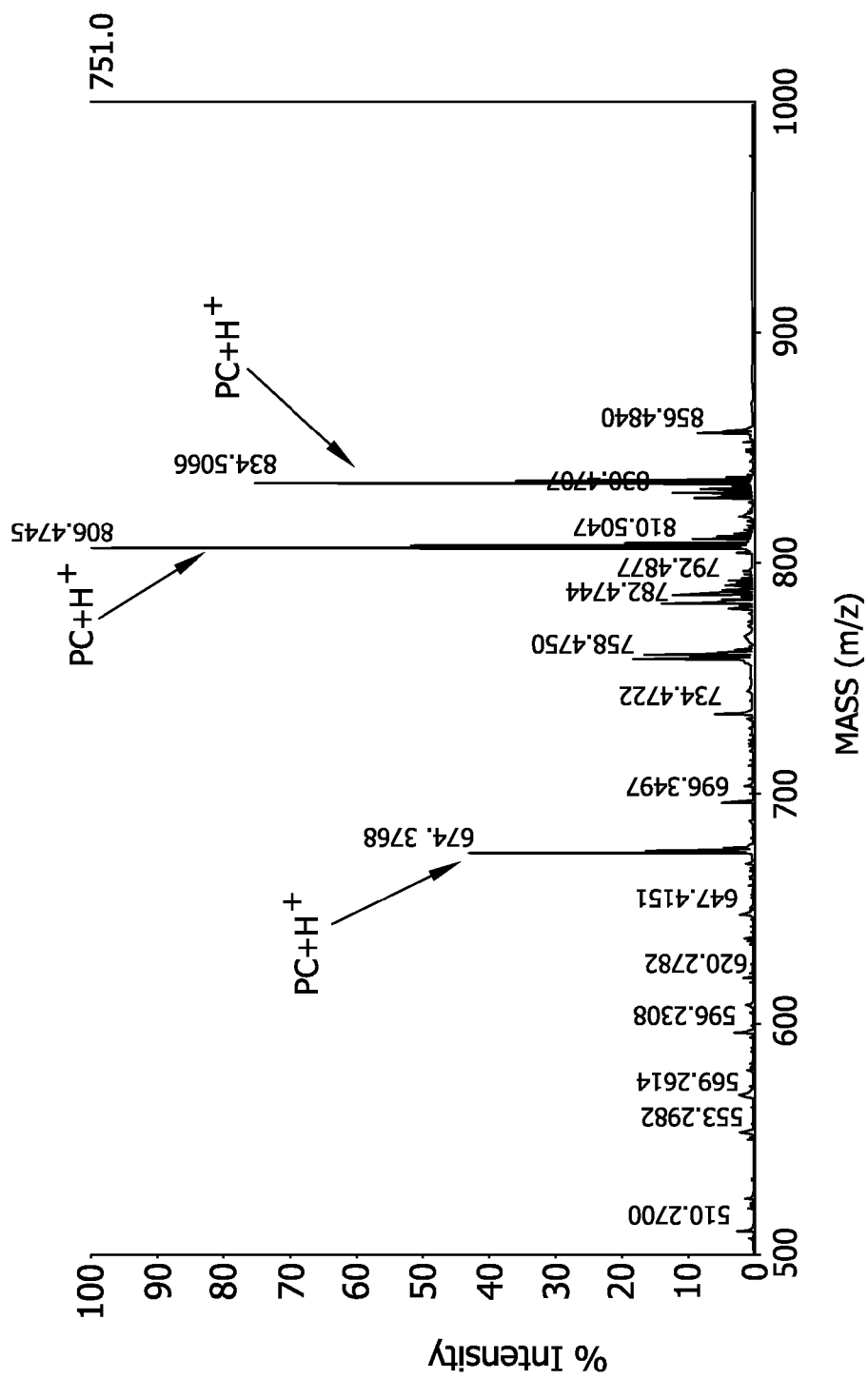
FIG. 16. Mass spectrum of a lipids extract from mouse heart tissue at basic pH. Mice were sacrificed by asphyxiation with carbon dioxide and the hearts were excised quickly and immersed in ice-cold buffer (250 mM sucrose/25 mM imidazole, pH 8.0, at 4° C.). After extraneous tissue and epicardial fat were removed, each heart was blotted to remove excess liquid and immediately freeze-clamped at the temperature of liquid nitrogen. Myocardial wafers were pulverized into a fine powder with a stainless steel mortar and pestle. Lipids were extracted from myocardium of C57BL/6 male mice by a modified Bligh and Dyer procedure Internal standards were added to each myocardial sample. The extraction mixture was centrifuged at 2500 rpm for 10 min. The chloroform layer was carefully removed and saved. To the MeOH/H$_2$O layer of each test tube was added an additional 2 mL of chloroform, and chloroform layer was separated as above. The chloroform extracts from each identical sample were combined and dried under a nitrogen stream. Each individual residue was then resuspended in 4 mL of chloroform/methanol (1:1) and reextracted against 1.8 mL of 20 mM LiCl aqueous solution, and the extract was dried as described above. Individual residues were resuspended in ~1 mL of chloroform and filtered with a 0.2 μm PFTE syringe filter into a 5 mL glass centrifuge tube (this step was repeated twice). The chloroform solution was subsequently dried under a nitrogen stream, and each individual residue was reconstituted with a volume of 500 μL/mg protein (which was based on the original protein content of the samples as determined from protein assays) in 1:1 chloroform/methanol. 50 μl of resultant lipid sample was dried under N$_2$ stream and reconstituted in 500 μl in methanol-water (9/1, v/v) solution containing 2% ammonium hydroxide. 9-aminoacridine (10 mg/ml) was dissolved in methanol-water (9/1, v/v) solution containing 2% ammonium hydroxide. After mixing 10 μl of reconstituted sample with 10 μl of 9-aminoacridine, 1 μL of the mixture was spotted on an Opti-TOF® 384 well plate. MS analysis was performed on a 4800 MALDI-TOF/TOF Analyzer in the positive ion mode. Mass spectra were obtained by averaging 1500 consecutive laser shots (50 shots per subspectra and 30 subspectra) with default calibration.

Quantitation of cAMP cannot be precisely achieved without comparison to a stable isotope internal standard. The stable isotope-labeled cAMP is not commercially available, but was prepared by using staple isotope ATP in conjunction with adenylate cyclase. This method yielded a value of 40 pmol cAMP/mg protein. In addition, by exploiting the similarity of the chemical structure of AMP to cAMP, we used stable isotope-labeled AMP to quantify the amounts of cAMP in myocardial tissue. The molar ratio of the cAMP standard relative to that of the AMP-$^{13}C_{10}$,$^{15}N_5$ was varied from 0.05 to 20, and values were plotted with the logarithmically scaled ion peak area ratios (FIG. 9). These results suggest that quantitation of cellular cAMP can be approximated using AMP-$^{13}C_{10}$, $5N_5$ as an internal standard. Applying this methodology, the content of cAMP in murine heart was found to be approximately 66 pmol/mg of wet weight (FIG. 10). The use of stable isotope labels of the compounds to be quantitated is necessary for precise measurement, but the use of other compounds with similar functionality has proven useful for ratiometric profiling. Multiple signaling metabolites can be simultaneously assessed through this approach. For example, the numerous prostaglandin metabolites that are present at m/z 333 are easily identified by MS/MS spectra through comparison of their stable isotope counterparts (FIGS. 11,12). Tandem mass spectrometry with high-energy fragmentation in the presence of multiplexed matrix conditions has also proven a powerful tool for metabolite analyses of the chloroform extract. For example, negatively charged lipid metabolites, or metabolites that can partition into one of multiple organic phases we have utilized (e.g., chloroform, butanol, acidified butanol, hexane, ethyl acetate and others) that either have a negative charge or can be induced to have a negative charge are easily measured by this procedure (FIGS. 13,14) with diagnostic tandem fragmentation patterns to identify isomeric compounds (FIGS. 15(A-D)). It is important to note that selective ionization by modulating analyte matrix interactions of metabolites in the chloroform layer are facilitated by alterations in pH that enable the selective ionization of lipid classes without chromatography (compare FIGS. 13 and 14). Examples extending into the realm of positively charged ions have also been demonstrated with suitable tandem mass spectra that can be multiplexed for spectrometric isolation of salient peaks for definitive identification (FIG. 16).

Figure 17A:
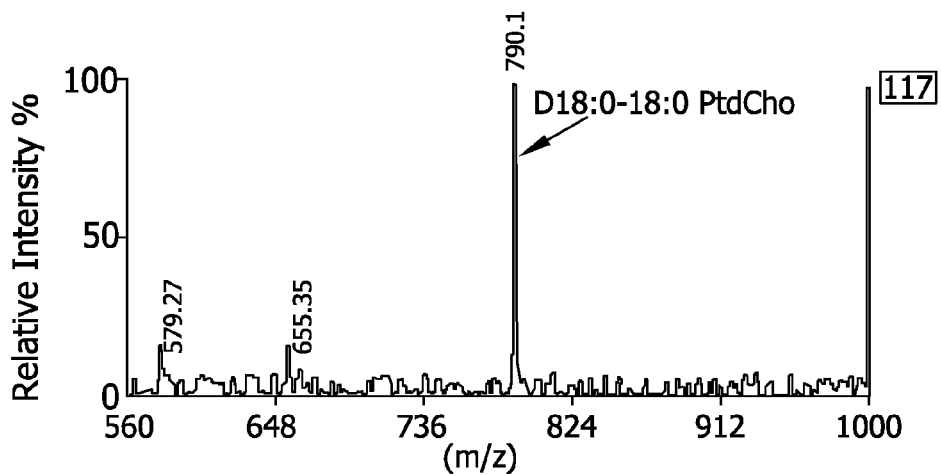
FIG. 17. Mass spectra of D18:0-18:0 PtdCho (diacyl phosphatidylcholine) acquired on a 4800 MALDI-TOF/TOF Analyzer in the positive ion mode using 10 mg/ml of 9-aminoacridine as matrix. Both 9-aminoacridine and D18:0-18:0 PtdCho were dissolved in: A) methanol; B) isopropanol; C) acetonitrile (9-aminoacridine was saturated in acetonitrile); or D) isopropanol/acetonitrile (60/40, v/v). Individual mass spectra were obtained by averaging 1500 consecutive laser shots (50 shots per subspectra with 30 total subspectra). Each spot contains 500 fmol D18:0-18:0 PtdCho. Ion counts are denoted in the top right of each panel enclosed in a box. The prefix "D" stands for diacyl (i.e., phosphatidyl-) species. As can be seen the generation of productive analyte/matrix interactions is dependent on the differential ability of discrete solvents to promote effective analyte matrix interactions resulting in over thirty fold increases in signal/noise in favorable cases.
Figure 17B:
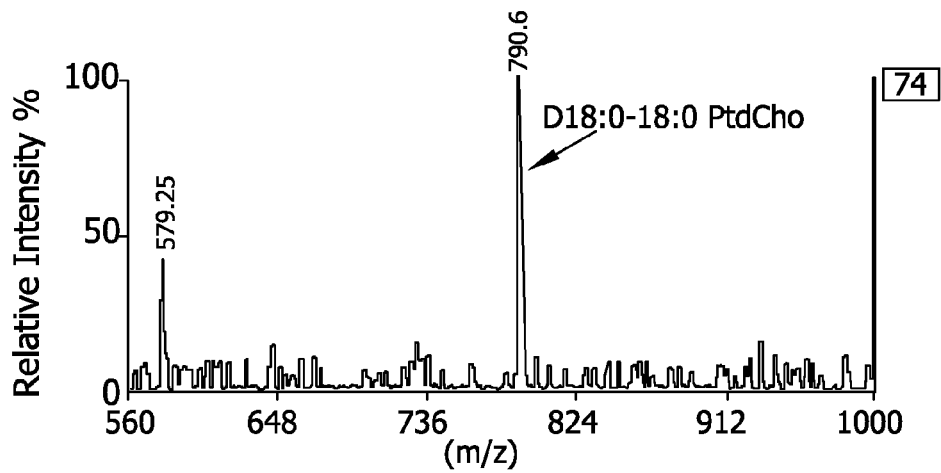
Figure 17C:
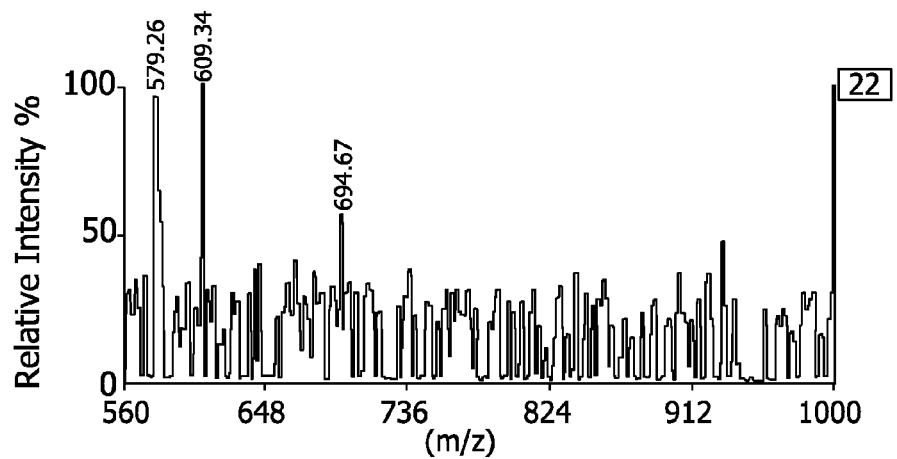
Figure 17D:
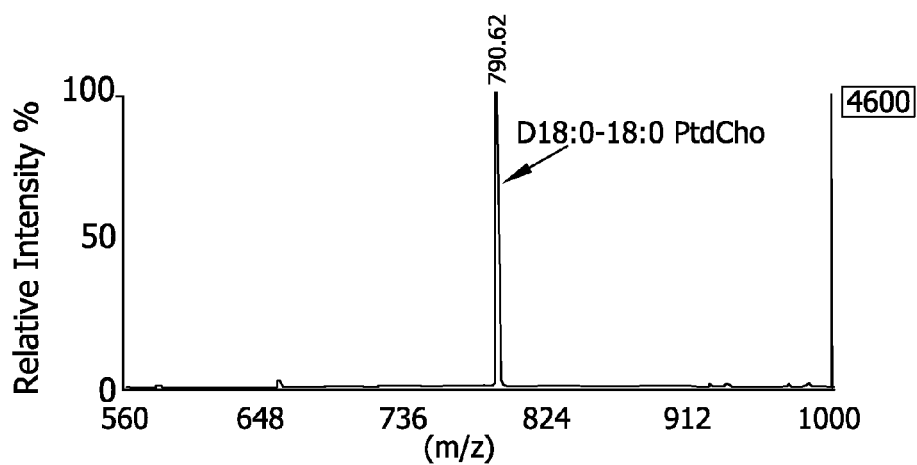
Figure 18A:
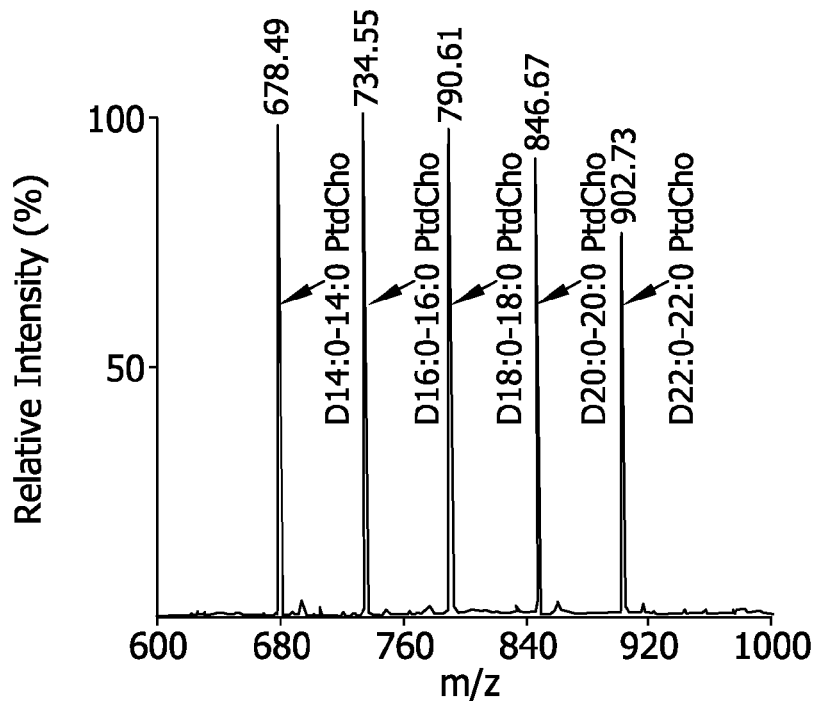
FIG. 18. Linearity and Dynamic Range For Quantitation of Representative Choline Glycerophospholipids Using Optimized Matrix/Analyte Interactions. A) Mass spectrum of an equimolar mixture of D14:0-14:0 PtdCho, D16:0-16:0 PtdCho, D18:0-18:0 PtdCho, D20:0-20:0 PtdCho and D22:0-22:0 PtdCho acquired on a 4800 MALDI-TOF/TOF Analyzer in the positive ion mode using 9-aminoacridine as matrix. B) Calculated amount of D14:0-14:0 PtdCho, D16:0-16:0 PtdCho, D18:0-18:0 PtdCho, D20:0-20:0 PtdCho and D22:0-22:0 PtdCho in spot resulted from spectrum A using D14:0-14:0 as internal standard (1 pmol/spot) after correction for $^{13}$C isotope effect. C) Mass spectra of an equal molar mixture of D18:3-18:3 PtdCho, D18:2-18:2 PtdCho, D18:1-18:1 PtdCho and D18:0-18:0 PtdCho acquired on a 4800 MALDI-TOF/TOF Analyzer in the positive ion mode using 9-aminoacridine as matrix. The amount of each individual PtdCho molecular species is 150 fmol. D) Calculated ratios of D18:2-18:2 PtdCho, D18:1-18:1 PtdCho and D18:0-18:0 PtdCho to D18:3-18:3 PtdCho at different concentrations. Each PtdCho molecule species was present at equal molar amount per spot concentration in D). E) Linear correlation between ion peak area ratios and the molar ratios of D18:2-18:2 PtdCho to D14:0-14:0 PtdCho in the molar ratio range 0.05-20. F) Linear correlation between the ion peak area ratios and the molar ratios of D18:2-18:2 PtdCho and D22:0-22:0 PtdCho in the molar ratio range 0.05-20. Each of the peak area ratios was determined from 17 fmol-5 pmol phospholipid per spot. Each data point represents the mean±SD from different concentrations of each PtdCho to another at each ratio tested. "s" and "$r^2$" represent the slope and correlation coefficient, respectively. Individual mass spectra were obtained by averaging 1500 consecutive laser shots (50 shots per subspectra with 30 total subspectra). The prefix "D" stands for diacyl (i.e., phosphatidyl-) species.
Figure 18B:
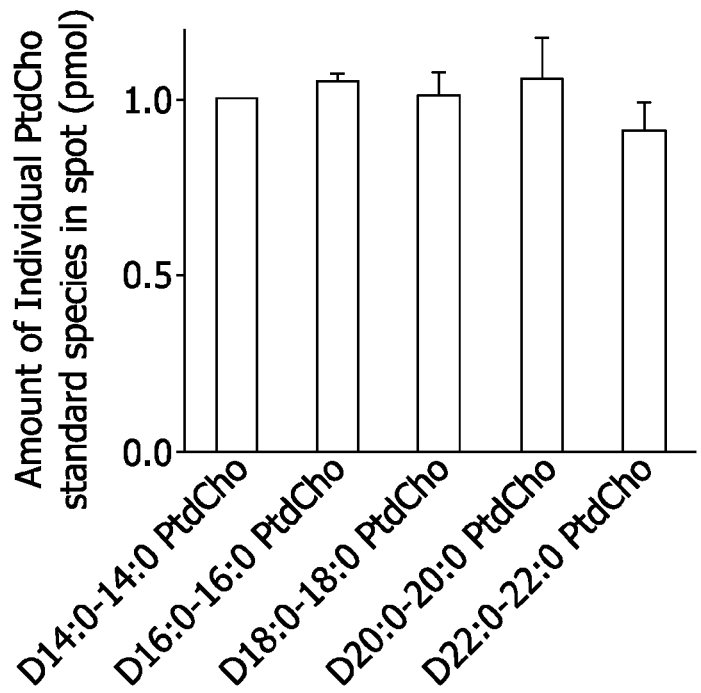
Figure 18C:
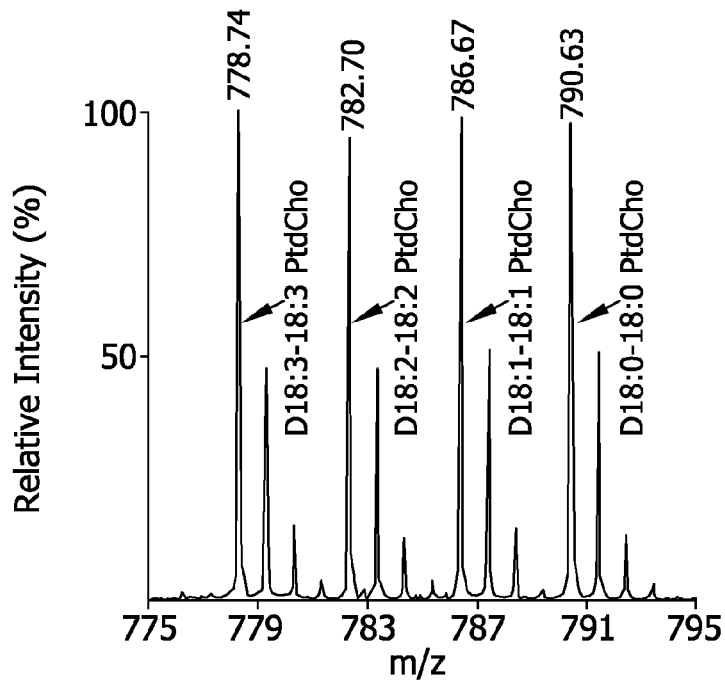
Figure 18D:
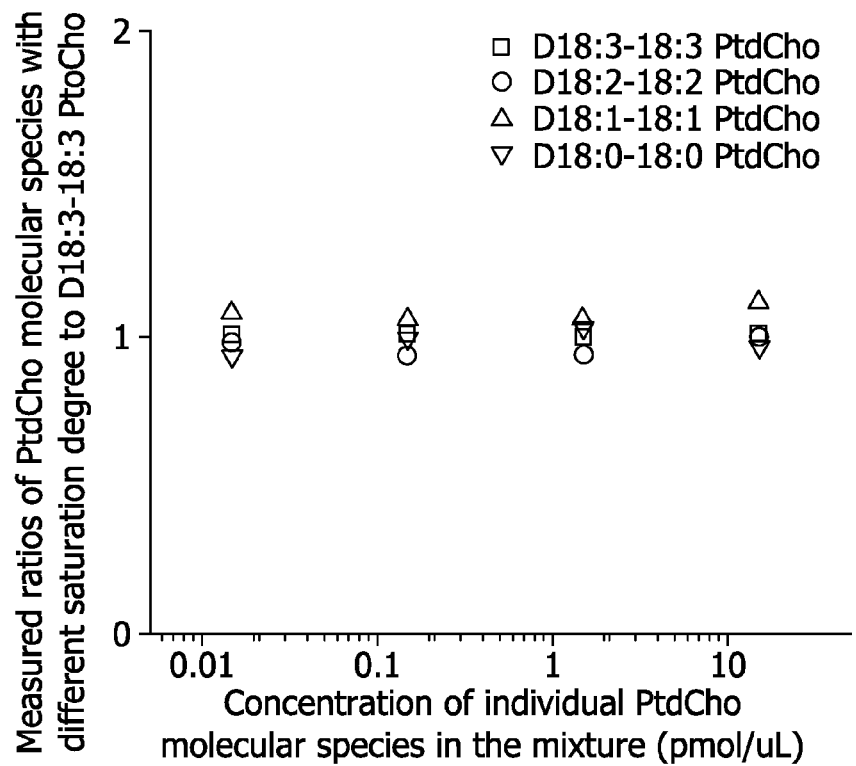
Figure 18E:
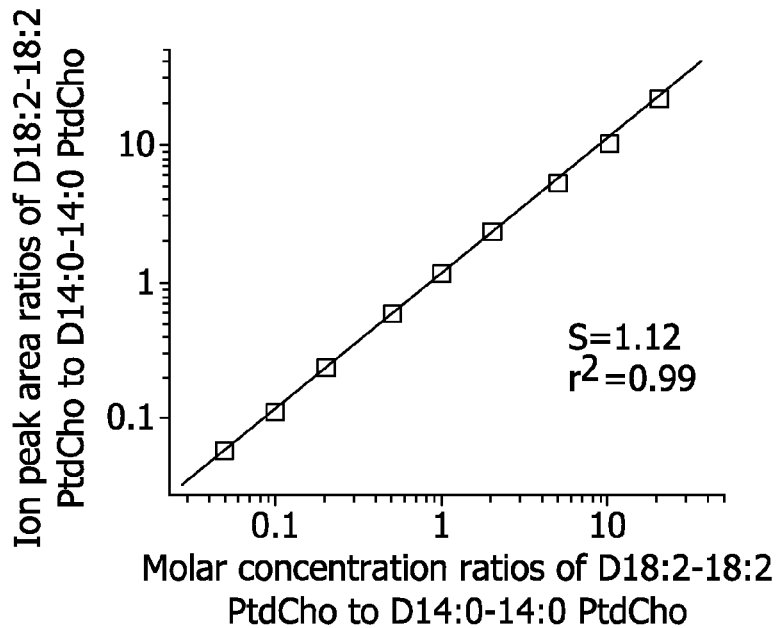
Figure 18F:
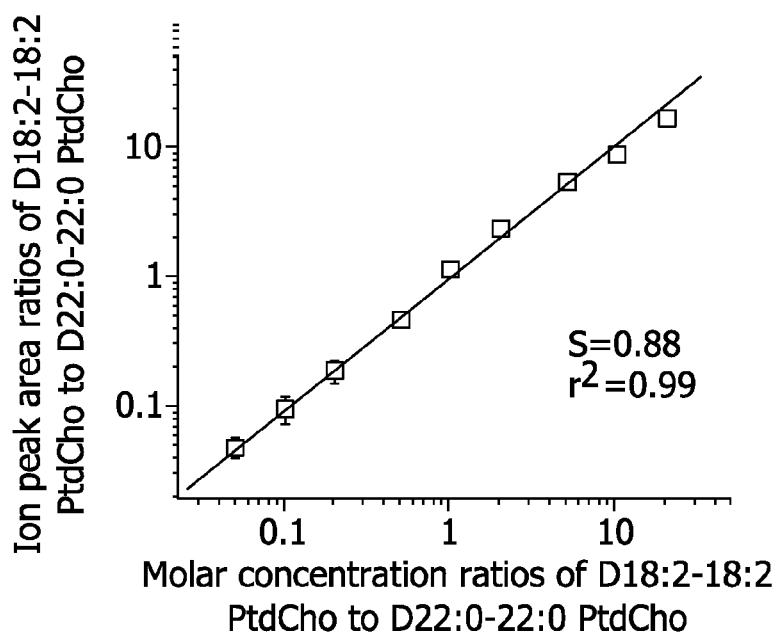

Thus, through parallel processing of samples and combinatorial matrixing of multiple stereoelectronic interactions hydrophobic metabolites that are extracted into the chloroform phase can also be effectively ionized and quantified (see below). Without being bound by theory, we believe that combinatorial multiplexing of matrix/analyte interactions are effected by alterations in the physical properties of the solvent that could promote substantial increases in the sensitivity of analysis and the selective ionization of hydrophobic metabolites. To explore this hypothesis, we examined multiple combinations of matrices and solvents to identify optimal conditions for the direct analysis of lipids by MALDI-MS. In initial experiments, it became clear that MALDI-MS spectra of lipids were critically dependent on the properties of the solvent used for dispersing the matrix and dissolving the lipids. For example, examination of 500 fmol of D18:0-18:0 PtdCho using 9-AA alone demonstrated only a very weak signal when the lipids and matrix were dispersed in methanol alone (FIG. 17(A)) or isopropanol alone (FIG. 17(B)). No signal was detectable when acetonitrile was employed as solvent alone (FIG. 17(C)). In stark contrast, a robust signal (4600 ion counts from 500 fmol) was routinely observed when lipids and matrix were mixed and spotted using binary mixtures of acetonitrile and isopropanol as solvent for both lipid dilution and matrix emulsion (e.g., FIG. 17(D)). Titration of different ratios of acetonitrile and isopropanol demonstrated that an acetonitrile/isopropanol ratio of 3:2 (v/v) was optimal in enhancing the S/N of the sample (FIG. 17(D)). Collectively, these results demonstrate that solvents profoundly modulate the generation of productive analyte-matrix interactions during MALDI-MS resulting at least about a 5 fold increase in signal/noise (S/N), and more suitably, at least about a 30 fold increase in S/N.

To explore the role of multiplexed analyte-matrix interactions in the identification and quantitation of hydrophobic metabolites, we examined the effects of alterations in chain length, the degree of unsaturation, and the dynamic range of the optimized method. First, we tested the potential suitability of solvent-enabled analyte matrix interactions for quantitative analyses of PtdCho. To this end, equimolar mixtures of D14:0-14:0 PtdCho, D16:0-16:0 PtdCho, D18:0-18:0 PtdCho, D20:0-20:0 PtdCho and D22:0-22:0 PtdCho were prepared and analyzed by MALDI-MS to determine the effects of chain length and hydrophobicity on the efficiency of ionization and desorption under these conditions. The results clearly demonstrated that the chain length and hydrophobicity of these species of PtdCho do not alter the ionization/desorption efficiency (FIG. 18(A-B)). It is important to note that the contributions from 13C isotopologues must be considered during quantitative analysis with MALDI-MS. Next, the effect of unsaturation in the aliphatic chains in PtdCho was examined. Through a thousand fold range in concentration (from 15 fmol to 15 pmol), the degree of unsaturation of PtdCho molecular species did not substantially effect the ionization/desorption efficiency of four different PtdCho molecular species (FIG. 18(C-D)). Thus, for PtdCho analysis the ionization/desorption efficiency of multiple PtdCho molecular species are nearly identical using the developed methods. Typically, the detection limit of PtdCho using D18:1-18:1 PtdCho is 5 fmol present in the MALDI plate spot.

Next, the dynamic range for PtdCho quantitation by MALDI-mass spectrometry was determined by analyses of mixtures of authentic PtdCho molecular species at selected concentrations. Plots of the ion peak area ratios of D18:2-18:2 PtdCho to D14:0-14:0 PtdCho versus their molar ratios in the mixture from a range of 17 fmol to 5 pmol per spot resulted in a line with a slope of 1.12 and a correlation coefficient of 0.99 (FIG. 18(E)). Similarly, plots of the ratios of D18:2-18:2 PtdCho to D22:0-22:0 PtdCho versus the actual molar ratios of authentic standards in the mixture resulted in a line with a slope of 0.88 and a correlation coefficient of 0.99 (FIG. 18(F)). Collectively, these results demonstrate that over a 100-fold dynamic range, individual PtdCho molecular species differing widely in chain length and degree of unsaturation could be accurately measured by MALDI-MS.

Figure 19A:
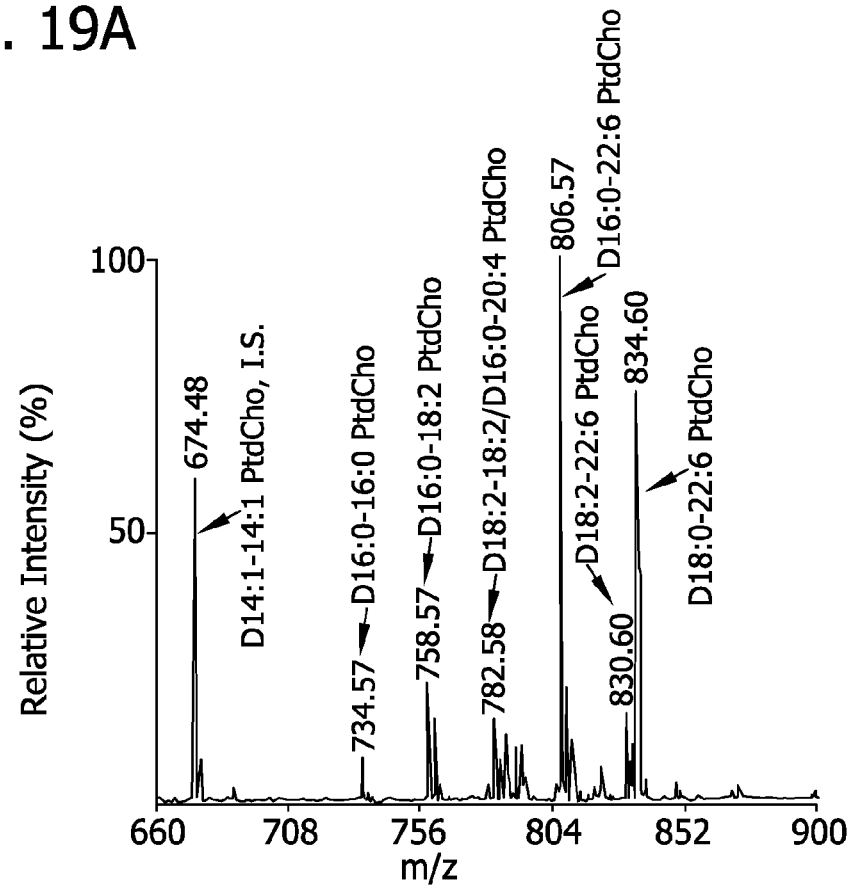
FIG. 19. Comparisons of the sensitivities of the current optimized analyte/matrix MALDI method for choline glycerophospholipids to previously developed MALDI approaches. Mouse heart extracts were examined and compared using: A) MALDI-TOF/TOF Analyzer utilizing optimized analyte matrix interactions with 9-aminoacridine as matrix dissolved in isopropanol/acetonitrile (60/40, v/v) or B) reported detection limits of previously published MALDI MS approaches for choline phospholipid detection using different matrices. The results clearly demonstrate the marked increase in sensitivity using the multiplexed solvent interaction approach (5 fmol; this work) in comparison to prior studies where either thousands of fentomoles using ionic liquid matrices were necessary[1] or conventional matrices (i.e, dihydroxybenzoic acid) where hundreds of fentomoles were necessary[2] or solid ionic crystal matrices which also required hundreds of fentomoles for their detection limit.[3] The results clearly indicate the dramatic increase in sensitivity of the multiplexed approach. In panel C, a representative tandem mass spectrum of lithiated D18:0-22:6 PtdCho from the mouse heart extracts was recorded in the positive ion mode using a 4800 MALDI-TOF/TOF Analyzer under optimized conditions with 9-aminoacridine as matrix and acetonitrile/isopropanol as solvent. The dramatically increased signal/noise facilitates acquisition of tandem ion spectra. Fragmentation was performed with CID with the metastable suppressor on and timed ion selector enabled. The voltages of source 1, the collision cell and the collision cell offset were 8.0 kV, 7.0 kV and −0.035 kV, respectively. The collision gas was air at medium pressure. The tandem MS spectrum was obtained by averaging 2000 consecutive laser shots (50 shots per subspectra with 40 total subspectra), The prefix "D" stands for diacyl (i.e., phosphatidyl-) species. "IS" denotes internal standard.
Figure 19B:
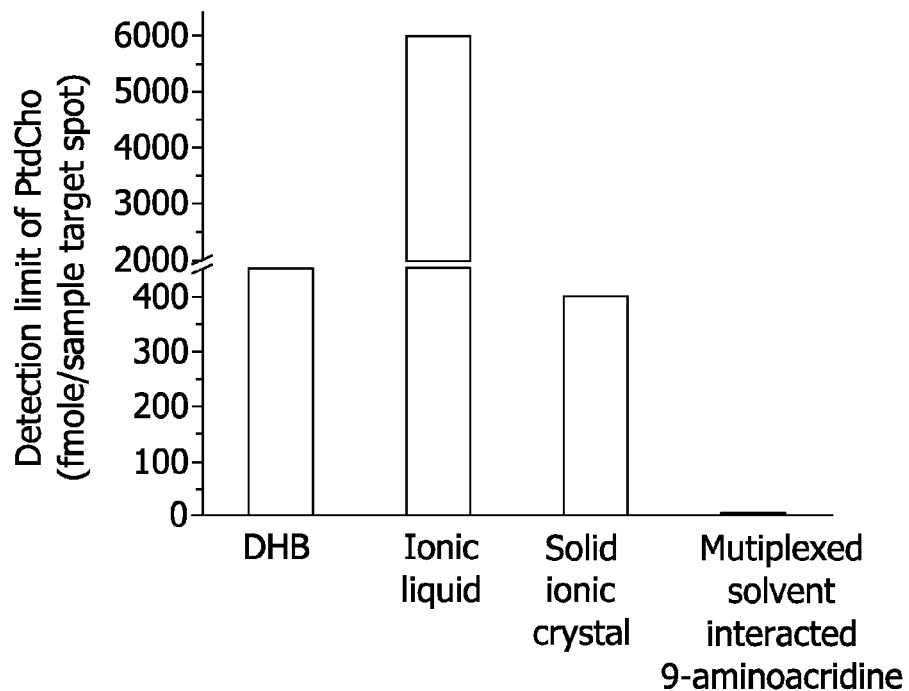
Figure 19C:
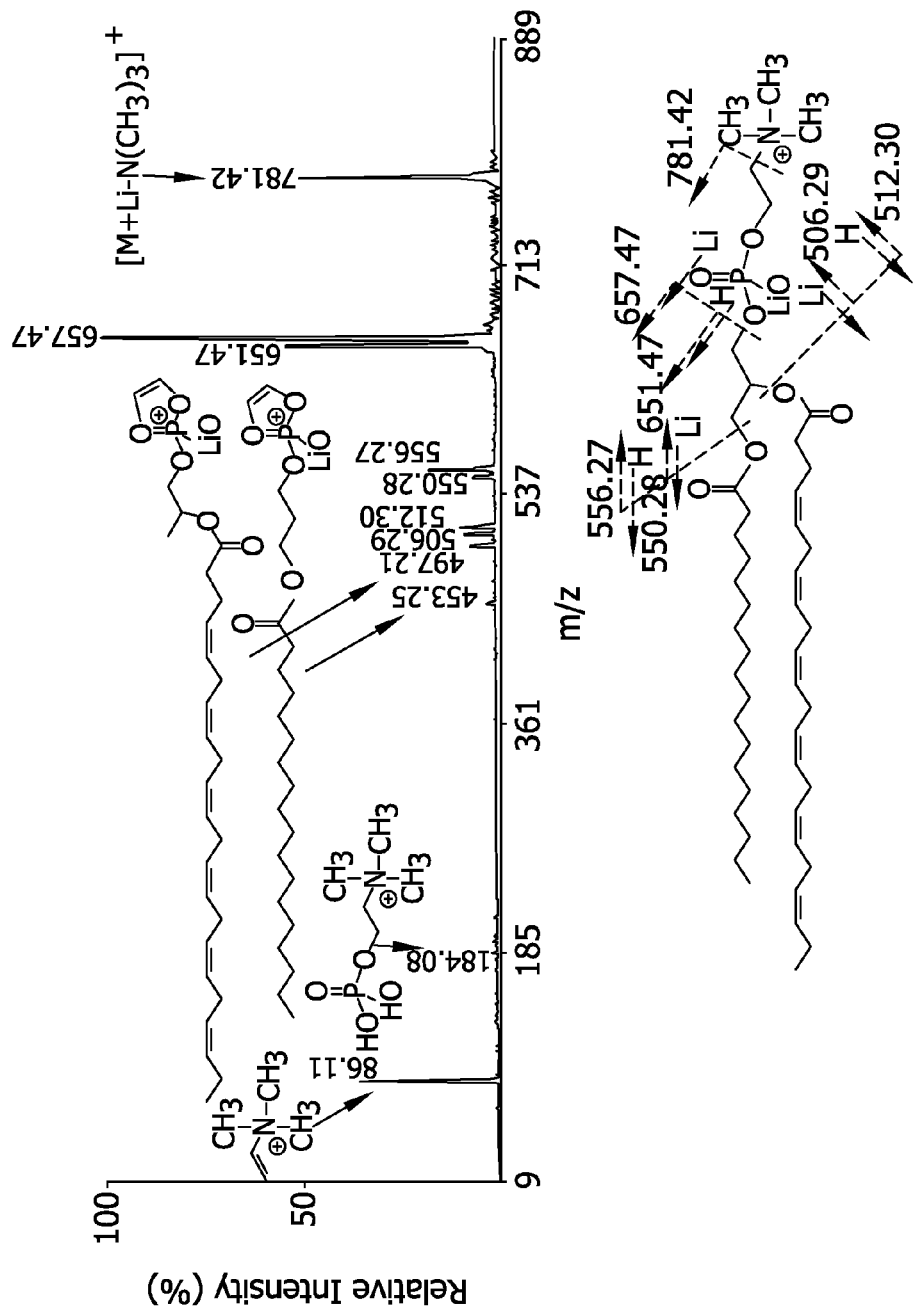

To determine the utility of this method for PtdCho quantitation from biologic materials, we compared the types and amounts of PtdCho molecular species present in a mouse heart lipid extract using MALDI-tandem mass spectrometry with results of the current "gold standard" for quantitation, ESI-MS shotgun lipidomics. Comparisons of the mass spectra from Bligh and Dyer extracts of myocardium demonstrated that the peak intensity of each PtdCho molecular species in the positive ion MALDI mass spectrum of murine myocardium under the conditions developed were present in essentially identical ratios as those presented previously using shotgun lipidomics with ESI-MS. Comparisons of the detection limits of lipids using MALDI with different matrices that have been developed are shown in FIG. 19B clearly identifying the vastly increased sensitivity of the method developed.

Figure 20A:
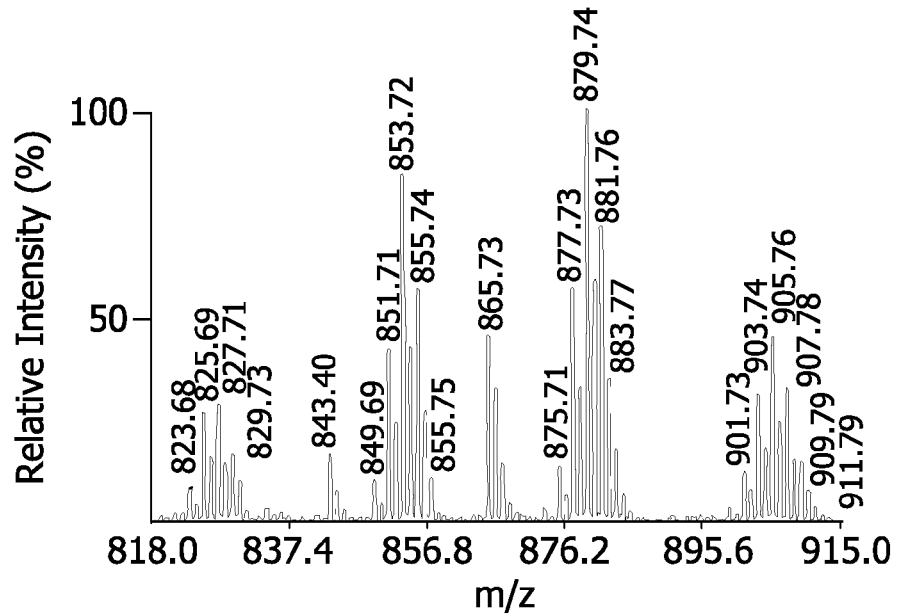
FIG. 20. Mass spectral comparison of triglyceride molecular species present in mouse adipose tissue lipid extracts acquired by: A) MALDI MS in the positive ion mode in comparison to the current gold standard for triglyceride analysis by shotgun lipidomics shown in B. Mouse fat tissue TAG extracts were prepared using hexane and identical extracts were examined by MALDI MS and ESI for the purpose of comparison. The MALDI-TOF/TOF mass spectrum of TAG molecular species was acquired on a 4800 MALDI-TOF/TOF Analyzer in the positive ion mode with 9-aminoacridine matrix dissolved in isopropanol/acetonitrile (60/40, v/v) containing 15 mM sodium acetate. Individual mass spectra were obtained by averaging 1500 consecutive laser shots (50 shots per subspectra and 30 subspectra). The ESI mass spectrum was recorded on a TSQ Quantum Ultra Plus triple-quadrupole mass spectrometer in the positive ion mode. As can be seen, the ratios of peak heights for each of the triglyceride ion peaks was essentially identical using either ESI or MALDI.
Figure 20B:
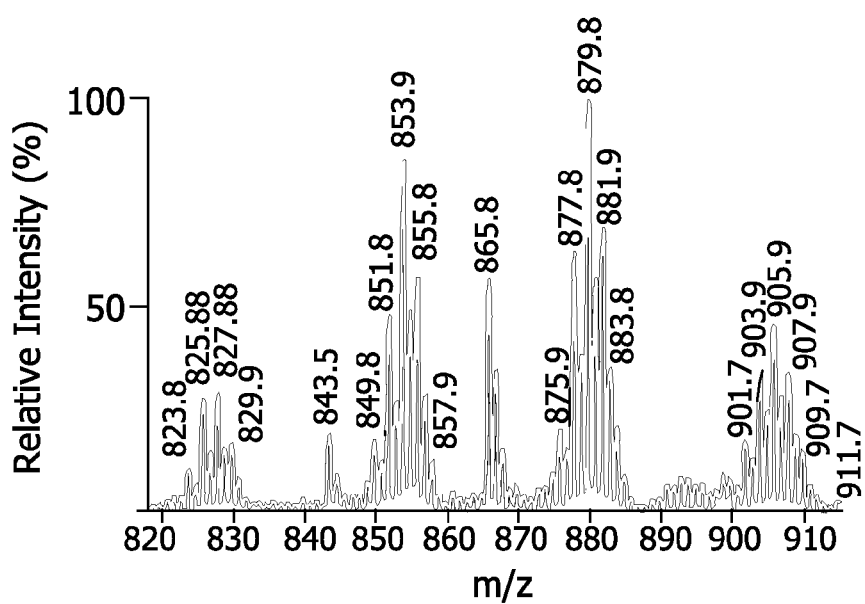
Figure 20C:
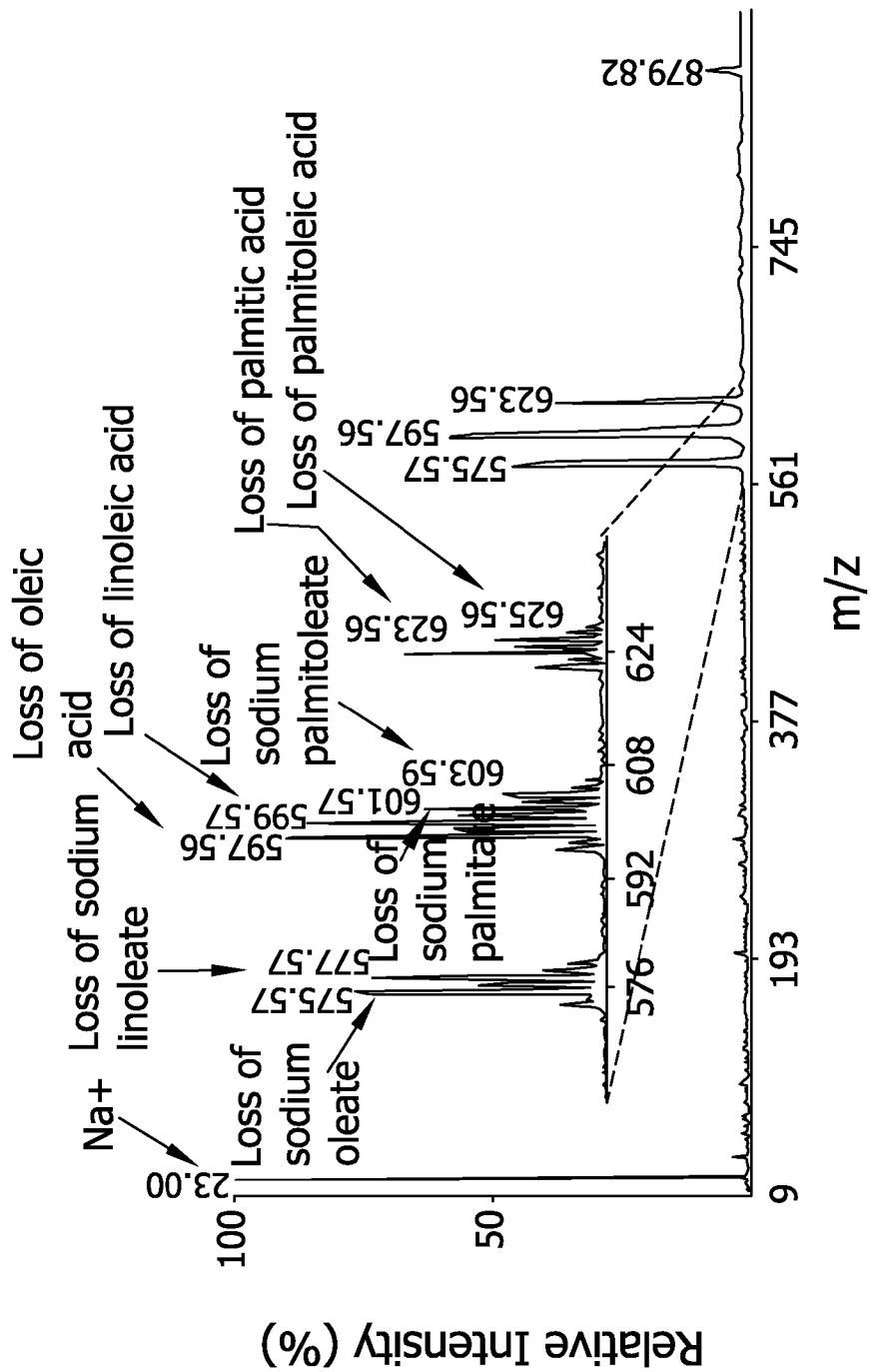
Figure 20D:
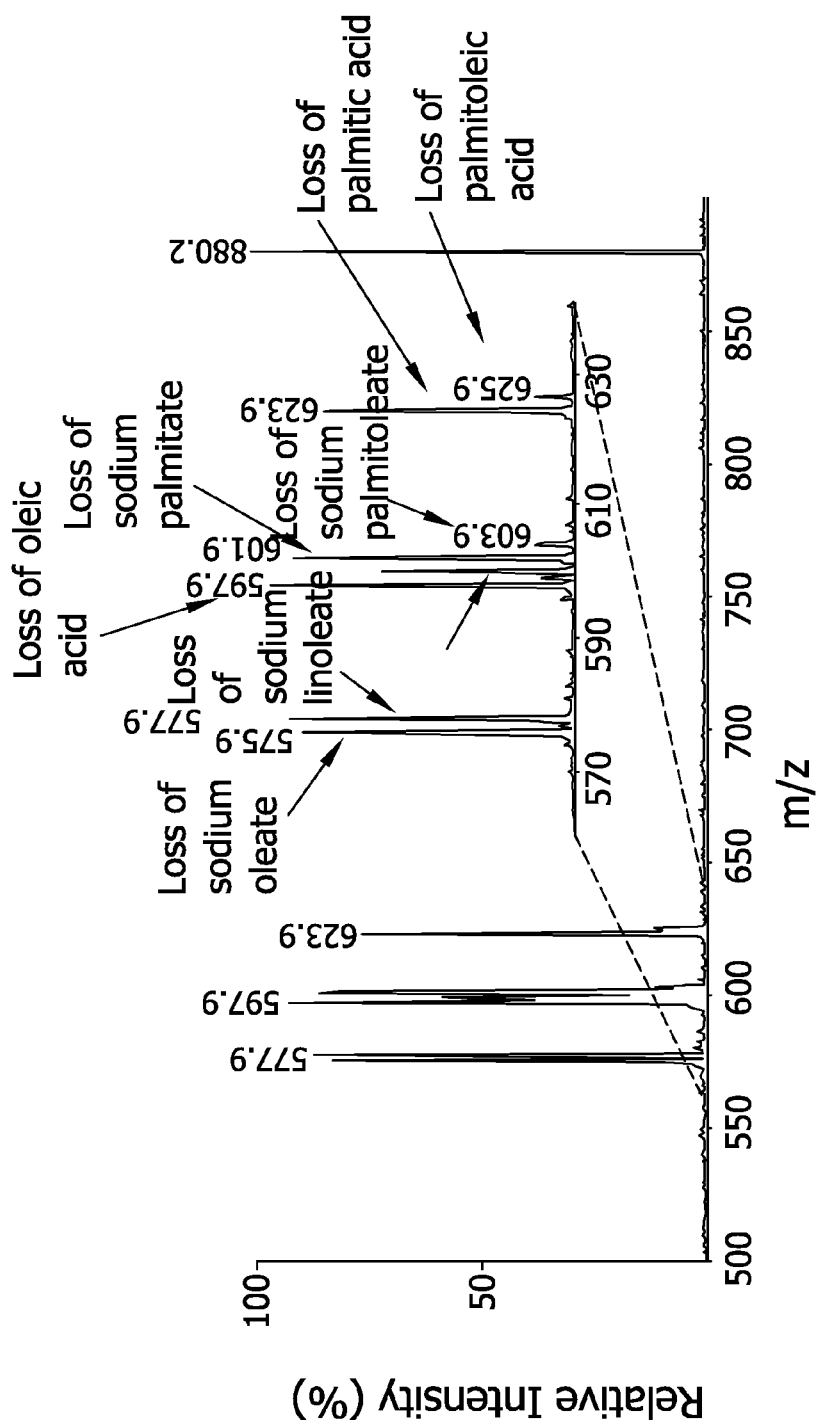
Figures 21A, 21B, 21C:
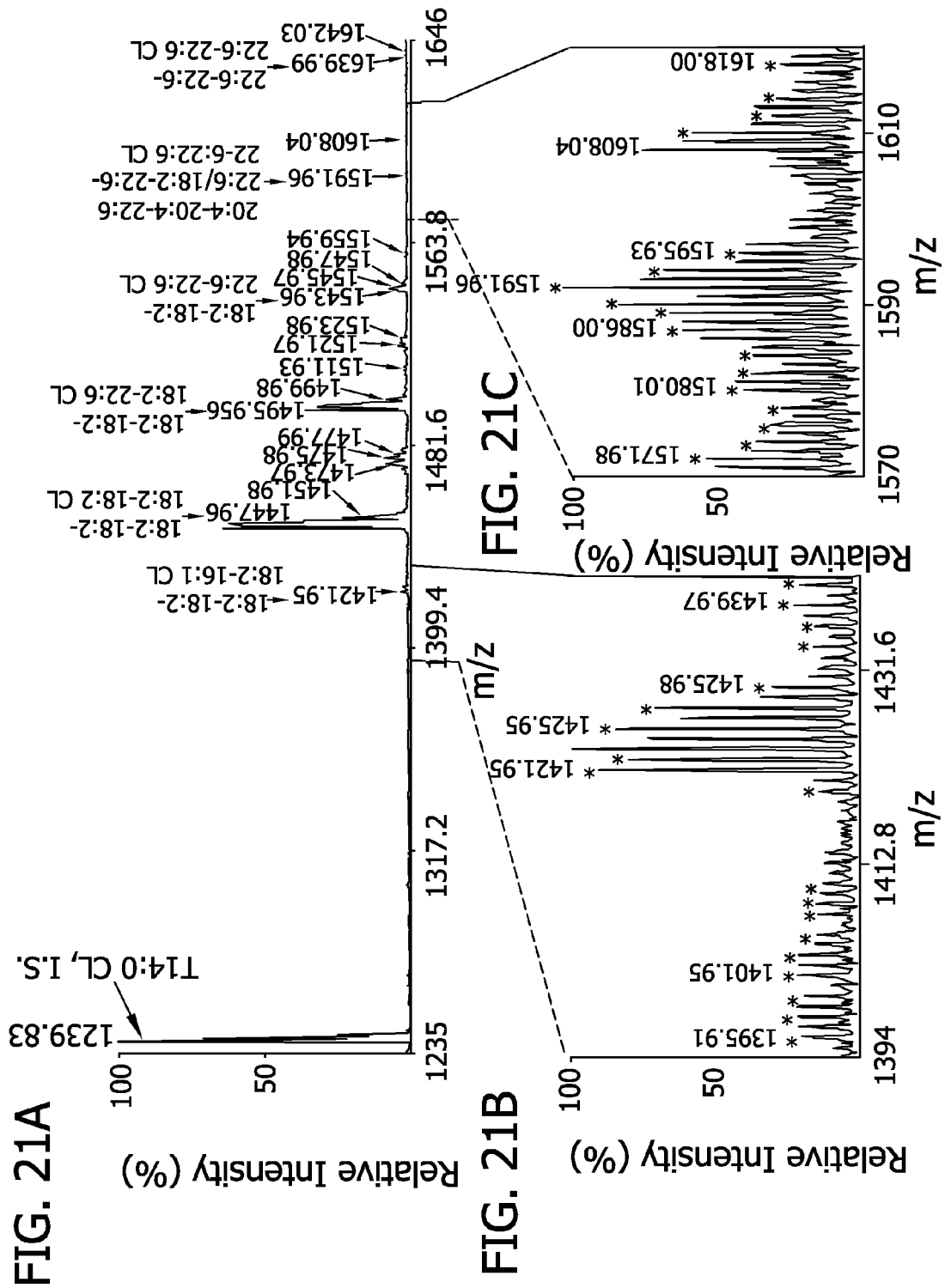
FIG. 21. Mass spectrum of cardiolipin (CL) present in mouse heart lipid extracts acquired on a 4800 MALDI-TOF/TOF Analyzer in the negative ion mode using optimized analyte/matrix interactions. Mouse myocardial CL was extracted by a modified Bligh and Dyer procedure. Individual mass spectra were obtained by averaging 1500 consecutive laser shots (50 shots per subspectra with 30 total subspectra). * indicates the identified CL molecular species peak. "IS" denotes internal standard.

Since quantitation of PtdCho by shotgun lipidomics using ESI-MS has been well established, these results validate the use of solvent-enabled MALDI-MS analysis using 9-aminoacridine as a matrix for quantitative analyses of PtdCho. The spectra of myocardial choline glycerolipids using electrospray ionization was acquired in 2 minutes while the spectrum for the identical sample of choline glycerolipids using optimized analyte/matrix interactions was acquired in less than 10 s representing over an order of magnitude increase in the speed of data acquisition. Moreover, the results with optimized matrix/analyte interactions require much shorter time intervals for data acquisition (15 seconds in comparison to 2 minutes) that have typically been utilized thus far for metabolomics analyses. Finally, MALDI tandem mass spectrometry of choline glycerolipids using optimized matrix/analyte interactions facilitates metabolite identification through increasing the signal of individual molecular species enabling tandem mass spectrometric analyses (FIG. 20(C)).

Since triglycerides (TAG) do not contain an intrinsically charged moiety and did not ionize/desorb under the previously developed conditions, it was necessary to introduce oxytropic ions into the matrix to facilitate charge separation leading to successful ionization/desorption. This strategy has previously been used successfully with other matrices to enhance TAG ionization/desorption. Three additives, 15 mM ammonium acetate, 15 mM lithium acetate and 17 mM sodium acetate, were examined to improve the conditions for TAG analysis. Doping of the matrix with sodium acetate provided the best results. Next we compared the ratios of the intensities of ionized triglyceride molecular species by optimized analyte matrix interactions to the current standard of ESI-MS. The results demonstrated nearly identical profiles of triglyceride molecular species using MALDI-MS in comparison to ESI-MS (FIG. 20(A-B)). Moreover, results with MALDI can be accrued in 10-20 seconds while scans for ESI (including the one presented) take at least 2 minutes or longer and even at these longer time periods are contaminated by significantly more noise. MALDI-tandem mass spectrometric analysis of the TAG molecular species at m/z 879.74 was successful (FIG. 20 (C-D)). Fragment ions at m/z 575.57, 577.57, 601.57 and 603.59 representing neutral losses of sodium oleate, sodium linoleate, sodium palmitate, sodium palmitoleate acid from sodiated TAG molecular species at m/z 879.82 were easily identified. The presence of both groups of fragments unambiguously identifies oleoyl, linoleoyl, palmitoyl and palmitoleoyl chains in this isobaric peak demonstrating the presence of a combination of 18:1-18:1-16:1 TAG and 18:2-18:1-16:0 TAG. Array analysis of tandem spectra can be utilized to rapidly determine complex triglyceride compositions.

CONCLUSIONS

In this study, a highly sensitive (attomole to fentomole sensitivity) shotgun metabolomics approach using MALDI-tandem mass spectrometry was developed for the high throughput identification and quantitation of biologic metabolites in biologic materials. Through development of an integrated set of multiplexed conditions (differential extraction, differential partitioning, combinatorial analyte-matrix stereoelectronic interactions, differential fragmentation energy), identification of many hundreds of peaks corresponding to charged metabolites (or metabolites that can be induced to contain a charge) from mouse heart extracts was achieved. In many cases, identified metabolites were confirmed by MALDI-tandem mass spectrometry. The distribution of isomeric molecular species of many metabolites, especially signaling metabolites, could be determined through identification of diagnostic fragment ions. Moreover, spectrometric isolation of closely neighboring peaks could be achieved by choosing suitable combinatorial conditions for multiplexed ionization with subsequent bioinformatics analyses. Collectively, these results identify the utility of multiplexed ionization conditions for the direct analysis of complex metabolomes by MALDI-tandem mass spectrometry without the need for chromatographic separation of the diverse array of functionalities present in complex mixtures from biological sources. This method of combinatorial multiplexing should be broadly applicable to quantitative analyses of complex mixtures from biologic and other sources (drugs, petroleum extracts, bacteria identification, toxins, etc).

In one embodiment, a method for rapid highly sensitive analysis of cellular metabolites includes inactivating endogenous enzyme activities using neutral organic solvents in cooperation with a matrix having minimal background noise. A set of multiplexed conditions were developed to facilitate the generation of combinatorial sets of productive analyte/matrix interactions which lead to increased signal intensity and spectrometric isolation of targeted groups of metabolites directly from biologic materials including, without limitation, extracts of human biologic tissues, fluids and organic matter. Metabolite peaks are identified based on mass accuracy and identification is confirmed using tandem mass spectrometry. The ionization conditions are multiplexed to facilitate ionizing new suites of metabolites that can be quantified by ratiometric comparisons to standards. Closely neighboring peaks are spectrometrically isolated for subsequent tandem mass spectrometric interrogation by engineered analyte matrix pairing. In a particular embodiment, diagnostic fragmentation ions are identified to facilitate assigning ions from isomeric metabolites. The relative abundance of the assigned ions is quantified by ratiometric comparisons. Extremely low abundance metabolites including important signaling metabolites, such as IP3, cAMP, and cGMP, can be detected and quantified by comparisons with standards.

In one embodiment, a multiplexed MALDI-tandem mass spectrometric method for analysis of metabolites in mammalian tissues including the multiplexed extraction of the metabolite from a mammalian tissue. A sample of the extracted water soluble and lipid soluble metabolites are reconstituted individually and analyzed using MALDI-tandem mass spectrometry in either the positive or negative ion mode. The extracted metabolites are identified utilizing an iterative procedure, wherein an ion from a data base (or an internal standard) is identified and assignments are confirmed by tandem MS analyses. In a particular embodiment, spectra are recalibrated using the identified metabolites as internal standards of known mass for peak assignment and added isotopic labeled compounds as internal standards for quantitation. Identities for extremely low abundance peaks are assigned and the assigned identities are confirmed using tandem MS analysis. The stereoelectronic interactions in the aromatic matrix are varied to facilitate productive ionization and desorbtion by multiplexing analyte-matrix interactions which are critical for the successful ionization/desorption of metabolites with different chemical properties.

While the invention has been described in terms of various specific embodiments, those skilled in the art will recognize that the invention can be practiced with modification.

What is claimed is:

1. A method for the rapid and highly sensitive analysis of cellular metabolites directly from extracts of biologic material, said method comprising:
    inactivating endogenous enzyme activities of the biologic material using at least one neutral organic solvent to prevent degradation of the biologic material;
    extracting at least one metabolite from the biologic material;
    developing a set of multiplexed conditions for MALDI ionization and desorption of the metabolite extracted from the biologic material on a matrix having minimal background noise that enable class selective ionization and desorption of the metabolite directly from extracts of the biological material, wherein the multiplexed conditions include varying the pH from a pH of about 3.0 to about 10.0, and wherein the selective ionization is engineered by combinatorial sets of matrix-analyte interactions.

2. A method in accordance with claim 1 wherein the metabolites are selected from the group consisting of cellular signaling metabolites, lipid signaling metabolites, metabolites involved in energy production; metabolites of intermediary metabolism; oxidized metabolites and lipid metabolites.

3. A method in accordance with claim 1 further comprising identifying metabolic peaks based on mass accuracy and confirming the identification using tandem mass spectrometry.

4. A method in accordance with claim 1, wherein the inactivating of enzyme activities using neutral organic solvents and subsequent formation of engineered analyte-matrix pairs are multiplexed to facilitate the selective ionization/desorption and identification of the metabolites with fentomole sensitivity by matrix assisted laser desorption ionization mass spectrometry.

5. A method in accordance with claim 3 further comprising spectrometrically isolating closely neighboring peaks of the identified metabolic peaks for subsequent tandem mass spectrometric interrogation by selective ionization/desorption of one or more of the peaks by engineered analyte-matrix pairs.

6. A method in accordance with claim 5 further comprising:
    using tandem mass spectrometry after MALDI ionization to assign isomeric metabolites present in each ion peak;
    quantifying the relative abundance of the assigned ions through ratiometric comparisons using at least one of the stable isotope standards and metabolite standards having similar ionization/desorption properties; and
    detecting and quantifying low abundance signaling metabolites selected from the group consisting of IP3, cAMP, cGMP, eicosanoids, and combinations thereof.

7. A method in accordance with claim 1, wherein the developing of multiplexed conditions leads to at least about 5 fold increase in signal/noise.

8. A method in accordance with claim 1, wherein the matrix having minimal background noise is selected from the group consisting of a silicon nanoparticle, mesotetrakis(pentafluorophenyl)porphyrin, 9-aminoacridine, porous silicon, cyanohydroxycinnamic acid, dihyroxybenzoic acid, trihydroxyacetophenone and ionic liquid matrices.

9. A method in accordance with claim 1, wherein the selective ionization is conducted in three stages, wherein the first stages comprises a pH of from about 2.0 to about 3.0, the second stage comprises a pH of from about 6.0 to about 8.0, and the third stage comprises a pH of from about 9.5 to about 10.5.

10. A method in accordance with claim 1, wherein the biologic materials are selected from the group consisting of mammalian tissue, fluid from mammals, and excretions from mammals.

11. A method in accordance with claim 10, wherein the mammalian tissue, fluid or excretions are from humans.

12. A method in accordance with claim 1, wherein the extracted metabolites from the biologic material can result from non-enzymatic transformations selected from the group consisting of free radical oxidation, nitrosylation, acylation, and introduction of pharmaceutical compounds and metabolites.

13. A method in accordance with claim 1 wherein the multiplexed condition includes adding at least one adjuvant to the matrix.

14. A method in accordance with claim 13, wherein the adjuvant is selected from the group consisting of glycerol and cations.

15. A method in accordance with claim 1, wherein the selective ionization/desorption is conducted in less than about 20 seconds per sample.

16. A multiplexed matrix assisted laser desorption ionization mass spectrometry method for analysis of metabolites in mammalian tissues, said method comprising:
    multiplexed-extracting of at least one metabolite from the mammalian tissue;
    reconstituting a sample of the extracted metabolite in a solvent mixture comprising a solvent and a matrix to form at least one engineered analyte-matrix pair;

using a multiplexed mixture of 9-aminoacridine-analytes to facilitate ionization of metabolite classes by analyzing the reconstituted sample using high throughput matrix assisted laser desorption ionization mass spectrometry;

identifying individual metabolites of the reconstituted sample utilizing an iterative procedure comprising identifying an ion from a data base and confirming assignments by tandem mass spectrometric analysis;

recalibrating spectra using the identified individual metabolites as internal standards of known mass for peak assignment and adding isotopic labeled compounds as internal standards for quantitation;

assigning identities for low abundance peaks and confirming the assigned identities using tandem mass spectrometric analysis; and varying stereoelectronic interactions of the matrix to facilitate desorption by combinational sets of multiplexed matrix analyte interactions.

17. A method in accordance with claim 16, wherein the reconstituting the sample of the extracted metabolite in the solvent mixture increases the specific ionization/desorption of the metabolite enabling tandem mass spectrometric analysis.

18. A method in accordance with claim 16, wherein the multiplex-extracting comprises varying the pH from a pH of about 3.0 to about 10.5.

19. A method in accordance with claim 18, wherein the multiplex-extracting comprises three stages, wherein the first stages comprises a pH of from about 2.0 to about 3.0, the second stage comprises a pH of from about 6.0 to about 8.0, and the third stage comprises a pH of from about 9.5 to about 10.5.

20. A method in accordance with claim 16, wherein analyzing the reconstituted sample is conducted in less than about 20 seconds.

* * * * *